US009553274B2

(12) United States Patent
Xia et al.

(10) Patent No.: US 9,553,274 B2
(45) Date of Patent: *Jan. 24, 2017

(54) ORGANIC ELECTROLUMINESCENT MATERIALS AND DEVICES

(71) Applicant: Universal Display Corporation, Ewing, NJ (US)

(72) Inventors: Chuanjun Xia, Lawrenceville, NJ (US); Scott Joseph, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 594 days.

This patent is subject to a terminal disclaimer.

(21) Appl. No.: 13/942,921

(22) Filed: Jul. 16, 2013

(65) Prior Publication Data

US 2015/0021556 A1     Jan. 22, 2015

(51) Int. Cl.
| | | |
|---|---|---|
| *H01L 51/50* | (2006.01) | |
| *H01L 51/00* | (2006.01) | |
| *C07D 491/04* | (2006.01) | |
| *C07D 495/04* | (2006.01) | |
| *C09B 57/00* | (2006.01) | |

(52) U.S. Cl.
CPC ......... *H01L 51/0072* (2013.01); *C07D 491/04* (2013.01); *C07D 495/04* (2013.01); *C09B 57/00* (2013.01); *H01L 51/0071* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

European Search Report dated Oct. 14, 2014 for corresponding EP Application No. 14176868.9.

(Continued)

*Primary Examiner* — Gregory Clark
(74) *Attorney, Agent, or Firm* — Duane Morris LLP

(57) ABSTRACT

The present disclosure generally relates to novel compounds containing carbazole and triazine with different number of phenyl units attached to its core. In particular, the disclosure relates to compositions and/or devices comprising these compounds as hosts for PHOLEDs.

21 Claims, 3 Drawing Sheets

(56) References Cited

U.S. PATENT DOCUMENTS

| | | |
|---|---|---|
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,227,801 B2 | 7/2012 | Xia et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0260138 A1* | 10/2011 | Xia .................. C07D 405/14 257/40 |
| 2011/0278552 A1 | 11/2011 | Numata et al. |

FOREIGN PATENT DOCUMENTS

| | | |
|---|---|---|
| EP | 2034538 | 3/2009 |
| EP | 2762477 | 8/2014 |
| JP | 8003547 | 1/1996 |
| JP | 2001220380 | 8/2001 |
| JP | 200511610 | 1/2005 |
| JP | 2007123392 | 5/2007 |
| JP | 2007194241 | 8/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006025186 | 3/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

(56) References Cited

OTHER PUBLICATIONS

Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylbory1)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett, 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Brunner Klemens et al., Carbazole compounds as host materials for triplet emitters in organic light-emitting diodes: tuning the HOMO level without influencing the triplet energy in small molecules, J. Am. Chem. Soc. 2004, 126, pp. 6035-6042.

* cited by examiner

Formula I

ORGANIC ELECTROLUMINESCENT MATERIALS AND DEVICES

FIELD OF THE INVENTION

The present disclosure generally relates to novel compounds containing carbazole and triazine with different number of phenyl units attached to their core. In particular, the disclosure relates to compositions and/or devices comprising these compounds as hosts for PHOLEDs.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

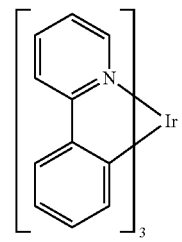

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an aspect of the present disclosure, a compound having a structure according to Formula I

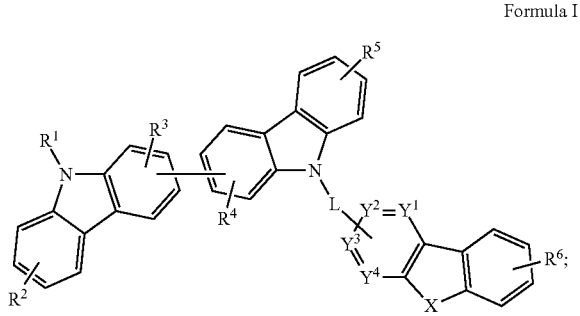

Formula I wherein $R^2$, $R^5$, and $R^6$ represent mono, di, tri, tetra substitutions or no substitution; wherein $R^3$, and $R^4$ represent mono, di, tri substitutions or no substitution; wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof; wherein X is selected from the group consisting of O, S, and Se; wherein $Y^1$, $Y^2$, $Y^3$, and $Y^4$ comprise C or N; wherein at least two of $Y^1$, $Y^2$, $Y^3$, and $Y^4$ are N; wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof is provided.

According to another aspect of the present disclosure, a first device comprising an organic light emitting device is disclosed. The organic light emitting device comprises an anode, a cathode, and an organic layer disposed between the anode and the cathode, wherein the organic layer comprises a compound having a structure according to Formula I

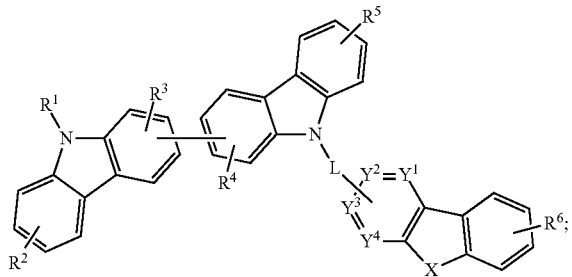

Formula I wherein $R^2$, $R^5$, and $R^6$ represent mono, di, tri, tetra substitutions or no substitution; wherein $R^3$, and $R^4$ represent mono, di, tri substitutions or no substitution; wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof; wherein X is selected from the group consisting of O, S, and Se; wherein each of $Y^1$, $Y^2$, $Y^3$, and $Y^4$ is carbon or nitrogen; wherein at least two of $Y^1$, $Y^2$, $Y^3$, and $Y^4$ are nitrogen; wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment of the first device, the organic layer is an emissive layer and the compound having Formula I is a host. In one embodiment, the organic layer further comprises an emissive dopant. In one embodiment, the organic layer is a blocking layer and the compound having Formula I is a blocking material in the organic layer. In one embodiment, the organic layer is an electron transporting layer and the compound having Formula I is an electron transporting material in the organic layer.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton", which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
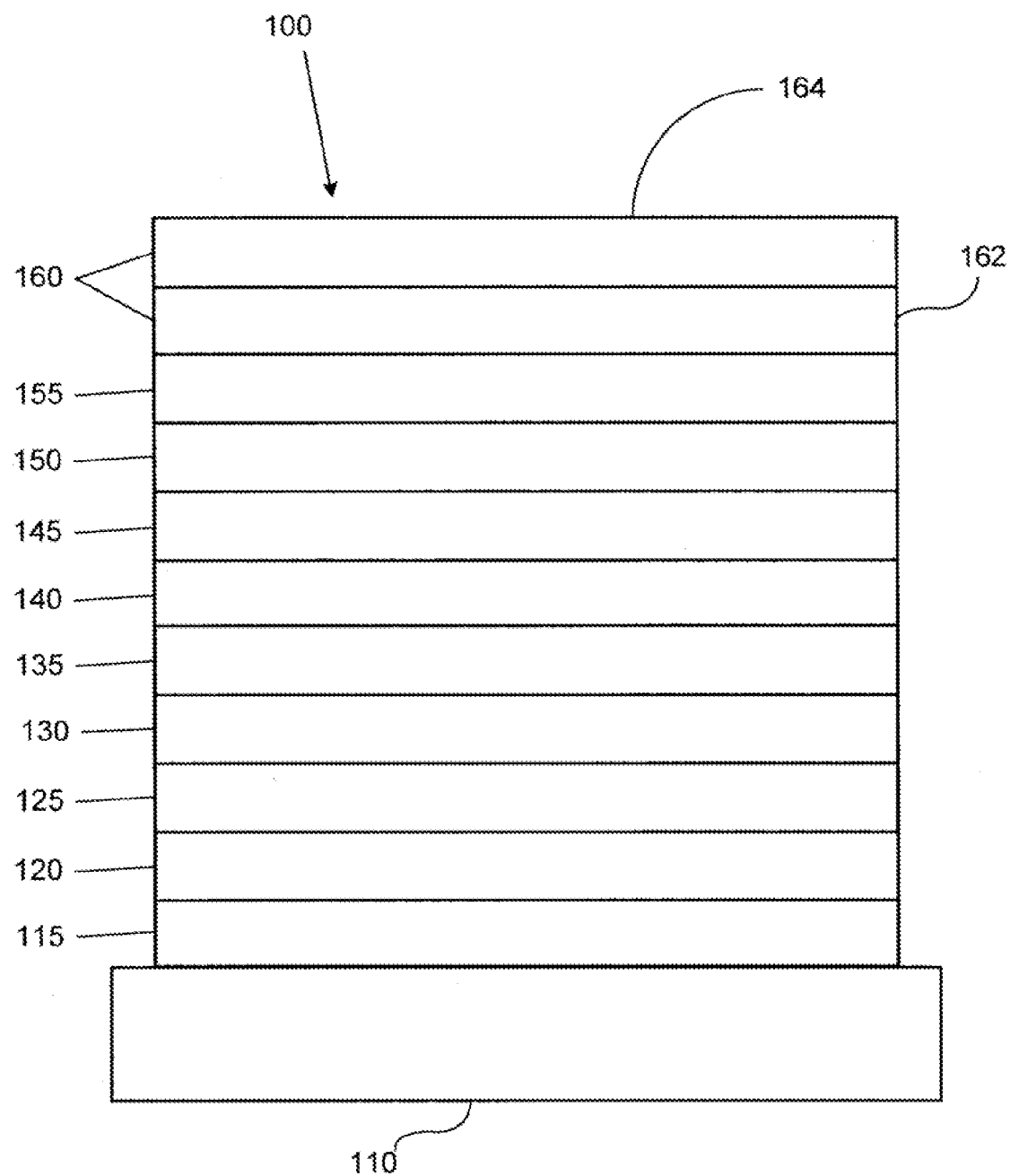
FIG. 1 shows an organic light-emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
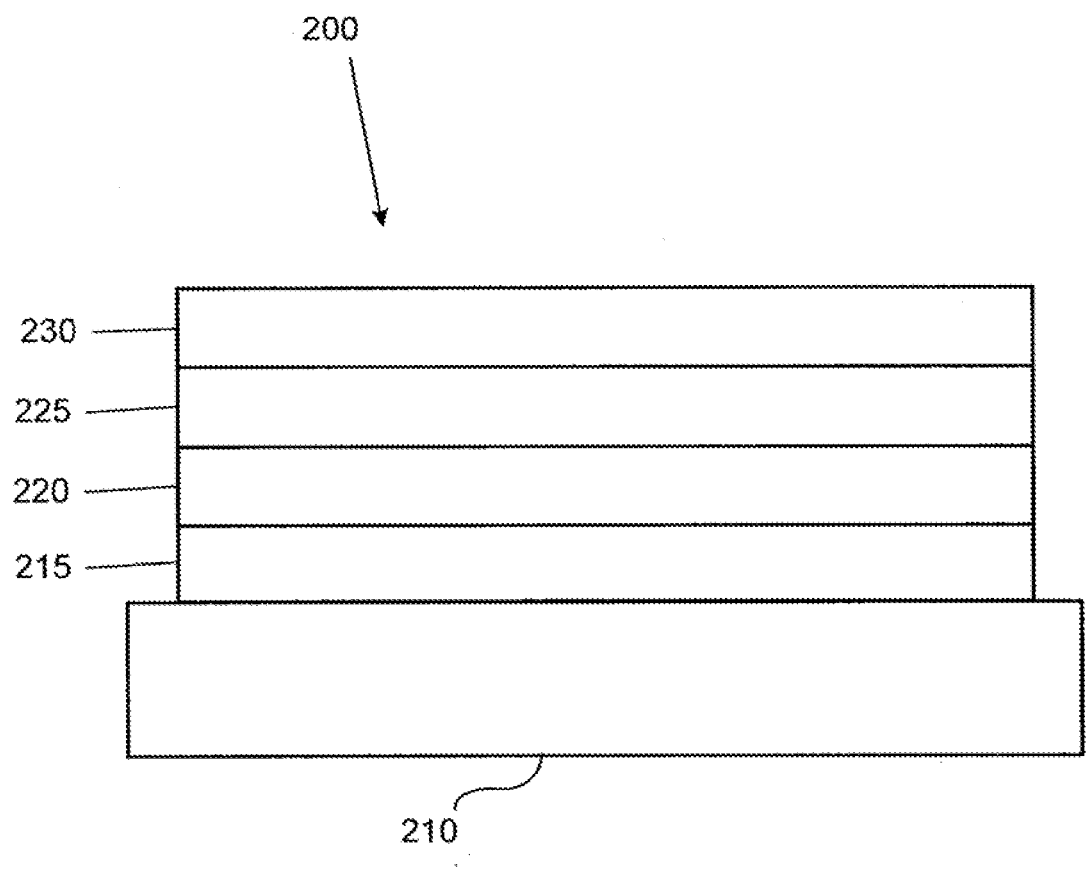
FIG. 2 shows an inverted organic light-emitting device that does not have a separate electron transport layer.
Figure 3:
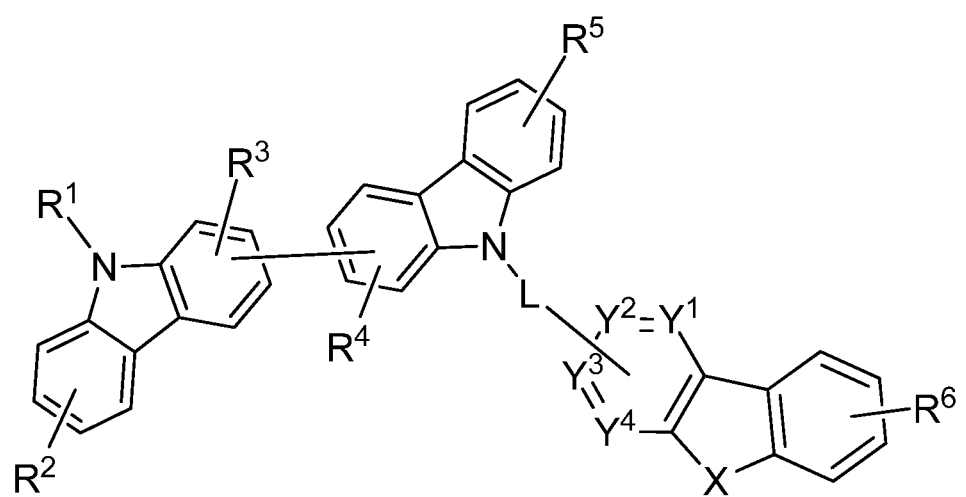
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

According to an aspect of the present disclosure, a compound having a structure according to Formula I Formula I

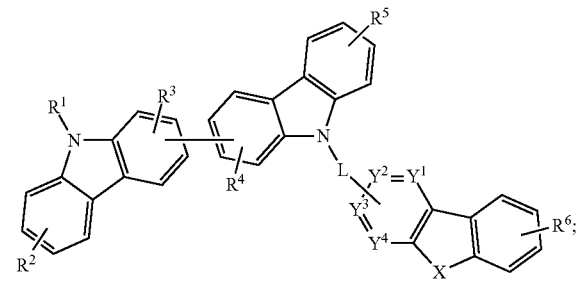

wherein $R^2$, $R^5$, and $R^6$ represent mono, di, tri, tetra substitutions or no substitution;

wherein $R^3$, and $R^4$ represent mono, di, tri substitutions or no substitution;

wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;

wherein X is selected from the group consisting of O, S, and Se;

wherein each of $Y^1$, $Y^2$, $Y^3$, and $Y^4$ is carbon or nitrogen;

wherein at least two of $Y^1$, $Y^2$, $Y^3$, and $Y^4$ are nitrogen;

wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof is provided.

In one embodiment of the compound, $R^1$ is aryl or heteroaryl. In one embodiment, $R^1$ is selected from the group consisting of phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof. In one embodiment, $R^2$, $R^3$, $R^4$, $R^5$ and $R^6$ are each independently selected from the group consisting of hydrogen, deuterium, aryl, heteroaryl and combinations thereof. In one embodiment, $R^2$, $R^3$, $R^4$, $R^5$ and $R^6$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof. In another embodiment, $R^2$, $R^3$, $R^4$, $R^5$ and $R^6$ are hydrogen.

In one embodiment of the compound, L is selected from the group consisting of:

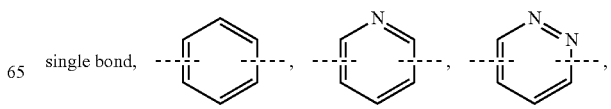

-continued
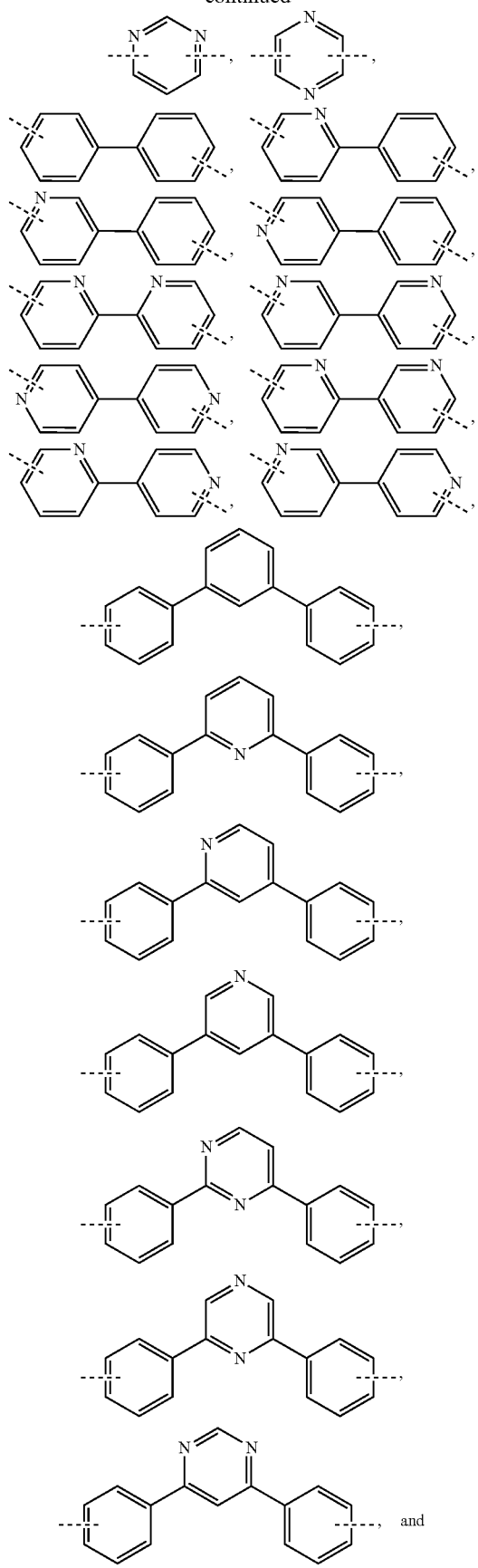
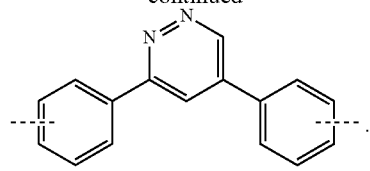
In one embodiment, L is preferably a single bond, phenyl, or pyridine.
In one embodiment of the compound, X is O. In another embodiment, X is S.
In one embodiment, the compound is selected from the group consisting of:
Compound 1-X
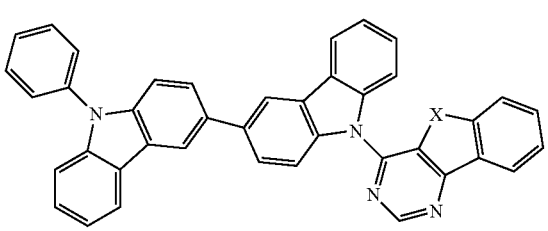
Compound 2-X
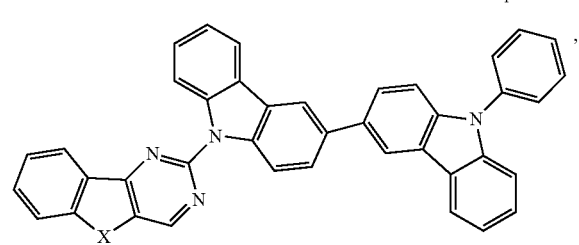
Compound 3-X
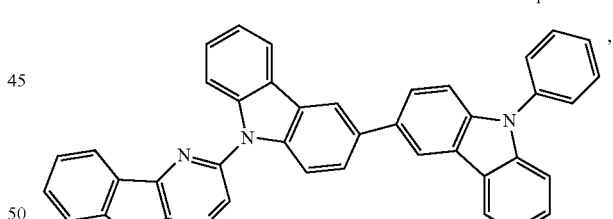
Compound 4-X
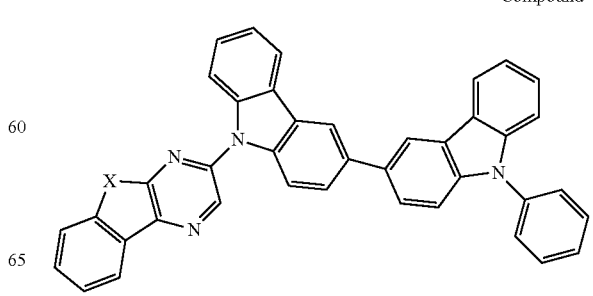

Compound 5-X
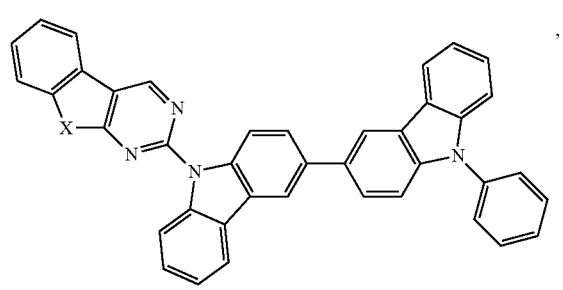
Compound 6-X
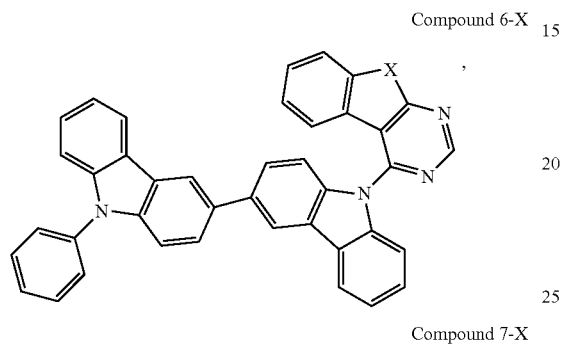
Compound 7-X
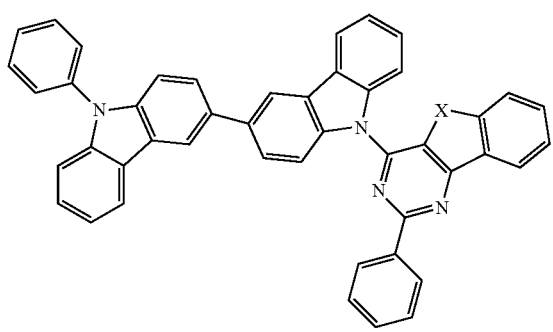
Compound 8-X
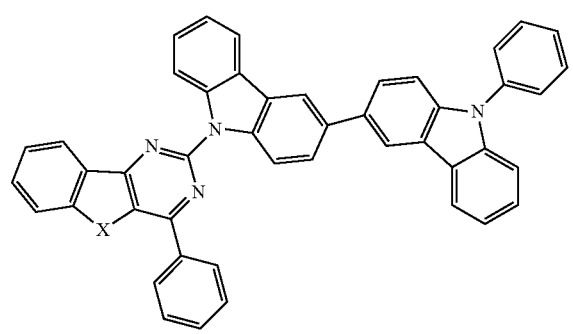
Compound 9-X
Compound 10-X
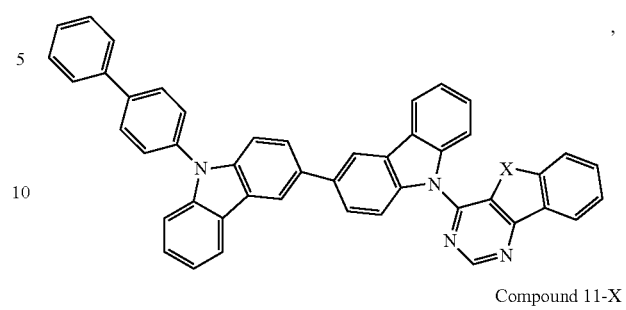
Compound 11-X
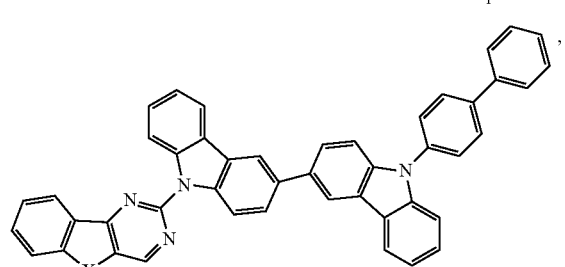
Compound 12-X
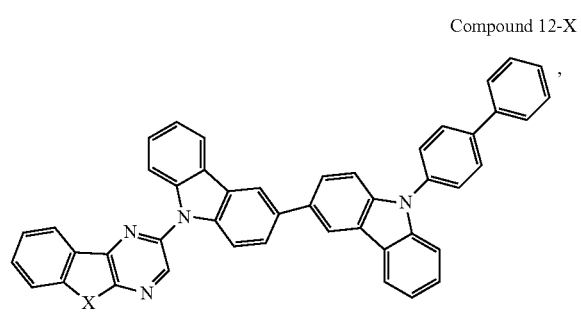
Compound 13-X
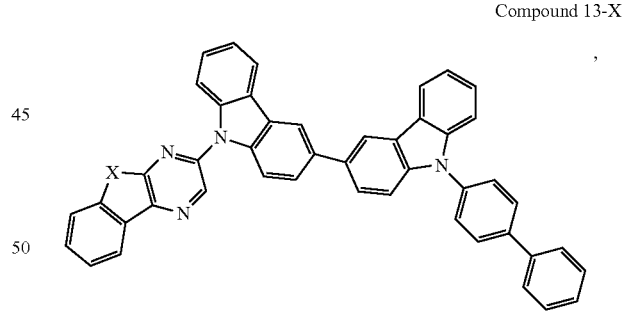
Compound 14-X
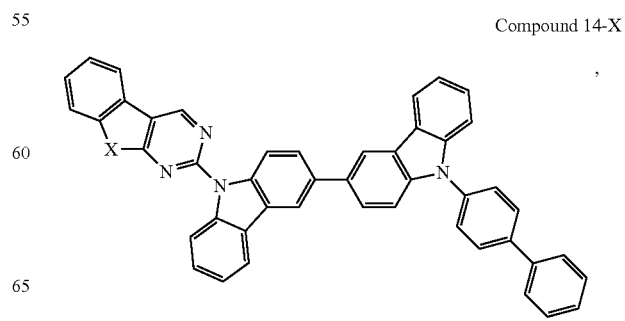

Compound 15-X
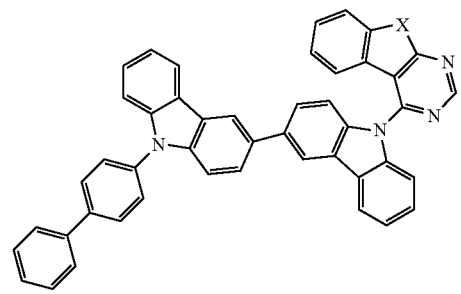
Compound 16-X
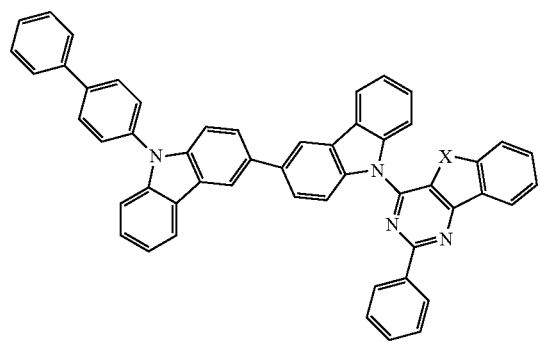
Compound 17-X
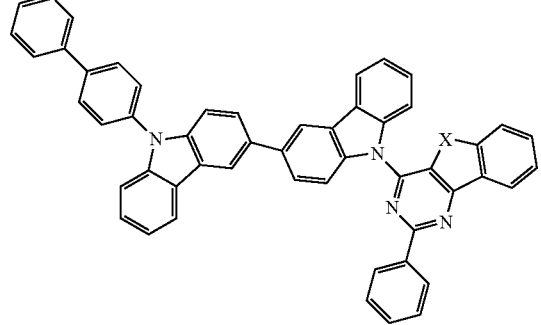
Compound 18-X
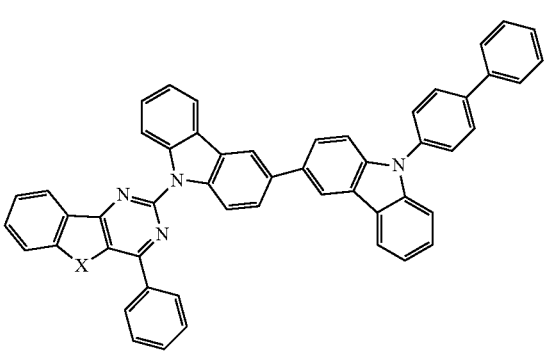
Compound 19-X
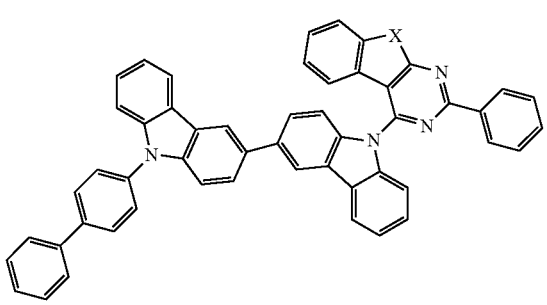
Compound 20-X
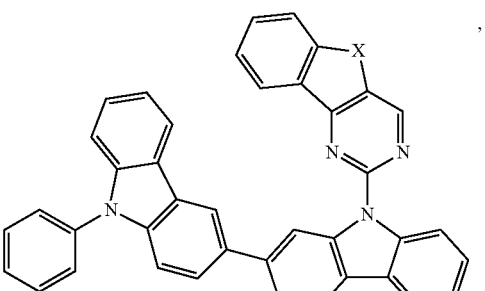
Compound 21-X
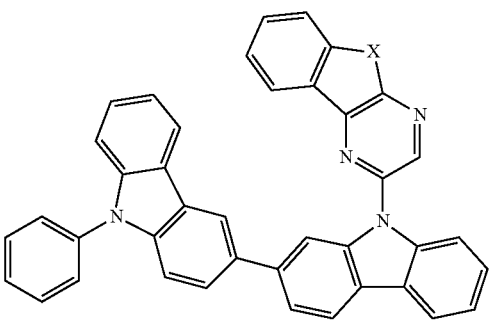
Compound 22-X
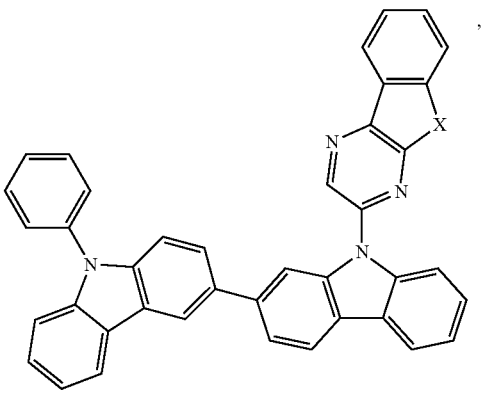
Compound 23-X
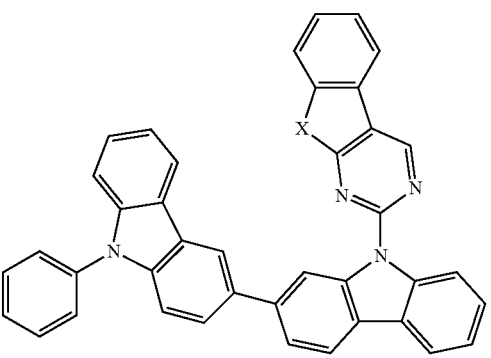

Compound 24-X
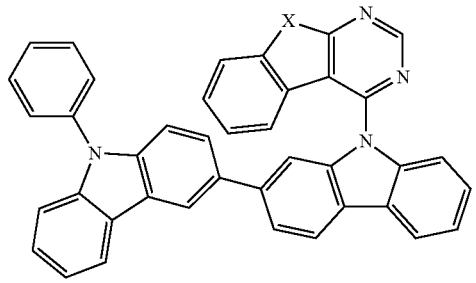
Compound 25-X
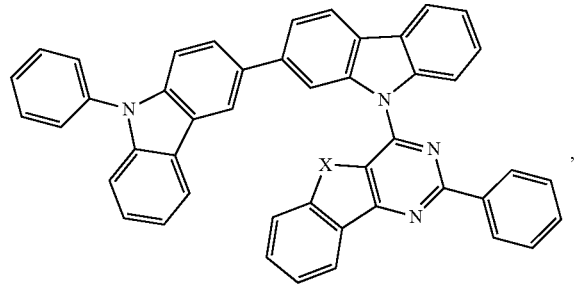
Compound 26-X
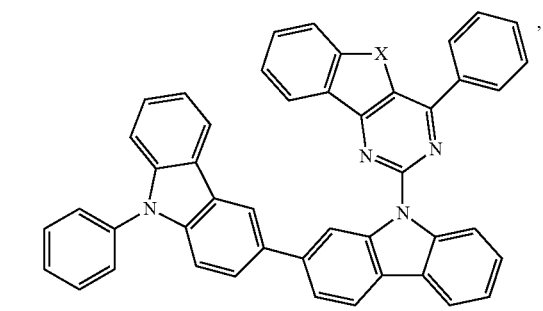
Compound 27-X
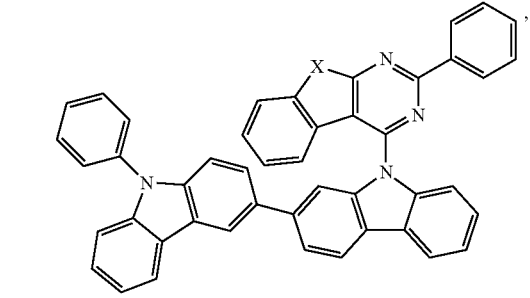
Compound 28-X
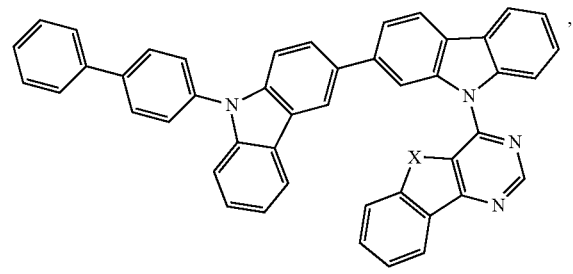
Compound 29-X
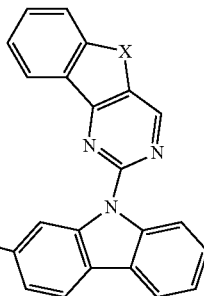
Compound 30-X
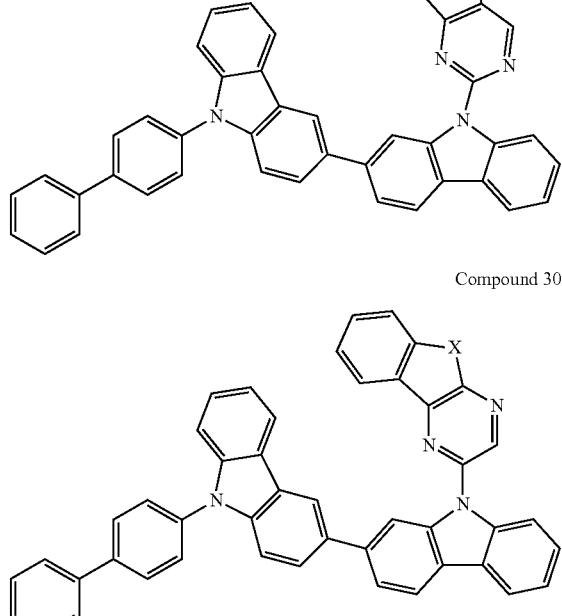
Compound 31-X
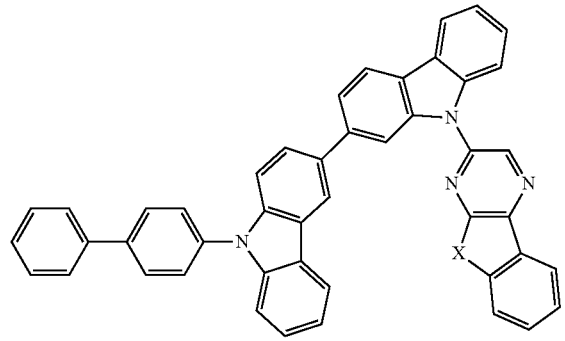
Compound 32-X
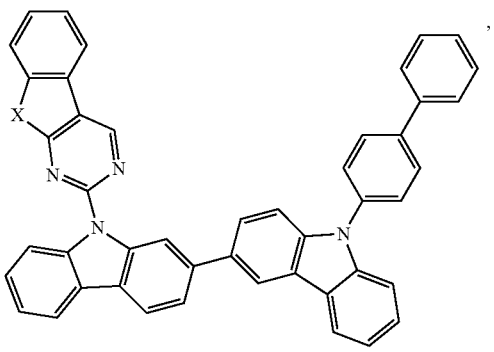

Compound 33-X
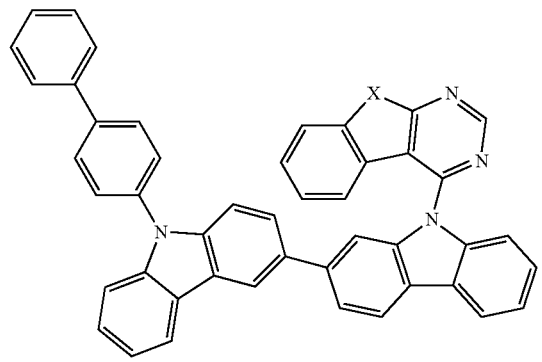
Compound 34-X
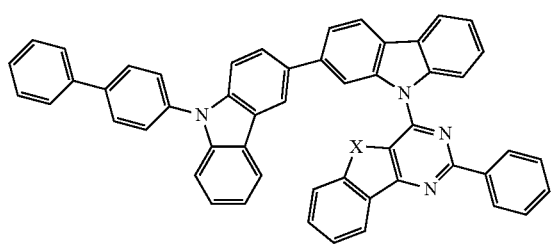
Compound 35-X
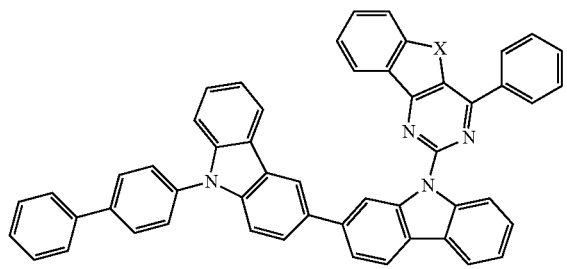
Compound 36-X
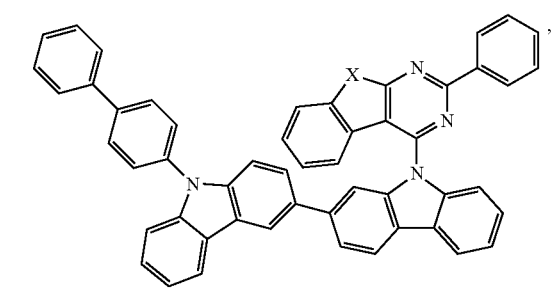
Compound 37-X
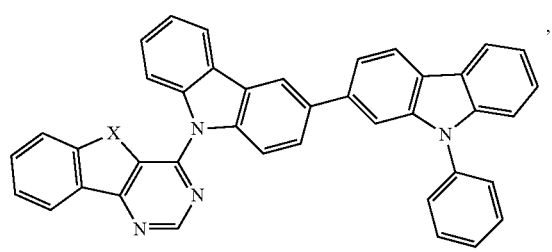
Compound 38-X
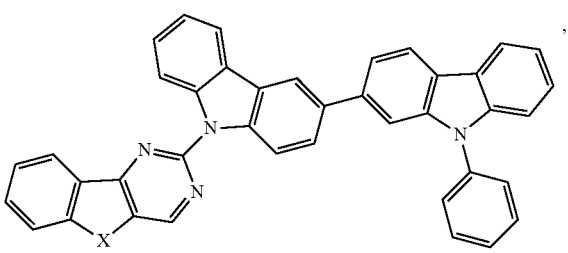
Compound 39-X
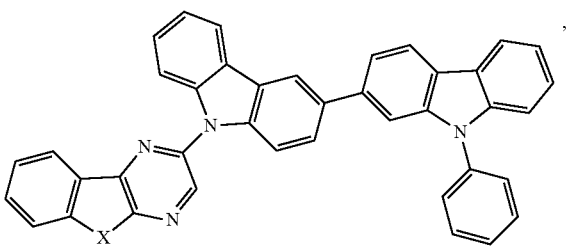
Compound 40-X
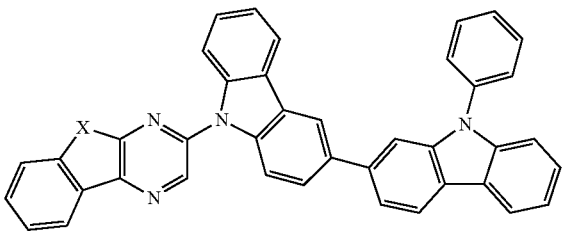
Compound 41-X
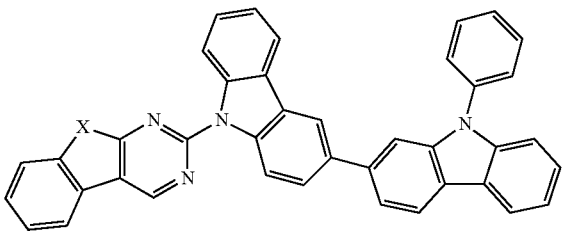
Compound 42-X
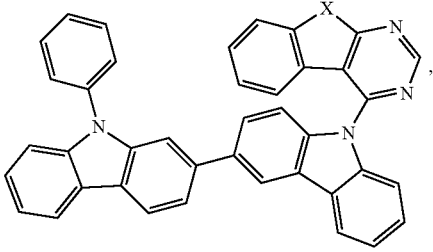

Compound 43-X
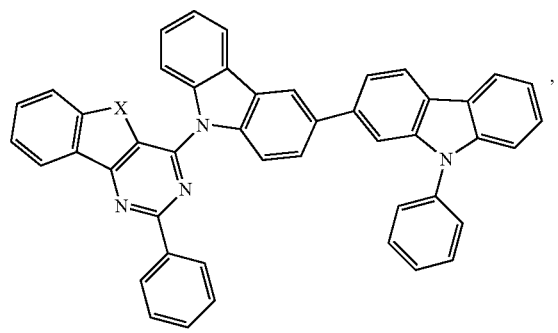
Compound 44-X
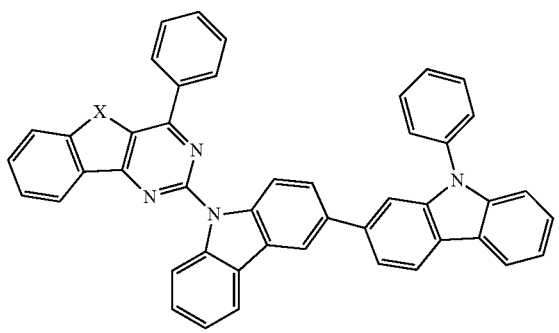
Compound 45-X
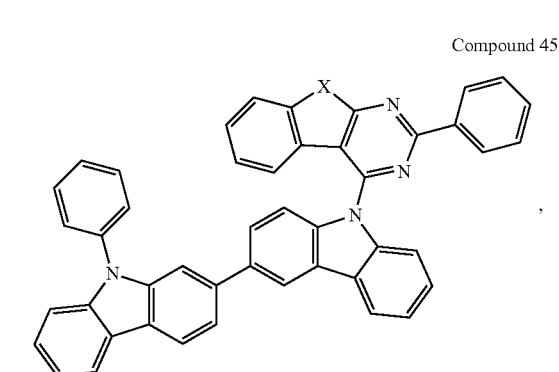
Compound 46-X
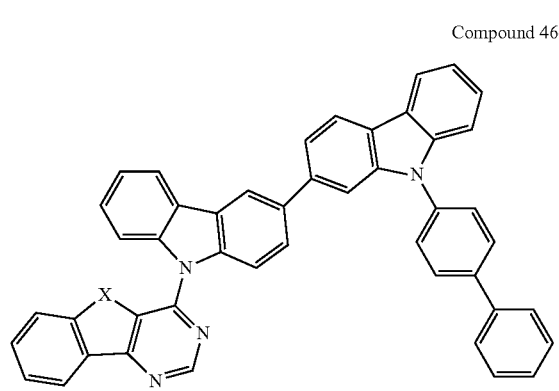
Compound 47-X
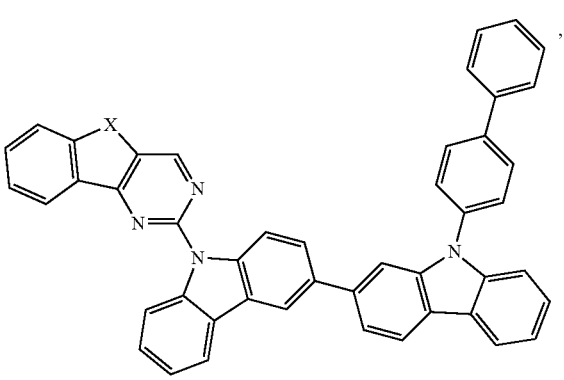
Compound 48-X
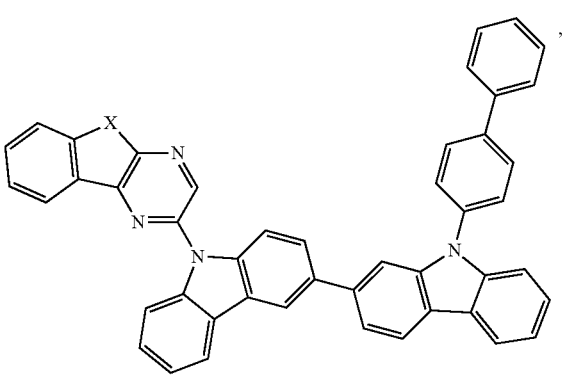
Compound 49-X
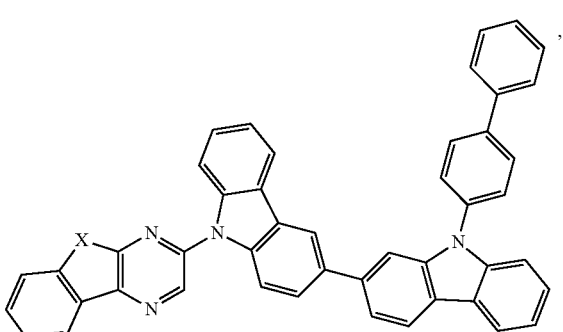
Compound 50-X
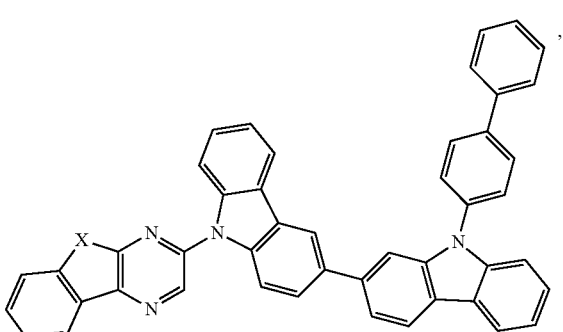

-continued
Compound 51-X
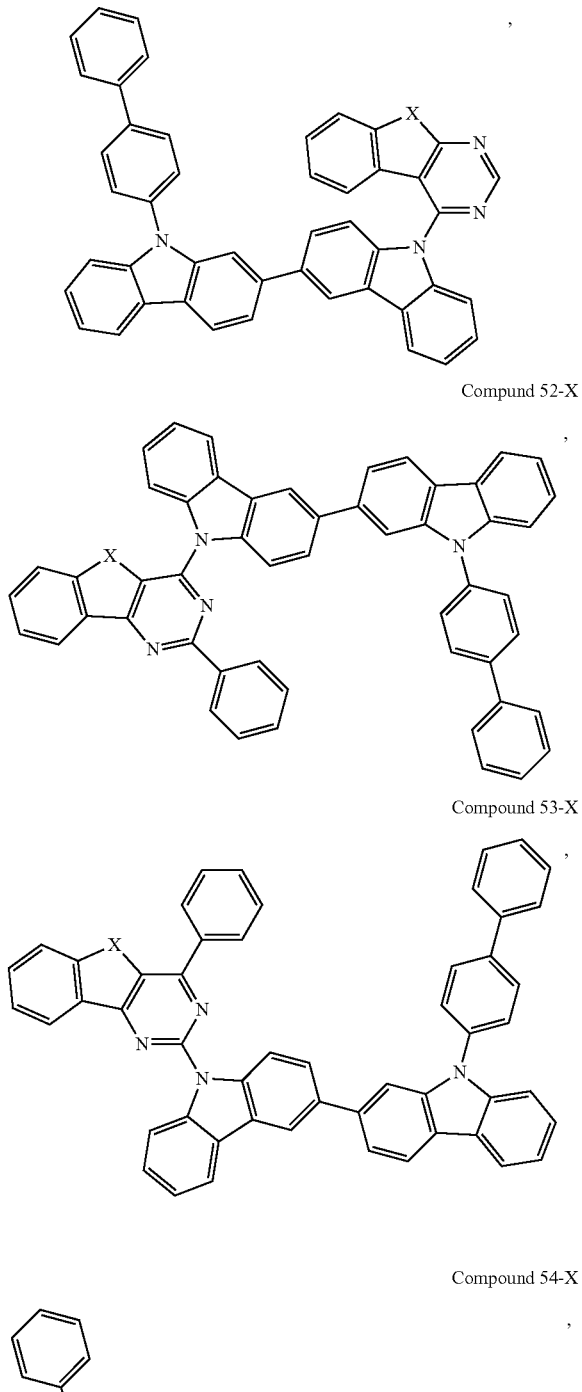
Compound 52-X
Compound 53-X
Compound 54-X
-continued
Compound 55-X
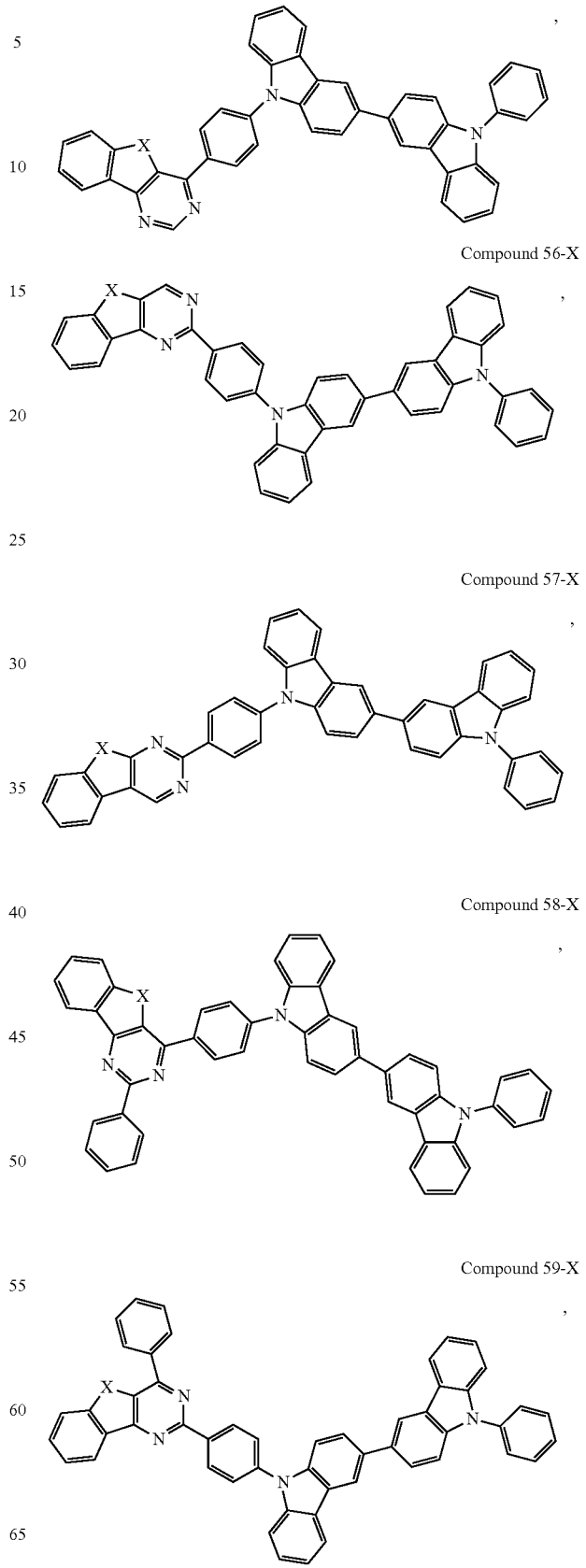
Compound 56-X
Compound 57-X
Compound 58-X
Compound 59-X Compound 60-X
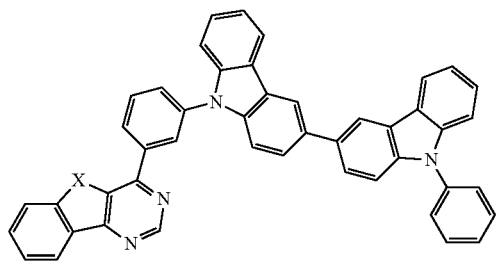
Compound 61-X
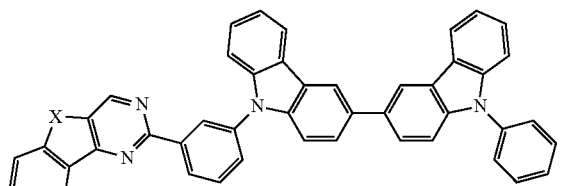
Compound 62-X
Compound 63-X
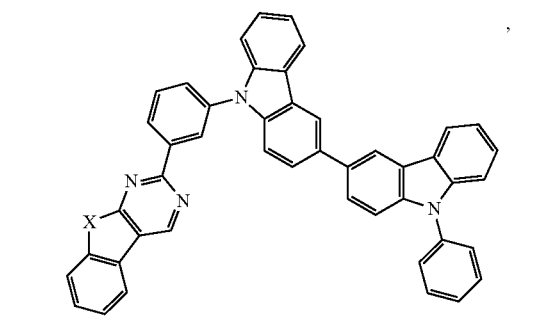
Compound 64-X
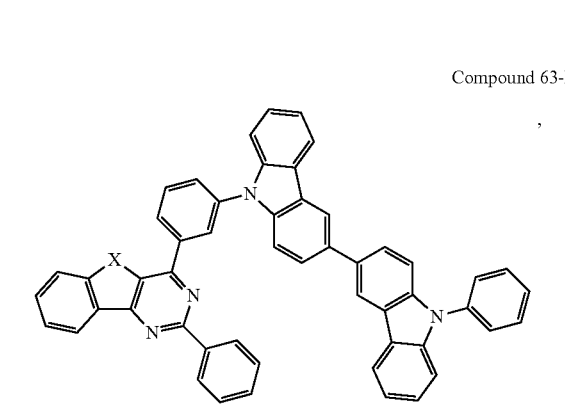
Compound 65-X
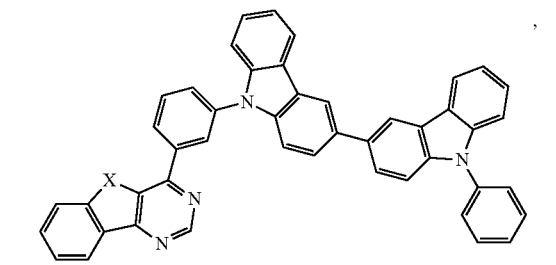
Compound 66-X
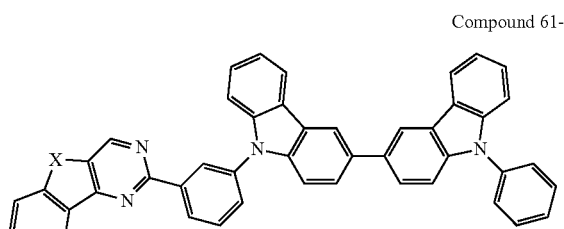
Compound 67-X
Compound 68-X
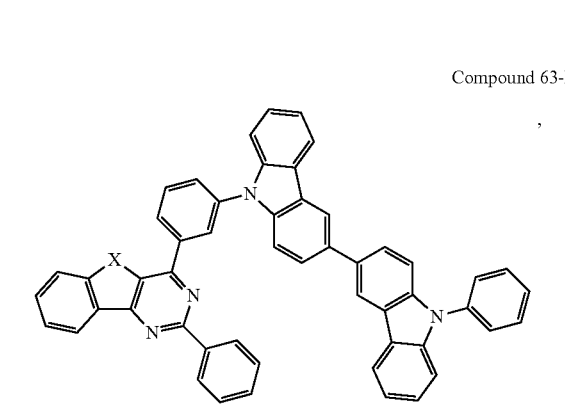
Compound 69-X
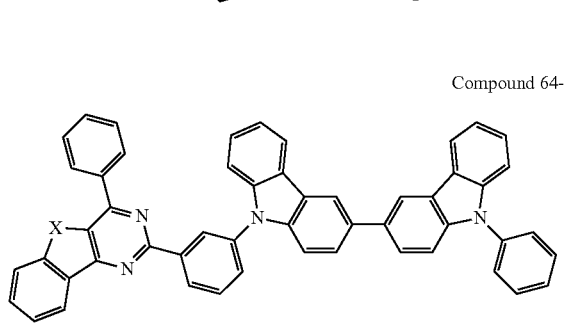

Compound 70-X
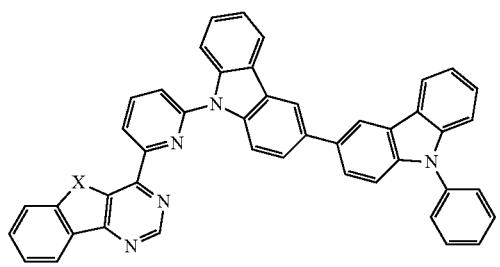
Compound 71-X
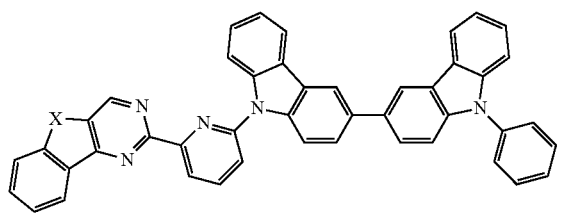
Compound 72-X
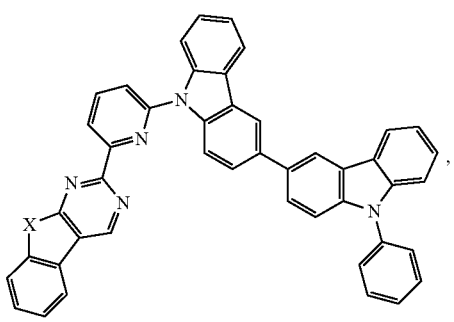
Compound 73-X
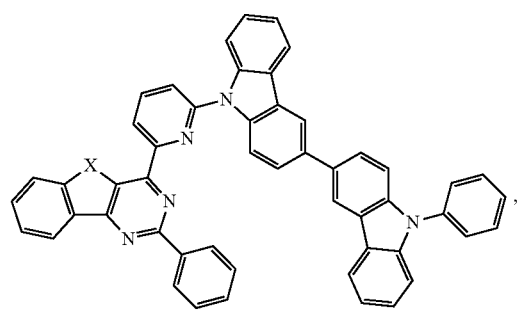
Compound 74-X
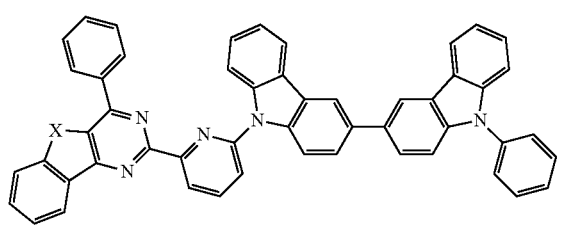
Compound 75-X
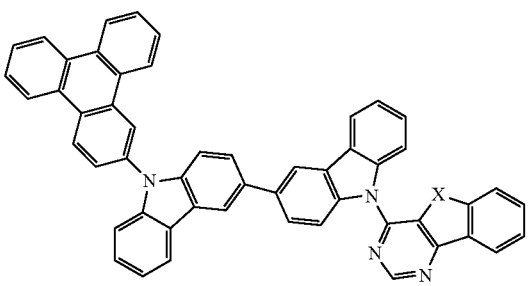
Compound 76-X
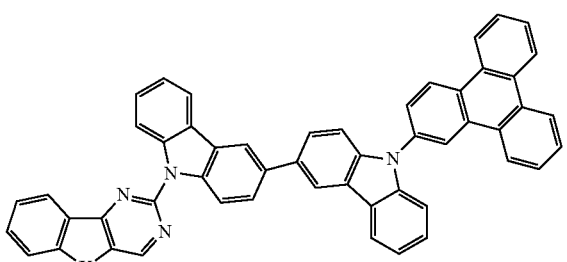
Compound 77-X
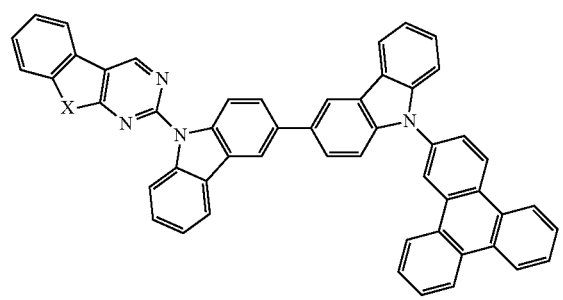
Compound 78-X
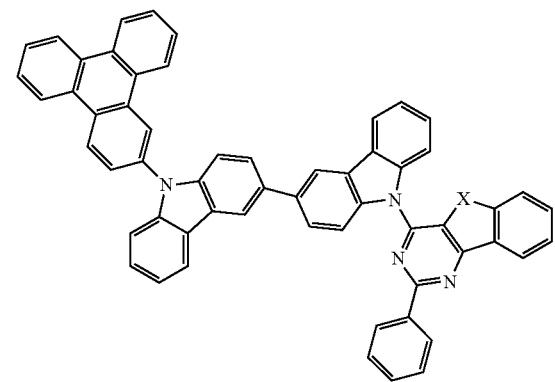

Compound 79-X
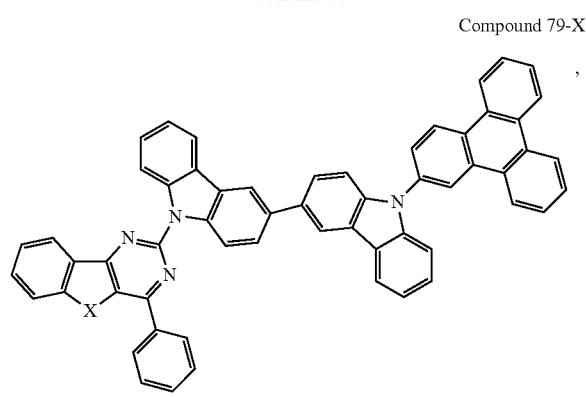
Compound 80-X
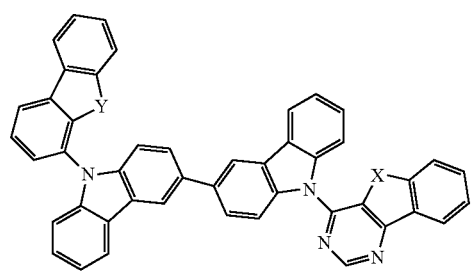
Compound 81-X
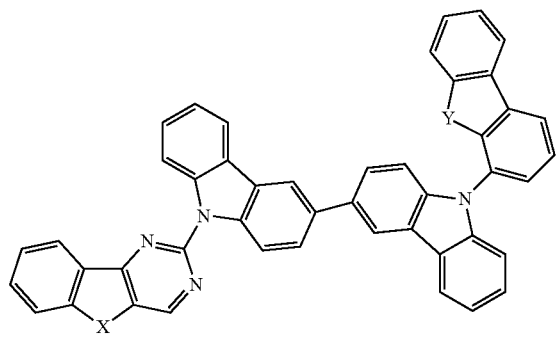
Compound 82-X
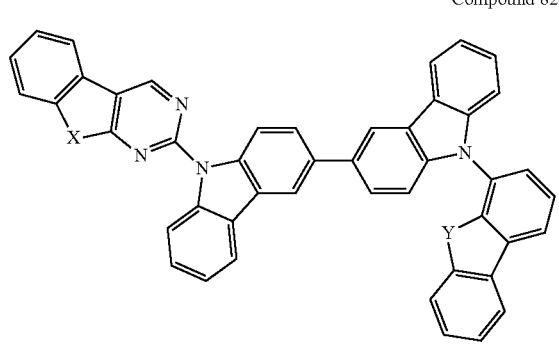
Compound 83-X
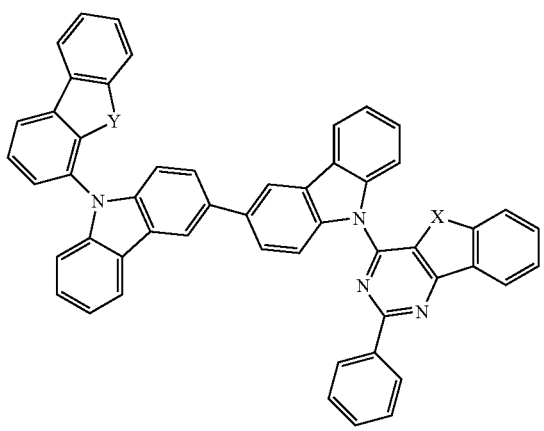
Compound 84-X
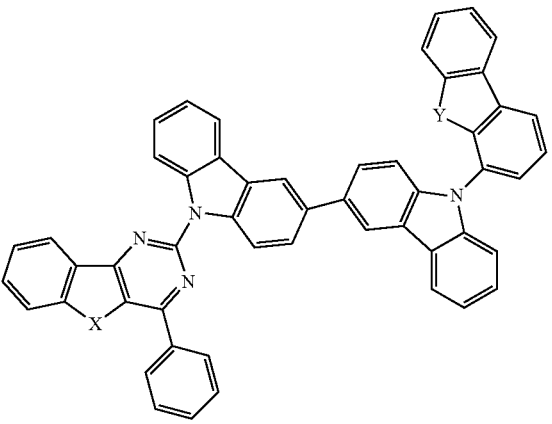
Compound 85-X
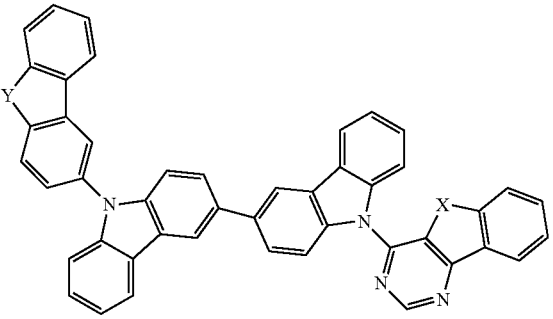
Compound 86-X
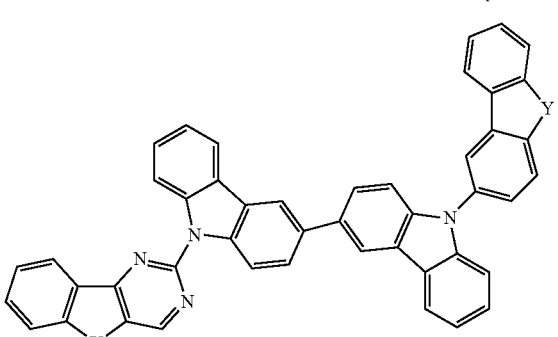

Compound 87-X
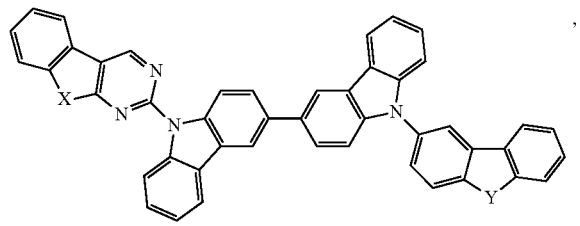
Compound 88-X
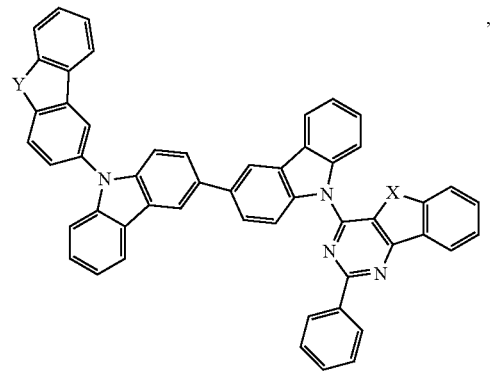
Compound 89-X
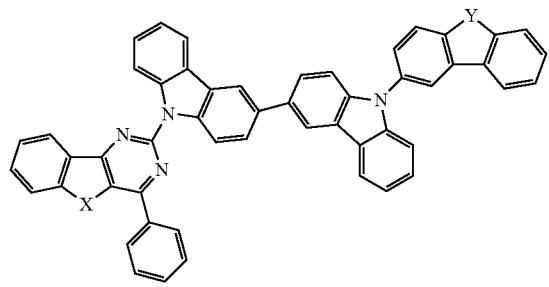
Compound 90-X
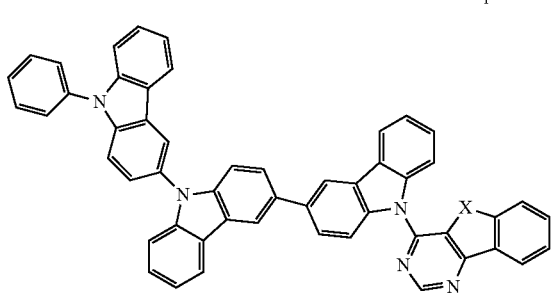
Compound 91-X
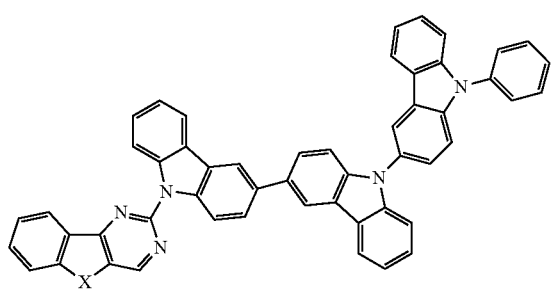
Compound 92-X
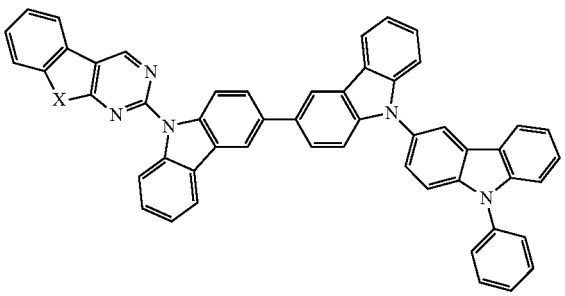
Compound 93-X
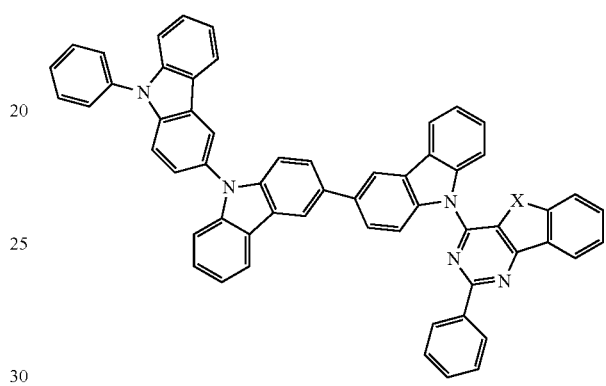
Compound 94-X
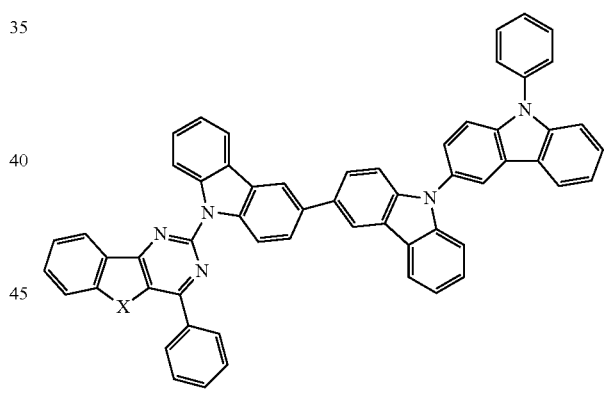
Compound 95-X
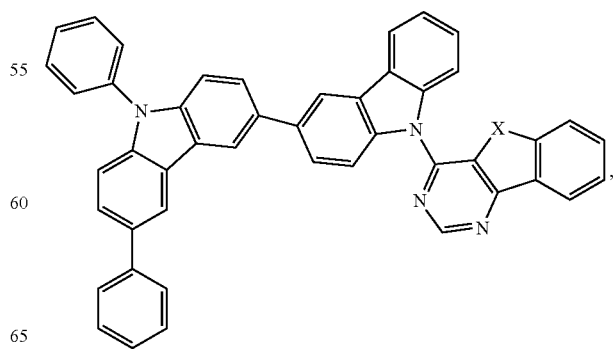

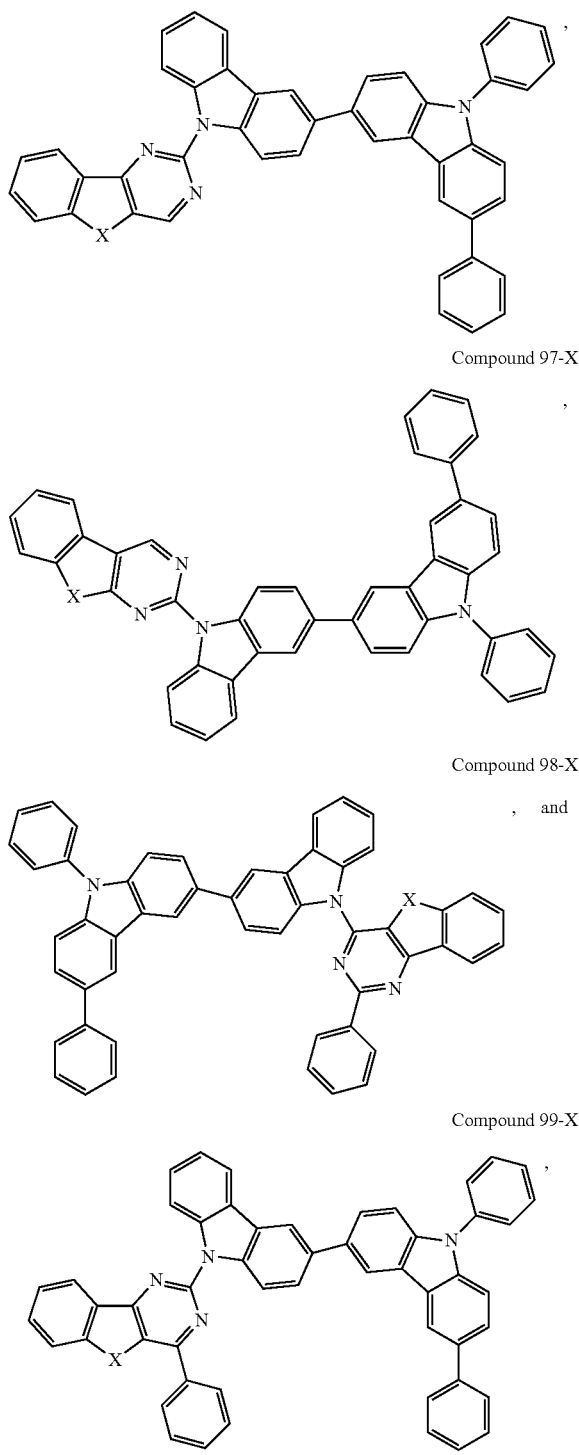

wherein Y in Compounds 80-X through 89-X is selected from the group consisting of O, S, and Se.

In one aspect, a formulation comprising a compound of Formula I is provided.

In one aspect, a first device comprising a first organic light emitting device is disclosed. The first organic light emitting device comprises an anode, a cathode, an organic layer, disposed between the anode and the cathode, wherein the organic layer further comprises a compound having a structure according to Formula I

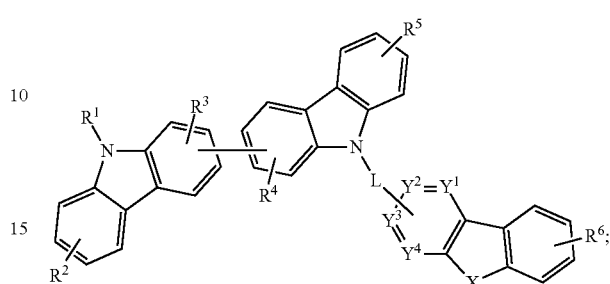

Formula I wherein $R^2$, $R^5$, and $R^6$ represent mono, di, tri, tetra substitutions or no substitution; wherein $R^3$, and $R^4$ represent mono, di, tri substitutions or no substitution; wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof; wherein X is selected from the group consisting of O, S, and Se; wherein $Y^1$, $Y^2$, $Y^3$, and $Y^4$ comprise C or N; wherein at least two of $Y^1$, $Y^2$, $Y^3$, and $Y^4$ are N; wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment of the first device, $R^1$ in the compound is aryl or heteroaryl. In one embodiment, $R^1$ is selected from the group consisting of phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof. In one embodiment, $R^2$, $R^3$, $R^4$, $R^5$ and $R^6$ are each independently selected from the group consisting of hydrogen, deuterium, aryl, heteroaryl and combinations thereof. In one embodiment, $R^2$, $R^3$, $R^4$, $R^5$ and $R^6$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof. In another embodiment, $R^2$, $R^3$, $R^4$, $R^5$ and $R^6$ are hydrogen.

In one embodiment, L in the compound is selected from the group consisting of:
single bond,

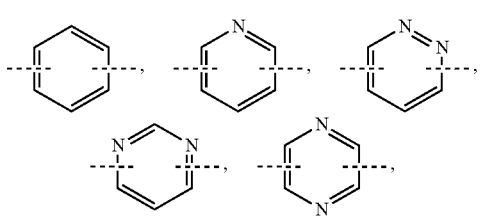

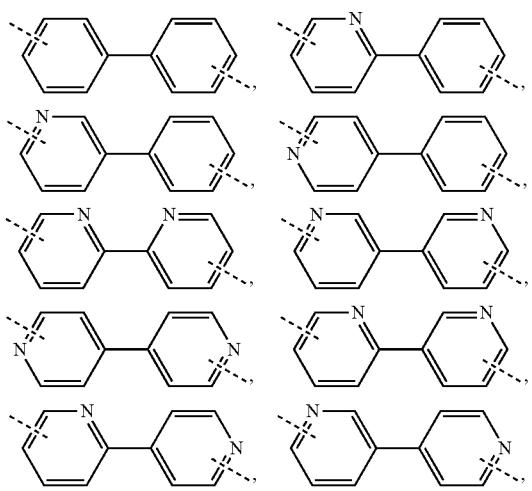

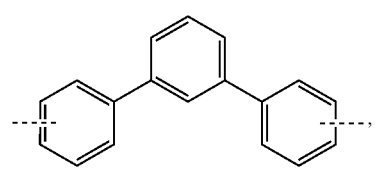

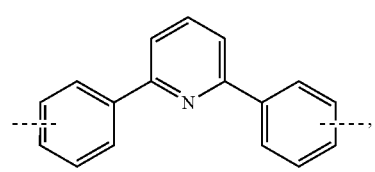

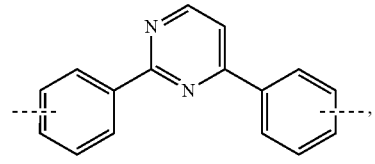

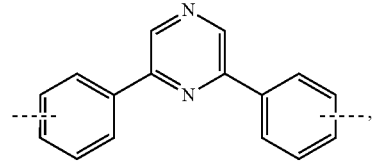

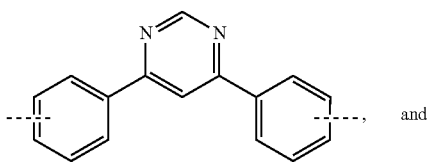, and

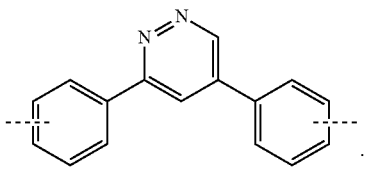

In one embodiment, L is preferably a single bond, phenyl, or pyridine.

In one embodiment of the compound, X is O. In another embodiment, X is S.

In one embodiment of the first device, the compound is selected from the group consisting of Compound 1-X through Compound 99-X, wherein Y in Compounds 80-X through 89-X is selected from the group consisting of O, S, and Se.

In one embodiment of the first device, the organic layer is an emissive layer and the compound having Formula I is a host. In one embodiment, the organic layer further comprises an emissive dopant. In one embodiment, the organic layer is a blocking layer and the compound having Formula I is a blocking material in the organic layer. In one embodiment, the organic layer is an electron transporting layer and the compound having Formula I is an electron transporting material in the organic layer. In a further embodiment, the emissive dopant is a transition metal complex having at least one ligand selected from the group consisting of:

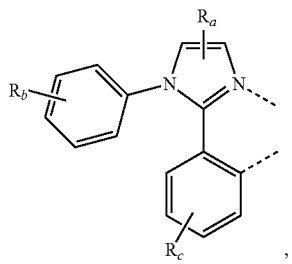

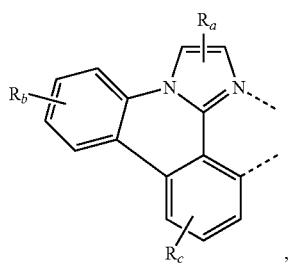

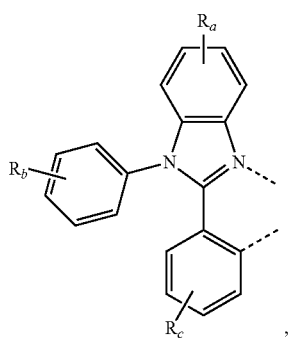

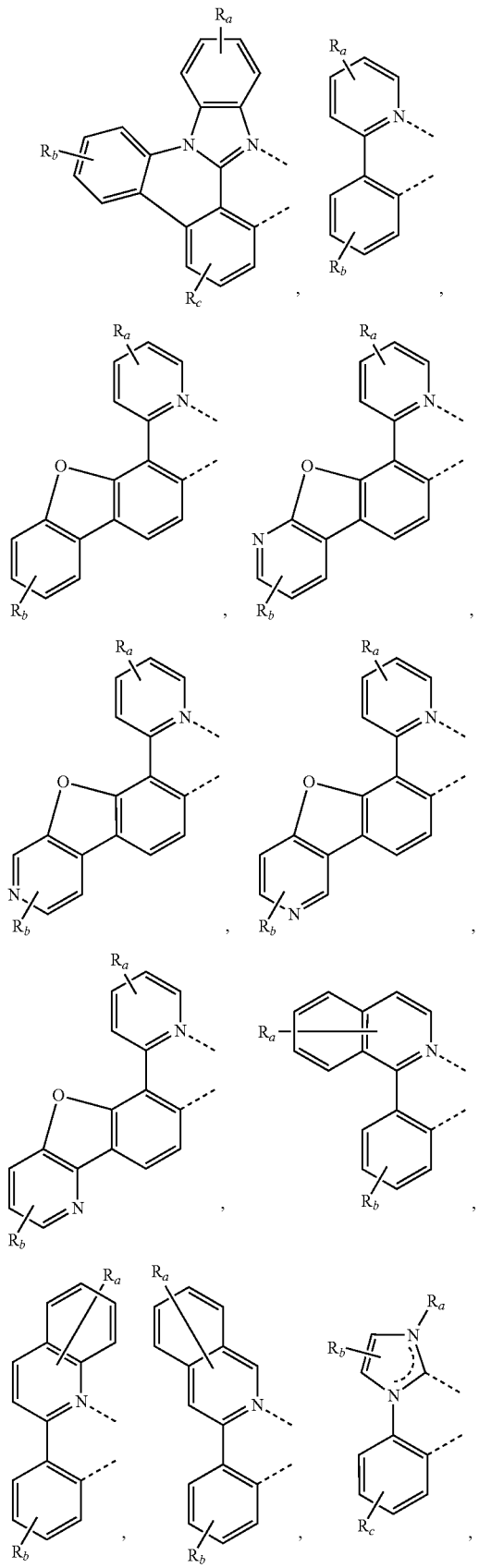
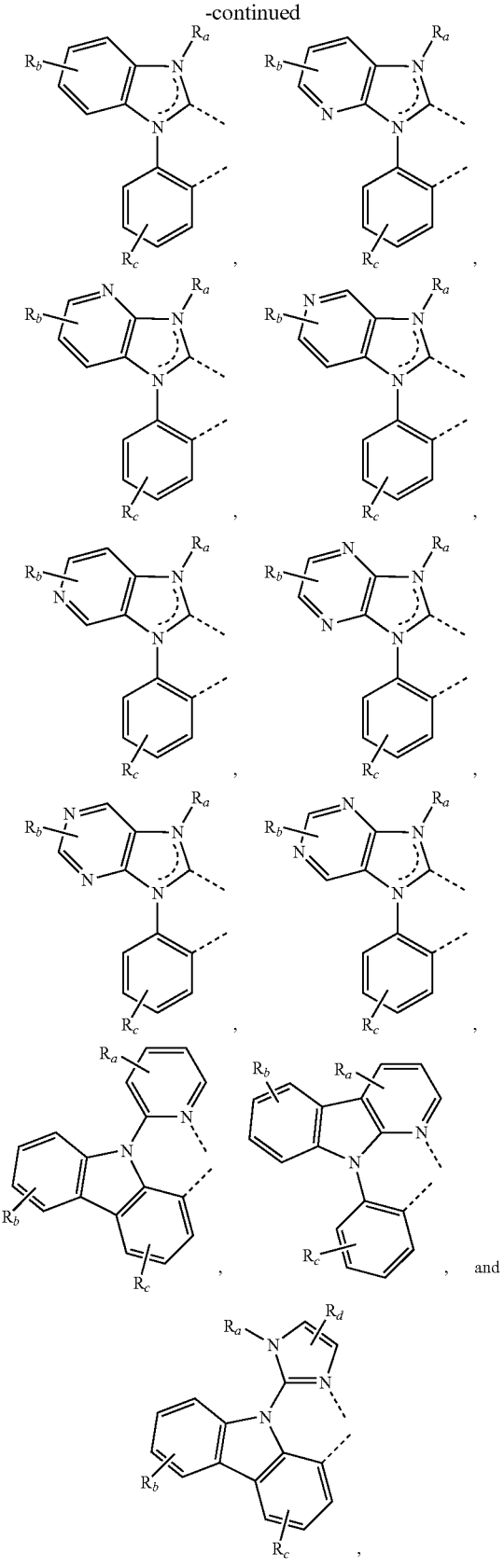
wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment, the first device is a consumer product. In one embodiment, the first device is an organic light-emitting device. In one embodiment, the first device comprises a lighting panel.

The compounds described in this disclosure were found to have surprising and unexpected properties when used as hosts in the emissive layer and/or blocking materials in PHOLEDs. The inventors discovered bicarbazole compounds with azaDBX having two nitrogens on the same ring showed improved results.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

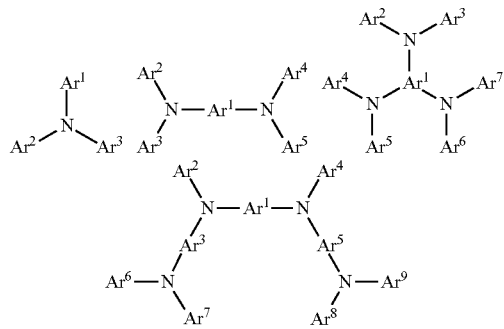

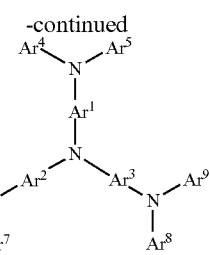

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

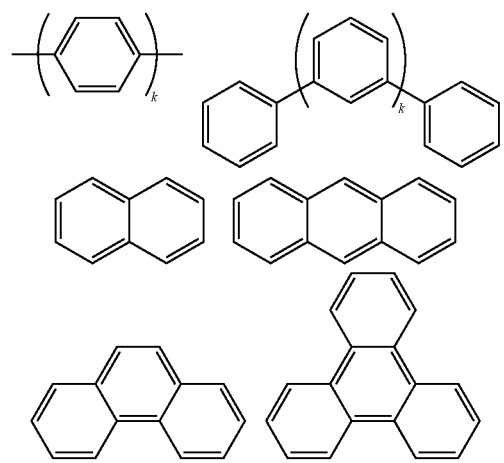

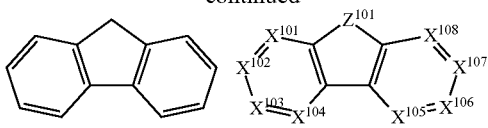

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

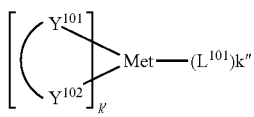

wherein Met is a metal; ($Y^{101}$-$Y^{102}$) is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criterion is satisfied.

Examples of metal complexes used as host are preferred to have the following general formula:

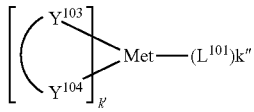

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

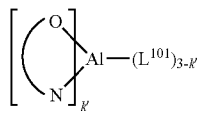 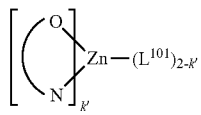

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

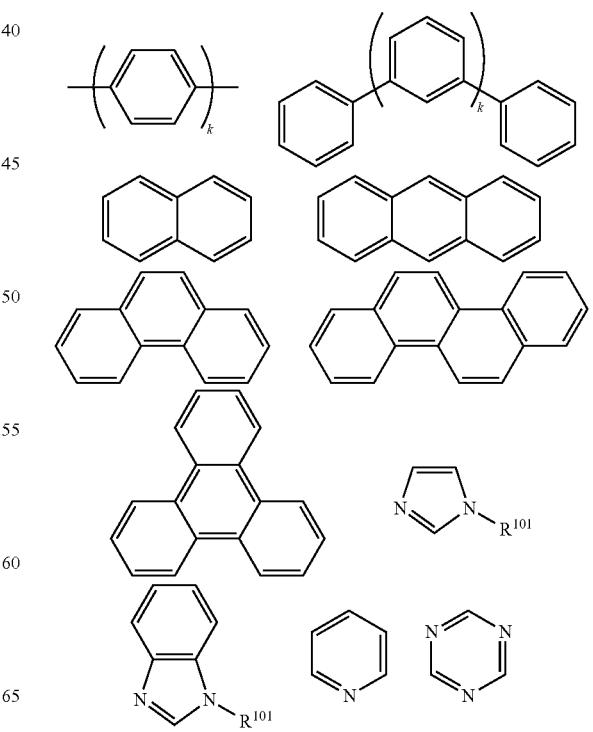

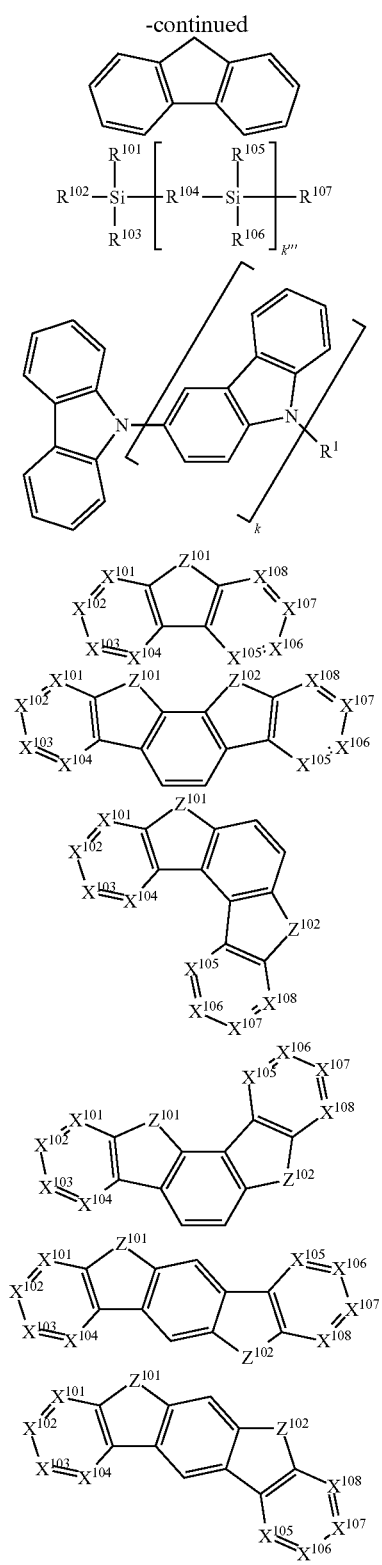

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

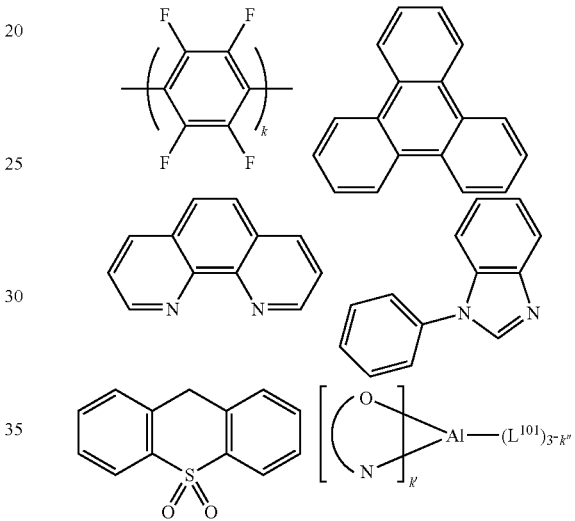

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

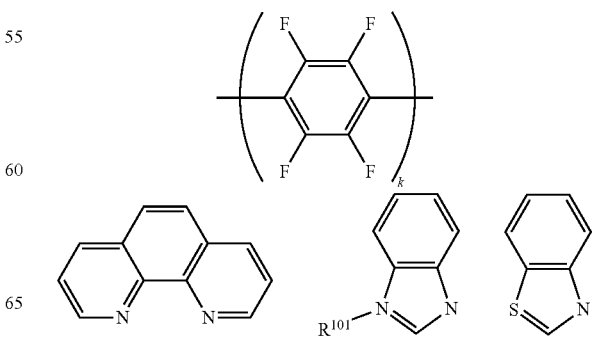

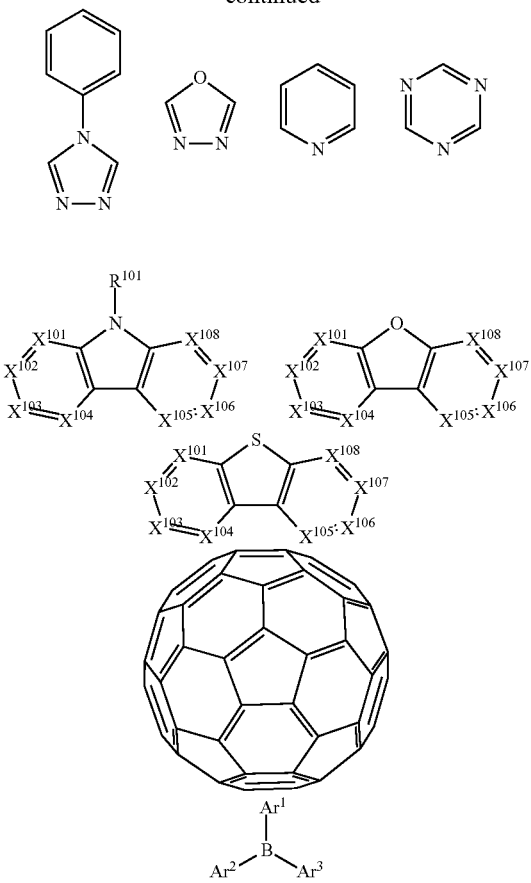

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

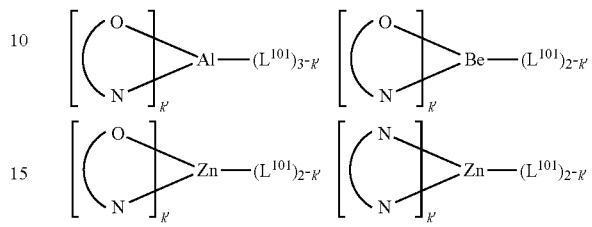

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table XXX below. Table XXX lists non-limiting classes of materials, non-limiting examples of compounds for each class, and references that disclose the materials.

TABLE 5

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 5-continued

| MATERIAL | EXAMPLES OF MATERIAL | PUBLICATIONS |
|---|---|---|
| Starburst triarylamines | 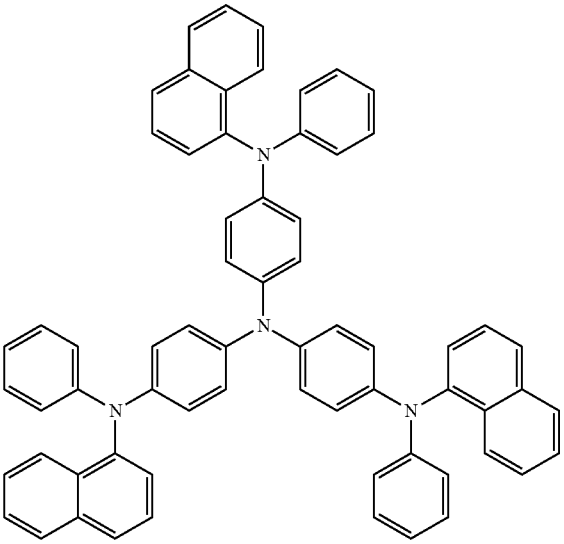 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin 72-74, 985 (1997) |
| $CF_x$ Fluorohydrocarbon polymer | $-\!\!+\!\!CH_xF_y\!\!+\!\!_n-$ | Appl. Phys. Lett. 78, 673 (2001) |
| Conducting polymers (e.g., PEDOT:PSS, polyaniline, polypthiophene) | 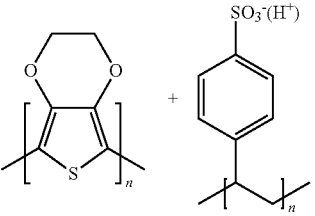 | Synth. Met. 87, 171 (1997) WO2007002683 |
| Phosphonic acid and silane SAMs | 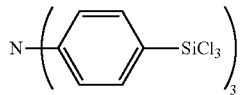 | US20030162053 |
| Triarylamine or polythiophene polymers with conductivity dopants | 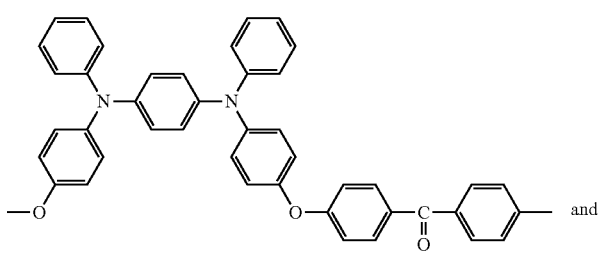 and 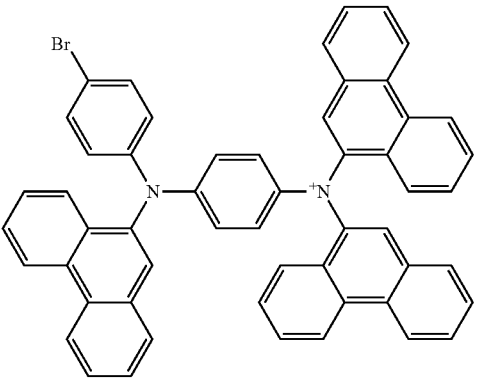 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | EP1725079A1 |

TABLE 5-continued

| MATERIAL | EXAMPLES OF MATERIAL | PUBLICATIONS |
| --- | --- | --- |
| Organic compounds with conductive inorganic compounds, such as molybdenum and tungsten oxides | [structure] + MoO$_x$ | US20050123751<br>SID Symposium Digest, 37, 923 (2006)<br>WO2009018009 |
| n-type semiconducting organic complexes | | US20020158242 |
| Metal organometallic complexes | | US20060240279 |
| Cross-linkable compounds | | US20080220265 |
| Polythiophene based polymers and copolymers | [structure] | WO 2011075644<br>EP2350216 |

Hole transporting materials

| Triarylamines (e.g., TPD, α-NPD) | [structure] | Appl. Phys. Lett. 51, 913 (1987) |
| --- | --- | --- |

TABLE 5-continued
| MATERIAL | EXAMPLES OF MATERIAL | PUBLICATIONS |
|---|---|---|
| | 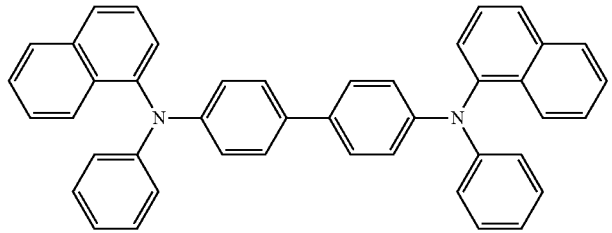 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 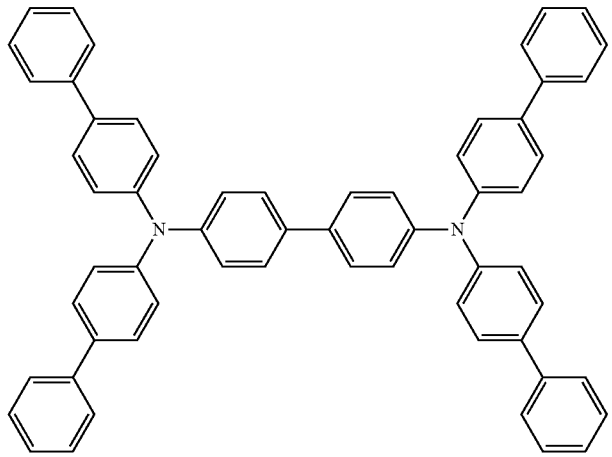 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 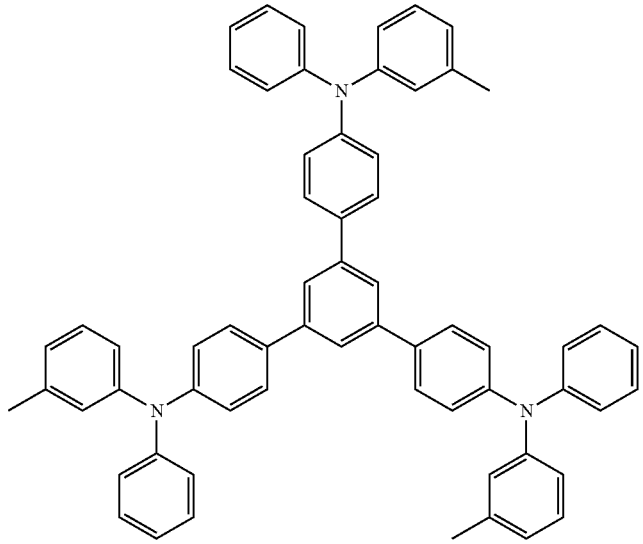 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 5-continued

| MATERIAL | EXAMPLES OF MATERIAL | PUBLICATIONS |
| --- | --- | --- |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 5-continued
| MATERIAL | EXAMPLES OF MATERIAL | PUBLICATIONS |
| --- | --- | --- |
| Triarylamine with (di)benzothiophene/ (di)benzofuran | 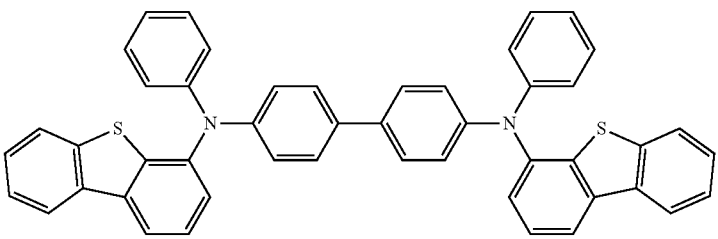 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolcarbazoles | 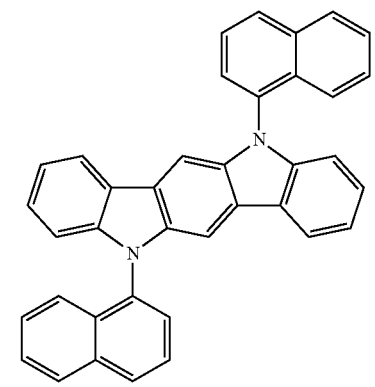 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 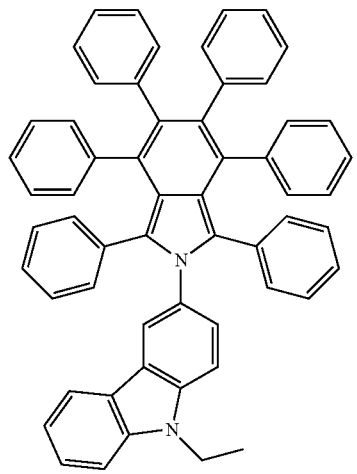 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 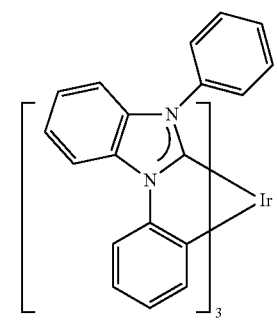 | US20080018221 |

TABLE 5-continued

| MATERIAL | EXAMPLES OF MATERIAL | PUBLICATIONS |
|---|---|---|
| | Phosphorescent OLED host materials Red hosts | |
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 5-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065, |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |

TABLE 5-continued
| MATERIAL | EXAMPLES OF MATERIAL | PUBLICATIONS |
|---|---|---|
| Aryltriphenylene compounds | 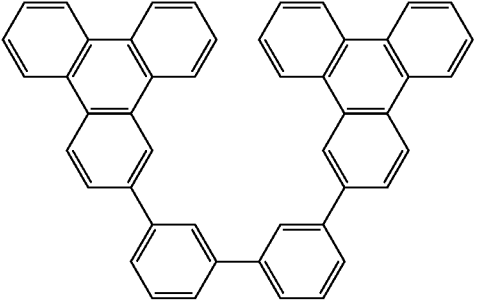 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 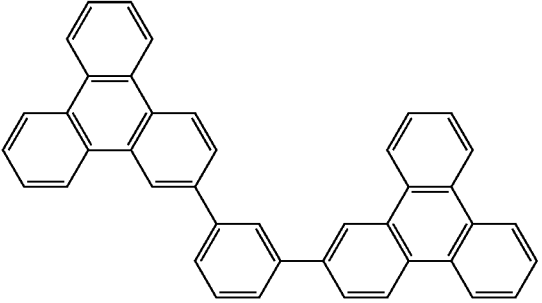 [SMILES: c1cc(-c2ccc3c4ccccc4c4ccccc4c3c2)cc(-c2ccc3c4ccccc4c4ccccc4c3c2)c1] | US20060280965 |
| | 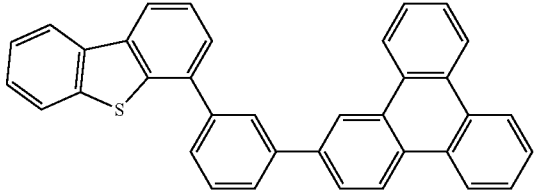 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 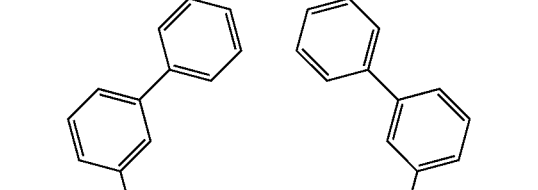 | US20090309488<br>US20090302743<br>US20100012931 |
| Donor acceptor type molecules | 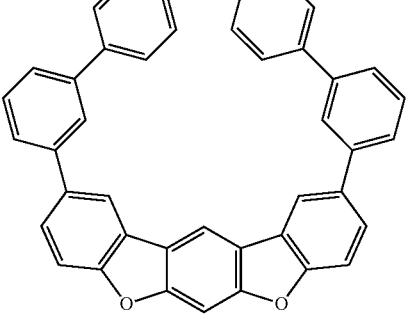 | WO2008056746 |

TABLE 5-continued
| MATERIAL | EXAMPLES OF MATERIAL | PUBLICATIONS |
|---|---|---|
| | 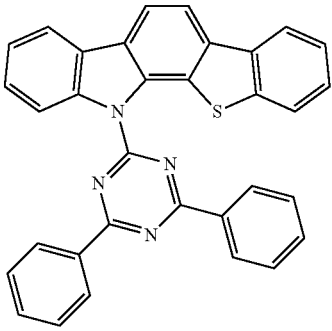 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/ DBF | 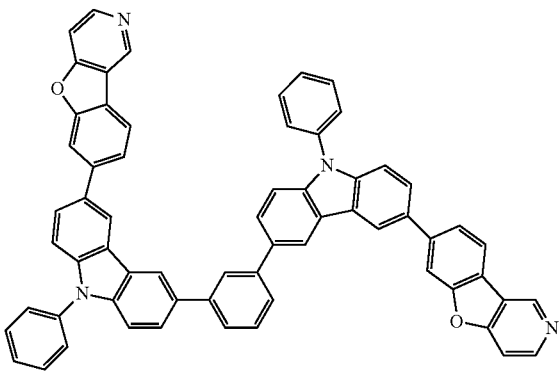 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 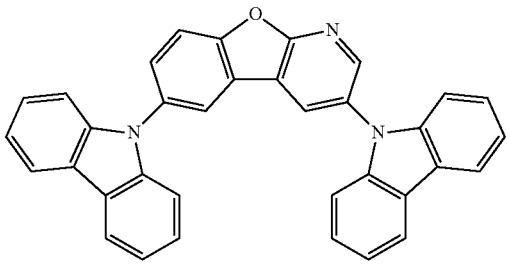 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 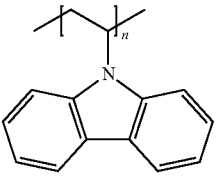 | Appl. Phys. Lett. 77, 2280 (2000) |
| Spirofluorene compounds | 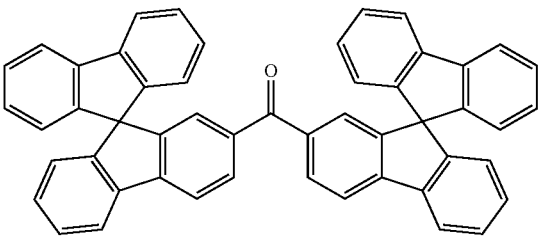 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 5-continued

| MATERIAL | EXAMPLES OF MATERIAL | PUBLICATIONS |
|---|---|---|
| Metal phneoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 5-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 5-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 5-continued

| MATERIAL | EXAMPLES OF MATERIAL | PUBLICATIONS |
| --- | --- | --- |
|  |  | WO2009086028 |
|  |  | US20090030202, US20090017330 |
|  |  | US20100084966 |
| Silicon aryl compounds |  | US20050238919 |
|  |  | WO2009003898 |
| Silicon/Germanium aryl compounds |  | EP2034538A |

TABLE 5-continued

| MATERIAL | EXAMPLES OF MATERIAL | PUBLICATIONS |
| --- | --- | --- |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
| --- | --- | --- |
| Heavy metal porphyrins (e.g., PtOEP) | | Nature 395, 151 (1998) |
| Iridium (III) organometallic complexes | | Appl. Phys. Lett. 78, 1622 (2001) |

TABLE 5-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 5-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE 5-continued
| MATERIAL | EXAMPLES OF MATERIAL | PUBLICATIONS |
|---|---|---|
| | 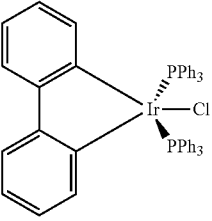 | U.S. Pat. No. 7,232,618 |
| Platinum(II) organometallic complexes | 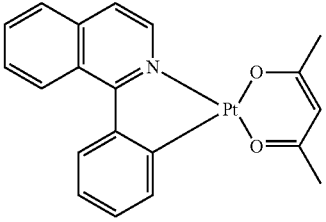 | WO2003040257 |
| | 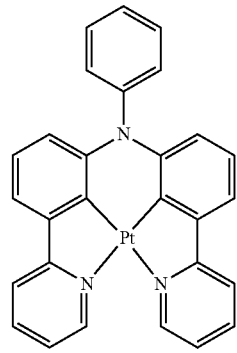 | US20070103060 |
| Osminum(III) complexes | 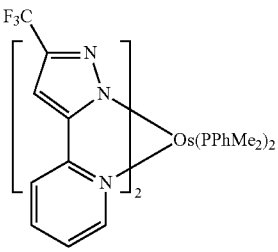 | Chem. Mater. 17, 3532 (2005) |
| Ruthenium(II) complexes | 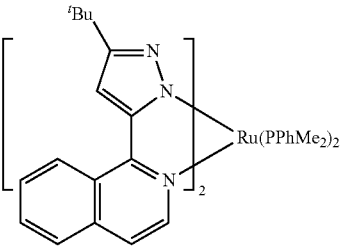 | Adv. Mater. 17, 1059 (2005) |

TABLE 5-continued
| MATERIAL | EXAMPLES OF MATERIAL | PUBLICATIONS |
|---|---|---|
| Rhenium (I), (II) and (III) complexes | | US20050244673 |
Green dopants
| | | |
|---|---|---|
| Iridium(III) organometallic complexes | 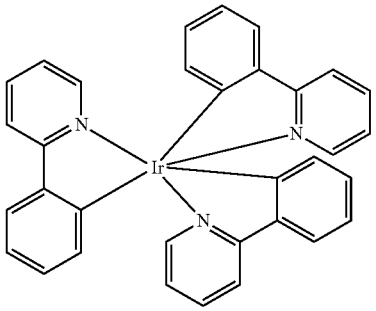<br>and its derivatives | Inorg. Chem. 40, 1704 (2001) |
| | 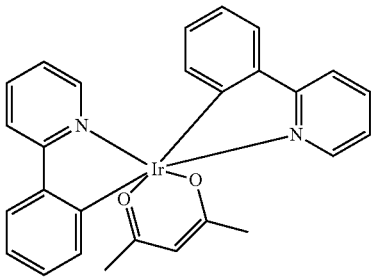 | US20020034656 |
| | 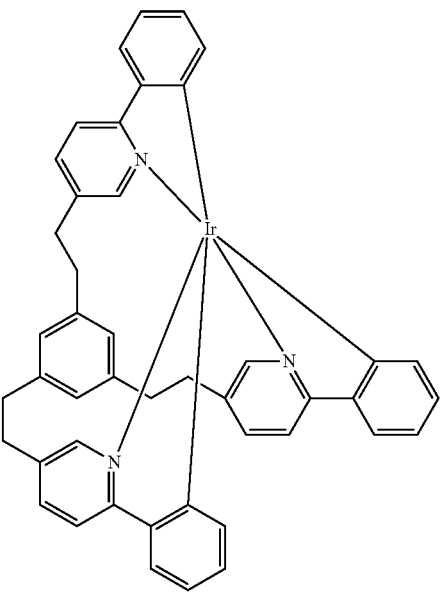 | U.S. Pat. No. 7,332,232<br><br>US20090108737 |

TABLE 5-continued

| MATERIAL | EXAMPLES OF MATERIAL | PUBLICATIONS |
| --- | --- | --- |
| | | WO2010028151 |
| | | EP1841834B |
| | | US20060127696 |
| | | US20090039776 |
| | | U.S. Pat. No. 6,921,915 |

TABLE 5-continued
| MATERIAL | EXAMPLES OF MATERIAL | PUBLICATIONS |
|---|---|---|
| | 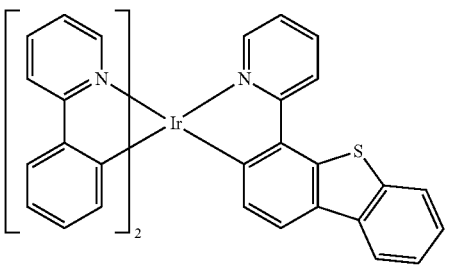 | US20100244004 |
| | 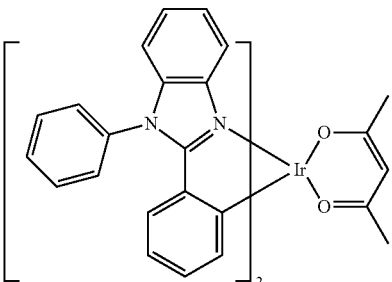 | U.S. Pat. No. 6,687,266 |
| | 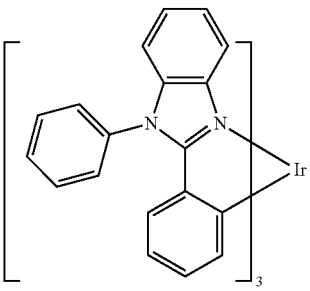 | Chem. Mater. 16, 2480 (2004) |
| | 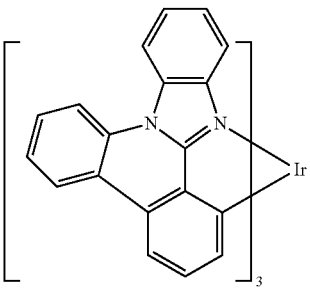 | US20070190359 |
| | 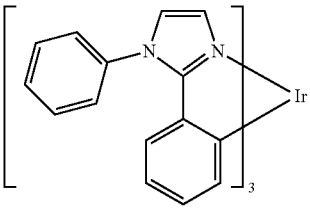 | US 20060008670<br>JP2007123392 |
| | 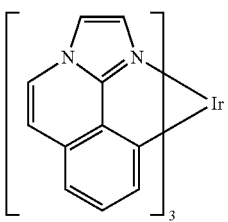 | WO2010086089,<br>WO2011044988 |

TABLE 5-continued
| MATERIAL | EXAMPLES OF MATERIAL | PUBLICATIONS |
|---|---|---|
| | 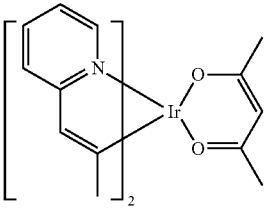 | Adv. Mater. 16, 2003 (2004) |
| | 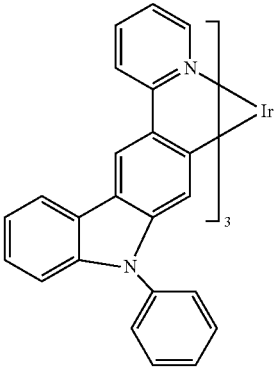 | Angew. Chem. Int. Ed. 2006, 45, 7800 |
| | 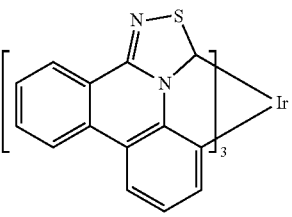 | WO2009050290 |
| | 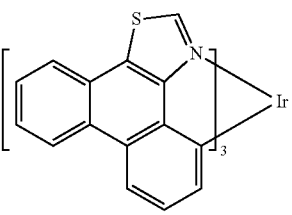 | US20090165846 |
| | 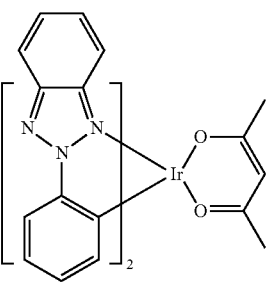 | US20080015355 |
| | 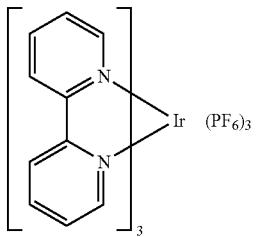 | US20010015432 |

TABLE 5-continued

| MATERIAL | EXAMPLES OF MATERIAL | PUBLICATIONS |
|---|---|---|
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |

TABLE 5-continued

| MATERIAL | EXAMPLES OF MATERIAL | PUBLICATIONS |
| --- | --- | --- |
| | | WO2002015645 |
| | | US20060263635 |
| | | US20060182992<br>US20070103060 |
| Cu complexes | | WO2009000673 |

TABLE 5-continued

| MATERIAL | EXAMPLES OF MATERIAL | PUBLICATIONS |
|---|---|---|
| | (Cu dimer complex with iBu₂P and N ligands) | US20070111026 |
| Gold complexes | (Au complex with phenylpyridine and alkynyl-triphenylamine) | Chem. Commun. 2906 (2005) |
| Rhenium(III) complexes | (Re complex with bis(trifluoromethyl)pyrazole, CO ligands, and biphenyl) | Inorg. Chem. 42, 1248 (2003) |
| Osmium(II) complexes | | U.S. Pat. No. 7,279,704 |
| Deuterated organometallic complexes | | US20030138657 |
| Organometallic complexes with two or more metal centers | (Pr dimer complex with difluorophenylpyridine and S bridges) | US20030152802<br><br>U.S. Pat. No. 7,090,928 |

US 9,553,274 B2
93 94
TABLE 5-continued
| MATERIAL | EXAMPLES OF MATERIAL | PUBLICATIONS |
|---|---|---|
| | Blue dopants | |
| Iridium(III) organometallic complexes | 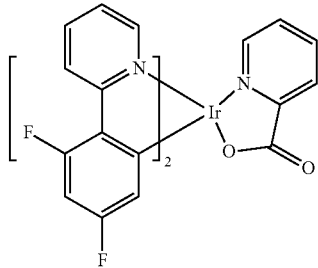 | WO2002002714 |
| | 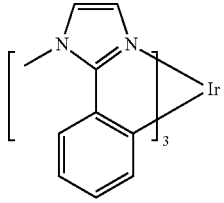 | WO2006009024 |
| | 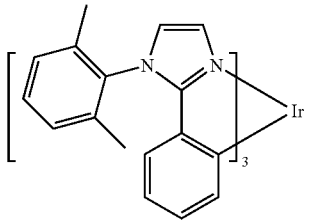 | US20060251923<br>US20110057559<br>US20110204333 |
| | 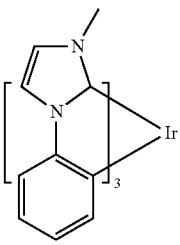 | U.S. Pat. No. 7,393,599,<br>WO2006056418,<br>US20050260441,<br>WO2005019373 |
| | 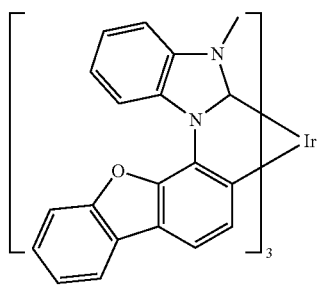 | U.S. Pat. No. 7,534,505 |

TABLE 5-continued

| MATERIAL | EXAMPLES OF MATERIAL | PUBLICATIONS |
|---|---|---|
| | | WO2011051404 |
| | | U.S. Pat. No. 7,445,855 |
| | | US20070190359, US20080297033 US20100148663 |
| | | U.S. Pat. No. 7,338,722 |
| | | US20020134984 |

TABLE 5-continued

| MATERIAL | EXAMPLES OF MATERIAL | PUBLICATIONS |
| --- | --- | --- |
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 5-continued
| MATERIAL | EXAMPLES OF MATERIAL | PUBLICATIONS |
|---|---|---|
| | 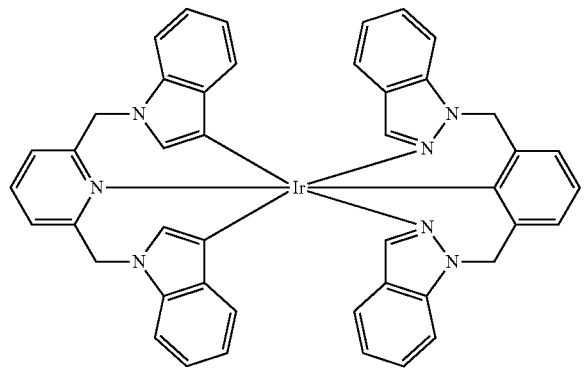 | WO2006082742 |
| Osmium(II) complexes | 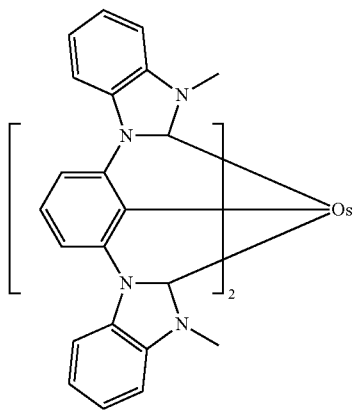 | U.S. Pat. No. 7,279,704 |
| | 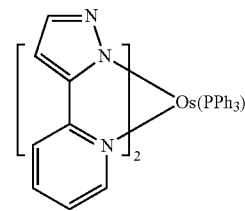 | Organometallics 23, 3745 (2004) |
| Gold complexes | 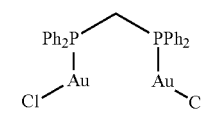 | Appl. Phys. Lett. 74, 1361 (1999) |
| Platinum(II) complexes | 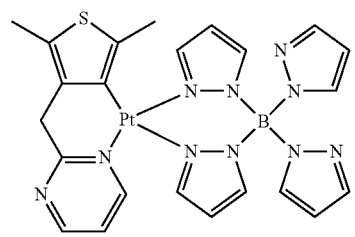 | WO2006098120, WO2006103874 |

TABLE 5-continued

| MATERIAL | EXAMPLES OF MATERIAL | PUBLICATIONS |
| --- | --- | --- |
| Pt tetradentate complexes with at least one metal-carbene bond | | U.S. Pat. No. 7,655,323 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 5-continued

| MATERIAL | EXAMPLES OF MATERIAL | PUBLICATIONS |
|---|---|---|
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE 5-continued
| MATERIAL | EXAMPLES OF MATERIAL | PUBLICATIONS |
|---|---|---|
| Aza-carbazoles | 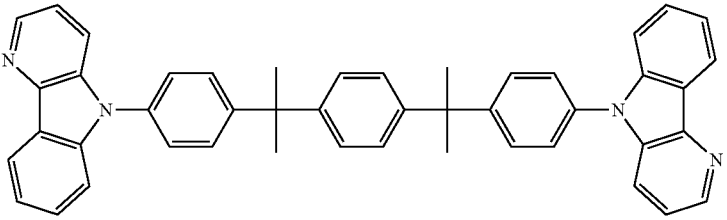 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 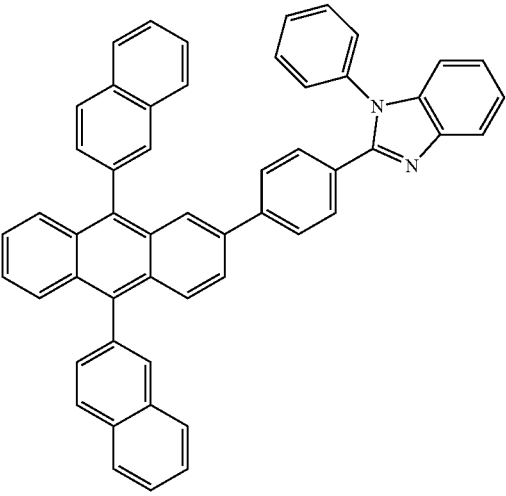 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | | US20090179554 |
| Aza triphenylene derivatives | 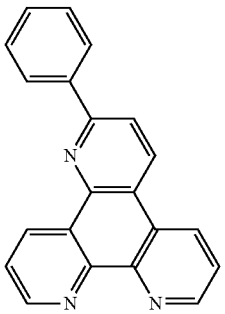 [SMILES: c1ccc(-c2ccc3c4cccnc4c4ncccc4c3n2)cc1] | US20090115316 |
| Anthracene-benzothiazole compounds | 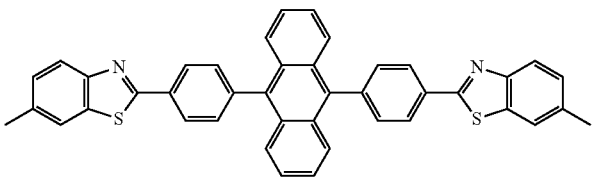 | Appl. Phys. Lett. 89, 063504 (2006) |
| Metal 8-hydroxyquinolates (e.g., $Alq_3$, $Zrq_4$) | 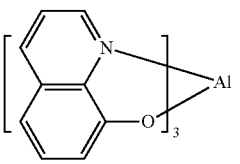 | Appl. Phys. Lett. 51, 913 (1987) U.S. Pat. No. 7,230,107 |

TABLE 5-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 5-continued

| MATERIAL | EXAMPLES OF MATERIAL | PUBLICATIONS |
| --- | --- | --- |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

TABLE 5-continued

| MATERIAL | EXAMPLES OF MATERIAL | PUBLICATIONS |
|---|---|---|
| Zn (N^N) complexes | | U.S. Pat. No. 6,528,187 |

EXPERIMENTAL

Exemplary Material Synthesis

All reactions were carried out under nitrogen atmosphere unless specified otherwise. All solvents for reactions are anhydrous and used as received from commercial sources. In describing the synthesis of various specific examples of the inventive compound, where X in Formula I is S, the compound is named as Compound "No."-S. For example, Compound 1-S referenced below is Compound 1-X defined above where X is S.

Synthesis of Compound 1-S

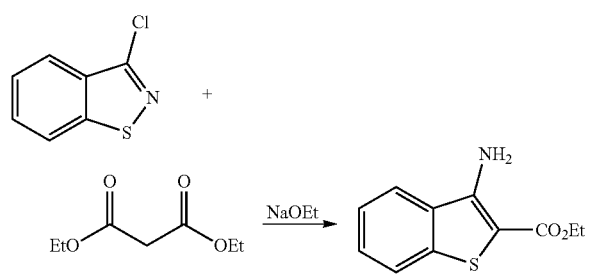

Synthesis of ethyl 3-aminobenzo[b]thiophene-2-carboxylate

A dry 2-neck 500 mL round-bottom flask (RBF) was charged with sodium ethanolate (46.2 mL, 124 mmol), diluted with 151 mL absolute EtOH, cooled in an ice bath and treated dropwise with diethyl malonate (17.98 mL, 118 mmol) under an atmosphere of nitrogen. After stirring for 20 minutes, the ice bath was removed and 3-chlorobenzo[d]isothiazole (20.0 g, 118 mmol) was added in one portion and stirred for 24 hours. The reaction solution was quenched with water, extracted with ether and treated with excess 4 M HCl/dioxane. A pinkish-white precipitate was filtered off, suspended in water, basified with Na$_2$CO$_3$, extracted with ether, washed with water and brine, dried over sodium sulfate, filtered and concentrated to yellow solids (~20 g) which were recrystallized from ethanol/water and dried in a vacuum oven at 60° C. for 3 hrs to give ethyl 3-aminobenzo[b]thiophene-2-carboxylate (19.9 g, 76% yield).

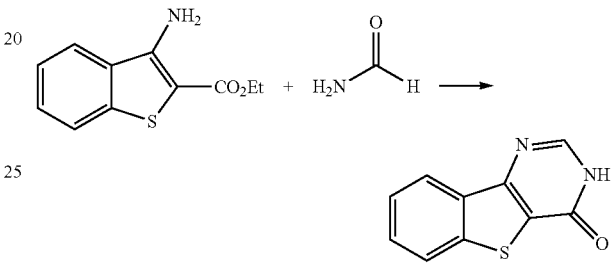

Synthesis of benzo[4,5]thieno[3,2-d]pyrimidin-4(3H)-one

A 100 mL RBF was charged with ethyl 3-aminobenzo[b]thiophene-2-carboxylate (17.7 g, 80 mmol), treated with formamide (60.6 mL, 1520 mmol) and heated to 190° C. for 2 hrs. Precipitate formed upon cooling. The solid was collected by filtration and washed with ether, then recrystallized from ethanol/THF. Benzo[4,5]thieno[3,2-d]pyrimidin-4(3H)-one (9.9 g, 61% yield) was obtained.

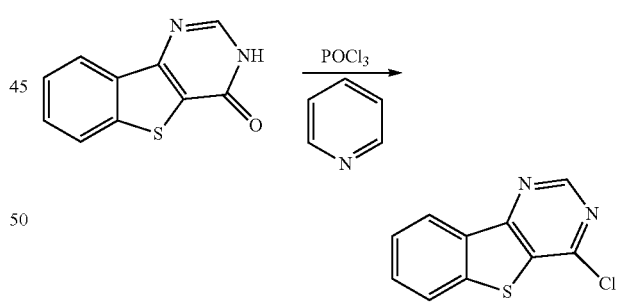

Synthesis of 4-chlorobenzo[4,5]thieno[3,2-d]pyrimidine

Benzo[4,5]thieno[3,2-d]pyrimidin-4(3H)-one (10.78 g, 26.7 mmol) was treated with pyridine (2.68 mL, 33.3 mmol) and phosphoryl trichloride (53.4 mL, 573 mmol), then heated to reflux at 110° C. for 1 hr. Excess POCl$_3$ was removed and cautiously quenched with ice water in an ice bath. The pH was adjusted to ~5 with ammonium hydroxide. Solid was collected by filtration washed with water. The solid was dried to give 4-chlorobenzo[4,5]thieno[3,2-d]pyrimidine (10 g, 85% yield).

Synthesis of Compound D

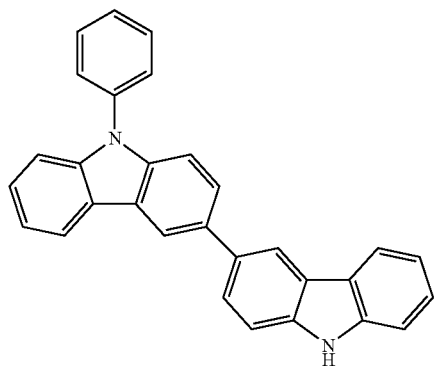

+

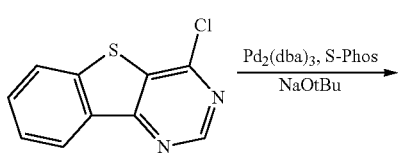

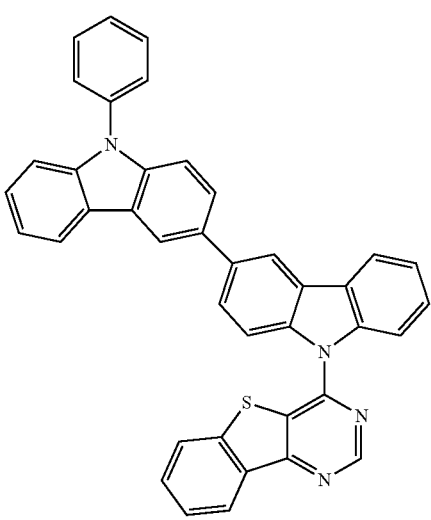

Synthesis of Compound 1-S 9-phenyl-9H,9'H-3,3'-bicarbazole (3.05 g, 7.47 mmol), 4-chlorobenzo[4,5]thieno[3,2-d]pyrimidine (1.812 g, 8.21 mmol), Pd$_2$dba$_3$ (0.342 g, 0.373 mmol), dicyclohexyl(2',6'-dimethoxy-[1,1'-biphenyl]-2-yl)phosphine (S-Phos) (0.307 g, 0.747 mmol), and sodium 2-methylpropan-2-olate (1.794 g, 18.67 mmol) were charged to a 250 mL RBF, diluted in m-Xylene (Volume: 74.7 mL), degassed with nitrogen and heated to reflux at 150° C. overnight. The reaction was quenched with aqueous ammonium chloride and filtered through a plug of Celite® with DCM. The crude was purified by column chromatography and then recrystallized from toluene/ethanol to give 4-(9'-phenyl-9H,9'H-[3,3'-bicarbazol]-9-yl)benzo[4,5]thieno[3,2-d]pyrimidine (1.95 g, 44% yield).

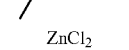

Synthesis of 6-chloro-2-iodopyridin-3-amine 6-chloropyridin-3-amine (40.0 g, 311 mmol) was dissolved in DMF (Volume: 534 mL) and treated with 1-iodopyrrolidine-2,5-dione (70.0 g, 311 mmol) in one portion. The reaction solution was stirred at room temperature under nitrogen overnight and quenched with water and extracted with EtOAc and Et$_2$O. Organic layer was washed twice with brine and dried over sodium sulfate. DMF was removed on kugelrohr at 100° C. to afford ~90 g red solids. The crude was purified via column chromatography to give 6-chloro-2-iodopyridin-3-amine (57 g, 72% yield).

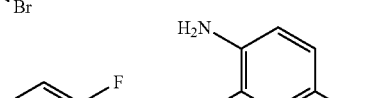

Synthesis of 6-chloro-3'-fluoro-[2,2'-bipyridin]-3-amine

A 3-neck 1000 mL RBF was dried under vacuum, then charged with isopropylmagnesium chloride (78 mL, 156 mmol) and cooled with a water bath. 2-bromo-3-fluoropyridine (14.37 mL, 142 mmol) was added dropwise making sure temperature did not exceed 30° C. The reaction was stirred at room temperature overnight, then treated dropwise with zinc(II) chloride (341 mL, 170 mmol) over 3 hrs and stirred at room temperature overnight. This suspension was then added dropwise via canula to a degassed, 65° C. solution of Pd(PPh₃)₄ (8.21 g, 7.10 mmol) and 6-chloro-2-iodopyridin-3-amine (39.8 g, 156 mmol) in THF (Volume: 474 mL) and heated at reflux overnight. After cooled to room temperature, the reaction was quenched with sat. aq. NaHCO₃ and water. The precipitate was filtered out and washed with EtOAc. The filtrate was extracted with EtOAc. The crude product was purified by column chromatography in 40-50% EtOAc/hexanes with column conditioned in 20% TEA/hexanes to give 6-chloro-3'-fluoro-[2,2'-bipyridin]-3-amine (21.8 g, 69% yield).

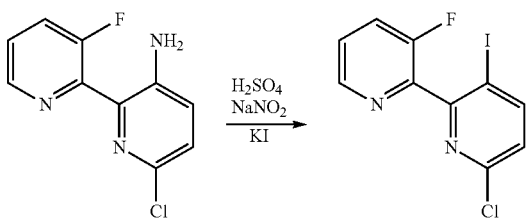

Synthesis of 6-chloro-3'-fluoro-3-iodo-2,2'-bipyridine

A 500 mL 3 neck RBF equipped with mechanical stirrer, reflux condenser, and addition funnel was charged with 6-chloro-3'-fluoro-[2,2'-bipyridin]-3-amine (6.63 g, 29.6 mmol). It was treated with 2 M sulfuric acid (111 mL, 222 mmol) creating a yellow/orange solution. The reaction was cooled to −5° C. and treated dropwise with a solution of sodium nitrite (2.66 g, 38.5 mmol) in 49 mL water at −5° C. The yellow/orange suspension was stirred at 0° C. for 30 minutes, then treated dropwise with a solution of potassium iodide (14.76 g, 89 mmol) in 63 mL of water. The reaction was stirred at room temperature for 30 minutes, then heated to 80° C. for 1 hour. After cooling, the reaction was extracted with EtOAc, washed with water, 2M Na₂CO₃, NaHSO₃, and brine, dried over sodium sulfate, filtered, and concentrated. The crude product was purified by column chromatography using 20% EtOAc/hexanes to give 6-chloro-3'-fluoro-3-iodo-2,2'-bipyridine (16 g, 81% yield).

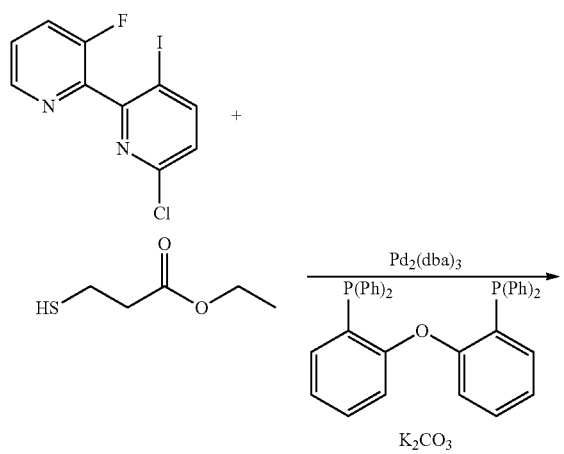

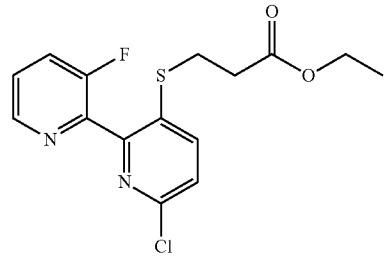

Synthesis of ethyl 3-((6-chloro-3'-fluoro-[2,2'-bipyridin]-3-yl)thio)propanoate 6-chloro-3'-fluoro-3-iodo-2,2'-bipyridine (21.4 g, 64.0 mmol), Potassium Carbonate (22.10 g, 160 mmol), (oxybis (2,1-phenylene))bis(diphenylphosphine) (3.45 g, 6.40 mmol), Pd₂(dba)₃ (2.93 g, 3.20 mmol) were charged to a dry 500 mL RBF, taken up in Toluene (Volume: 256 mL) and degassed with nitrogen. Ethyl 3-mercaptopropanoate (8.92 mL, 70.4 mmol) was added and the reaction solution was heated to reflux for 7 hours. The reaction was quenched with NH₄Cl and extracted with EtOAc. The crude was purified by column chromatography using EtOAc and hexanes to give ethyl 3-((6-chloro-3'-fluoro-[2,2'-bipyridin]-3-yl)thio)propanoate (21.5 g, ~100% yield) with some impurities.

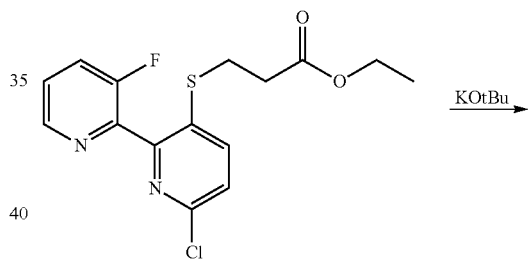

Synthesis of 2-chlorothieno[3,2-b:4,5-b']dipyridine

A 500 mL RBF was charged with ethyl 3-((6-chloro-3'-fluoro-[2,2'-bipyridin]-3-yl)thio)propanoate (16.55 g, 48.6 mmol), THF (Volume: 194 ml) and degassed with nitrogen for 10 minutes, then treated with potassium 2-methylpropan-2-olate (8.17 g, 72.8 mmol) and heated to reflux at 75° C. for 24 hours. The reaction was quenched with aqueous ammonium chloride, extracted 2× with EtOAc. The crude product was purified by column chromatography to give 2-chlorothieno[3,2-b:4,5-b']dipyridine (7 g, 68% yield).

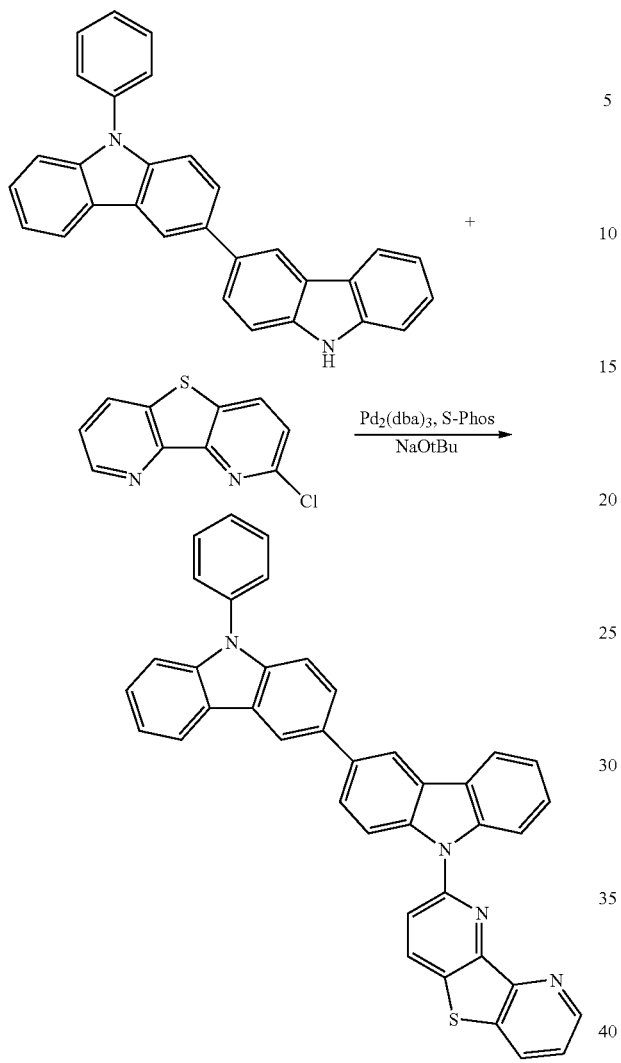

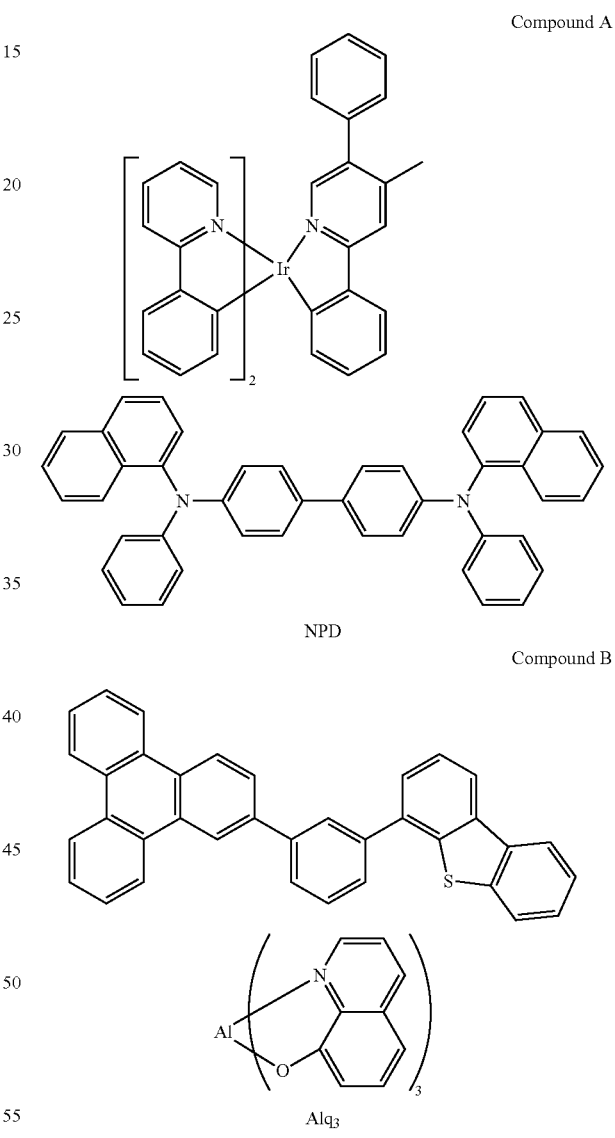

consisting of, sequentially, from the ITO surface, 10 nm thick of Compound A as the hole injection layer (HIL), 30 nm of 4,4'-bis[N-(1-naphthyl)-N-phenylaminolbiphenyl (α-NPD), as the hole transporting layer (HTL), and 300 Å of inventive hosts or comparative hosts doped with 10 wt % of Compound A as the emissive layer (EML). On the top of the EML, 5 nm of Compound B was deposited as a hole blocking (BL) and then followed by 45 nm of tris(8-hydroxyquinolinato)aluminum (Alq$_3$) as the ETL.

Material used in the devices:

Synthesis of Compound D 9-phenyl-9H,9'H-3,3'-bicarbazole (3.0 g, 7.34 mmol), 2-chlorothieno[3,2-b:4,5-b']dipyridine (2.026 g, 9.18 mmol), Pd$_2$dba$_3$ (0.336 g, 0.367 mmol), dicyclohexyl(2',6'-dimethoxy-[1,1'-biphenyl]-2-yl)phosphine (S-Phos) (0.301 g, 0.734 mmol), and sodium 2-methylpropan-2-olate (1.764 g, 18.36 mmol) were charged to a dry 250 mL RBF, treated with m-Xylene (Volume: 73.4 mL) and degassed with nitrogen then heated to reflux at 150° C. overnight. The reaction solution was cooled to room temperature, quenched with aq. NH$_4$Cl and filtered through small plug of Celite® with dichloromethane (DCM). The crude product was purified by column chromatography to give 1.86 g pure product.

Exemplary Devices

All devices were fabricated by high vacuum (~10$^{-7}$ Torr) thermal evaporation. The anode electrode was 120 nm of indium tin oxide (ITO). The cathode consisted of 1 nm of LiF followed by 100 nm of Aluminum. All devices were encapsulated with a glass lid sealed with an epoxy resin in a nitrogen glove box 1 ppm of H$_2$O and O$_2$) immediately after fabrication, and a moisture getter was incorporated inside the package. All device examples had organic stacks

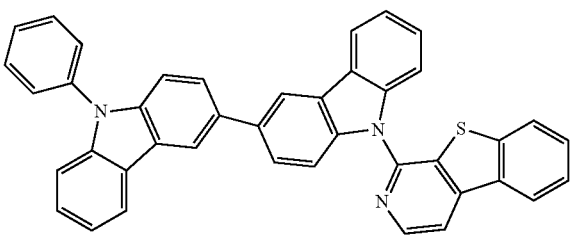

-continued

Compound D

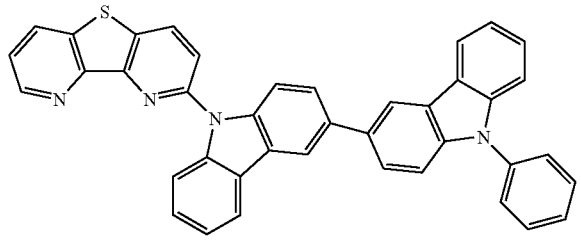

TABLE 2

Device structures of inventive compounds and comparative compounds

| Example | HIL | HTL | EML (300 Å, doping %) | | BL | ETL |
|---|---|---|---|---|---|---|
| Inventive Example 1 | Compound A 100 Å | NPD 300 Å | Compound B:Compound 1-S (73:20) | Compound A 7% | Compound B 50 Å | Alq 450 Å |
| Inventive Example 2 | Compound A 100 Å | NPD 300 Å | Compound 1-S (90%) | Compound A 10% | Compound B 50 Å | Alq 450 Å |
| Comparative Example 1 | Compound A 100 Å | NPD 300 Å | Compound B:Compound C (73:20) | Compound A 7% | Compound B 50 Å | Alq 450 Å |
| Comparative Example 2 | Compound A 100 Å | NPD 300 Å | Compound B:Compound D (73:20) | Compound A 7% | Compound B 50 Å | Alq 450 Å |
| Comparative Example 3 | Compound A 100 Å | NPD 300 Å | Compound C (90%) | Compound A 10% | Compound B 50 Å | Alq 450 Å |
| Comparative Example 4 | Compound A 100 Å | NPD 300 Å | Compound D (90%) | Compound A 10% | Compound B 50 Å | Alq 450 Å |

TABLE 3

Device results

| | x | y | $\lambda_{max}$ (nm) | Relative Voltage | Relative EQE | Relative LT95 from 9000 nits |
|---|---|---|---|---|---|---|
| Inventive Example 1 | 0.343 | 0.612 | 524 | 1.03 | 1.2 | 1.54 |
| Comparative Example 1 | 0.338 | 0.615 | 524 | 1.0 | 1.1 | 0.7 |
| Comparative Example 2 | 0.335 | 0.617 | 522 | 1.0 | 1.0 | 1.0 |

TABLE 4

Device results

| | x | y | $\lambda_{max}$ (nm) | Relative Voltage | Relative EQE | Relative LT95 from 9000 nits |
|---|---|---|---|---|---|---|
| Inventive Example 2 | 0.347 | 0.611 | 526 | 0.86 | 2.0 | 9.33 |
| Comparative Example 3 | 0.345 | 0.612 | 526 | 0.86 | 1.76 | 1.0 |
| Comparative Example 4 | 0.347 | 0.605 | 526 | 1.0 | 1.0 | 1.0 |

Table 3 above summarizes the performance of the devices with dual hosts containing Compound B and inventive compound Compound 1-S or Compounds C and D. Table 4 above summarizes the performance of the devices with single host inventive compound Compound 1-S or Compounds C and D. The driving voltage, and external quantum efficiency (EQE) were measured at 1000 nits, while the lifetime (LT95) was defined as the time required for the device to decay to 95% of its initial luminance of 9000 nits. All devices have essentially same emission color, which is from the emission of Compound A. Device with inventive Compound 1-S as host shows much improved performance compared to the comparative examples. When used as a cohost with Compound B, inventive Compound 1-S showed similar driving voltage and slightly improved efficiency compared to that of Compounds C and D. However, the device lifetime was improved by 50% compared to Compound D, and more than doubled compared to Compound C. When used as a single host, inventive Compound 1-S showed much lower voltage than that of Compound D, much higher efficiency than both Compounds C and D. More importantly, the device lifetime with Compound 1-S is more than 9 times better than that of Compounds C and D. These results have clearly demonstrated the unexpected advantages of using the current invented compounds in OLED device.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having a structure according to Formula I

Formula I

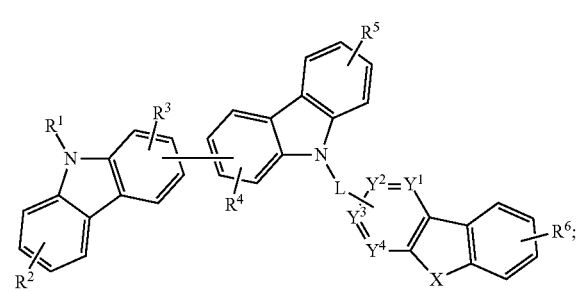

wherein $R^2$, $R^5$, and $R^6$ represent mono, di, tri, tetra substitutions or no substitution;

wherein $R^3$, and $R^4$ represent mono, di, tri substitutions or no substitution;

wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;

wherein X is selected from the group consisting of O, S, and Se;

wherein each of $Y^1$, $Y^2$, $Y^3$, and $Y^4$ is carbon or nitrogen;

wherein at least two of $Y^1$, $Y^2$, $Y^3$, and $Y^4$ are nitrogen;

wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

2. The compound of claim 1, wherein $R^1$ is aryl or heteroaryl.

3. The compound of claim 1, wherein $R^1$ is selected from the group consisting of phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof.

4. The compound of claim 1, wherein $R^2$, $R^3$, $R^4$, $R^5$ and $R^6$ are each independently selected from the group consisting of hydrogen, deuterium, aryl, heteroaryl and combinations thereof.

5. The compound of claim 1, wherein $R^2$, $R^3$, $R^4$, $R^5$ and $R^6$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene and combinations thereof.

6. The compound of claim 1, wherein $R^2$, $R^3$, $R^4$, $R^5$ and $R^6$ are hydrogen.

7. The compound of claim 1, wherein L is selected from the group consisting of:

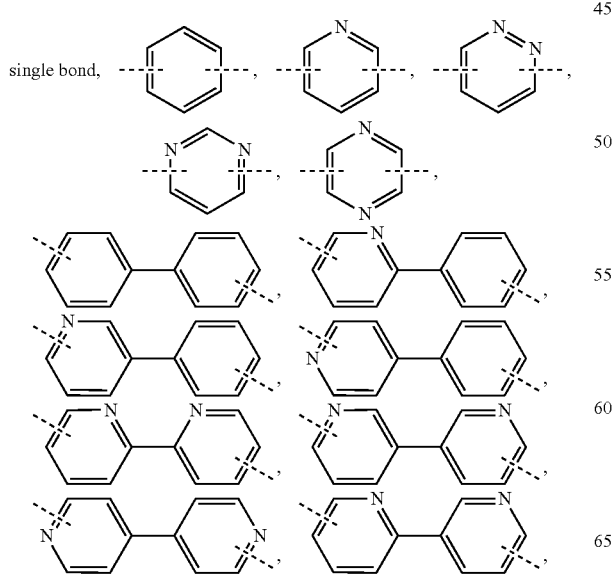

-continued

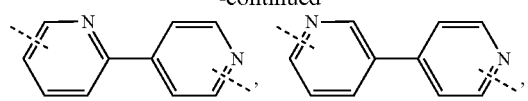

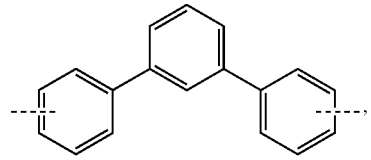

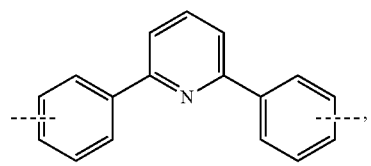

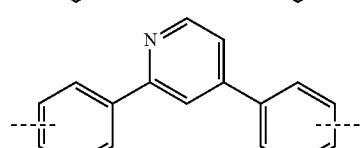

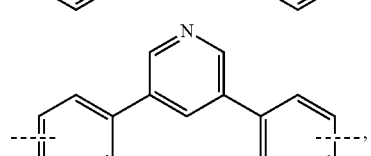

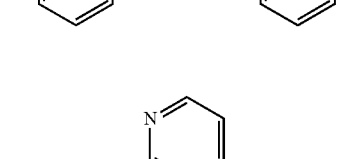

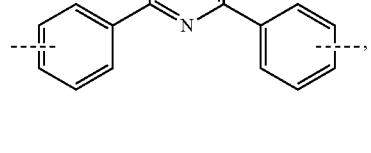

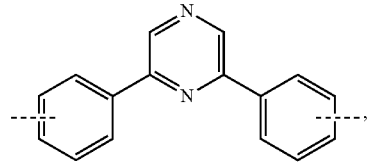

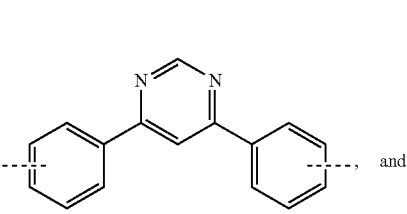, and

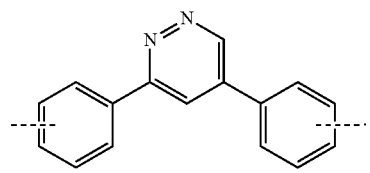.

8. The compound of claim 1, wherein X is O.

9. The compound of claim 1, wherein X is S.

10. The compound of claim 1, wherein the compound is selected from the group consisting of:
Compound 1-X
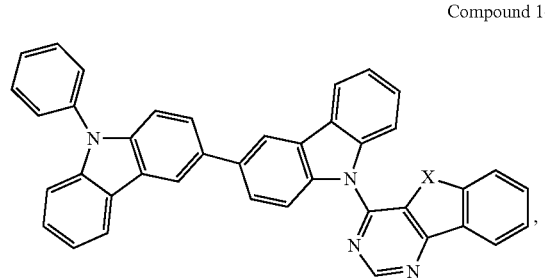
Compound 2-X
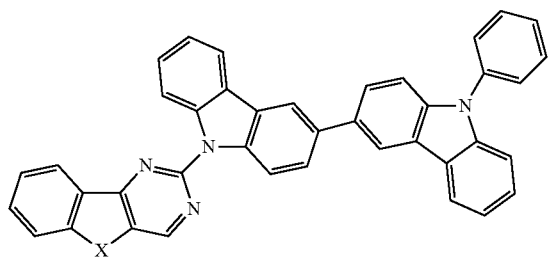
Compound 3-X
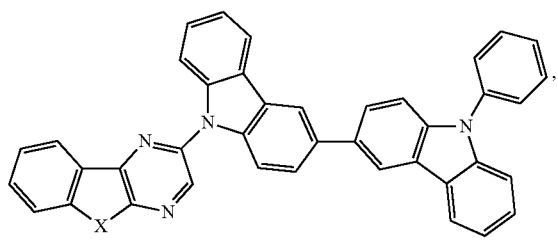
Compound 4-X
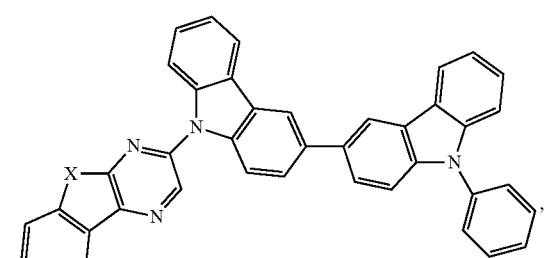
Compound 5-X
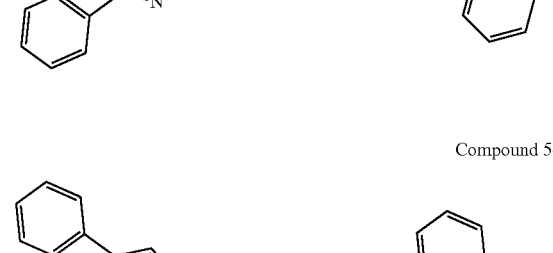
Compound 6-X
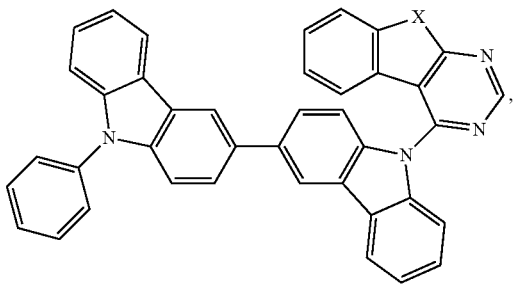
Compound 7-X
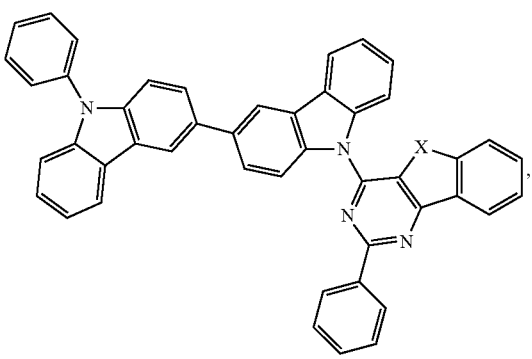
Compound 8-X
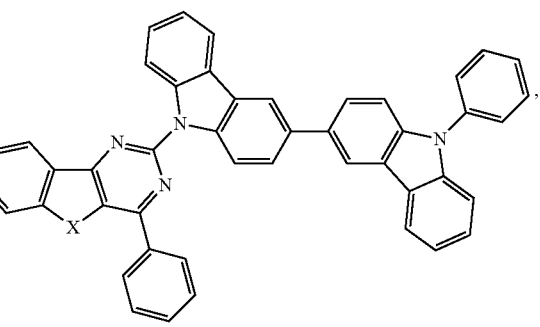
Compound 9-X
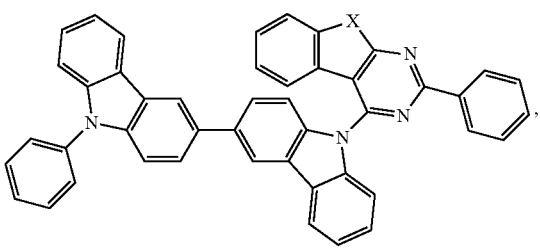
Compound 10-X
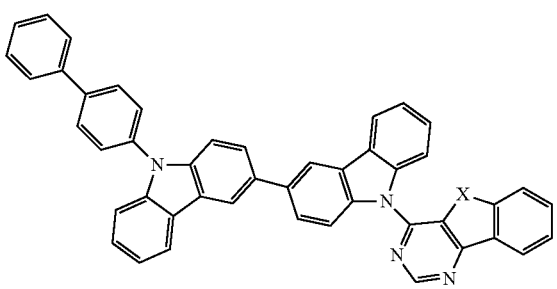

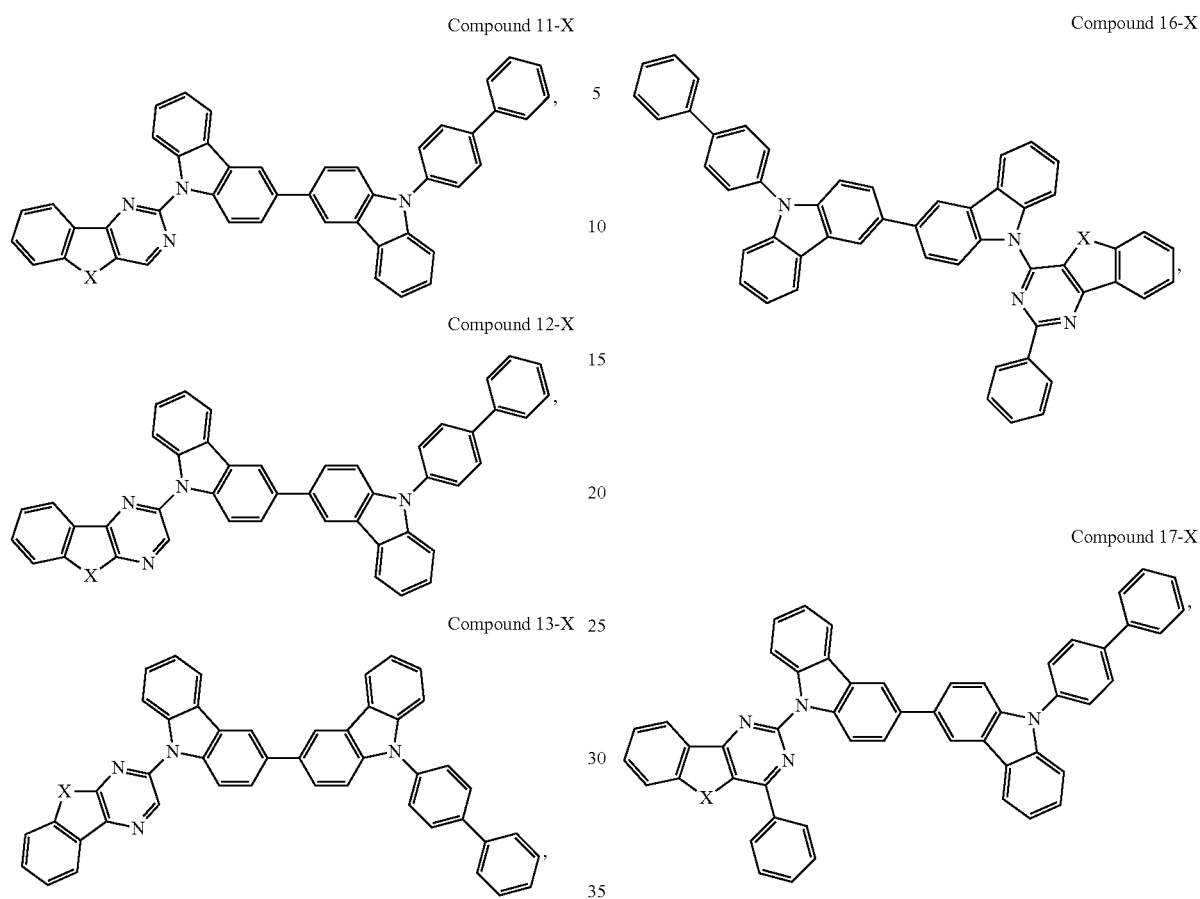
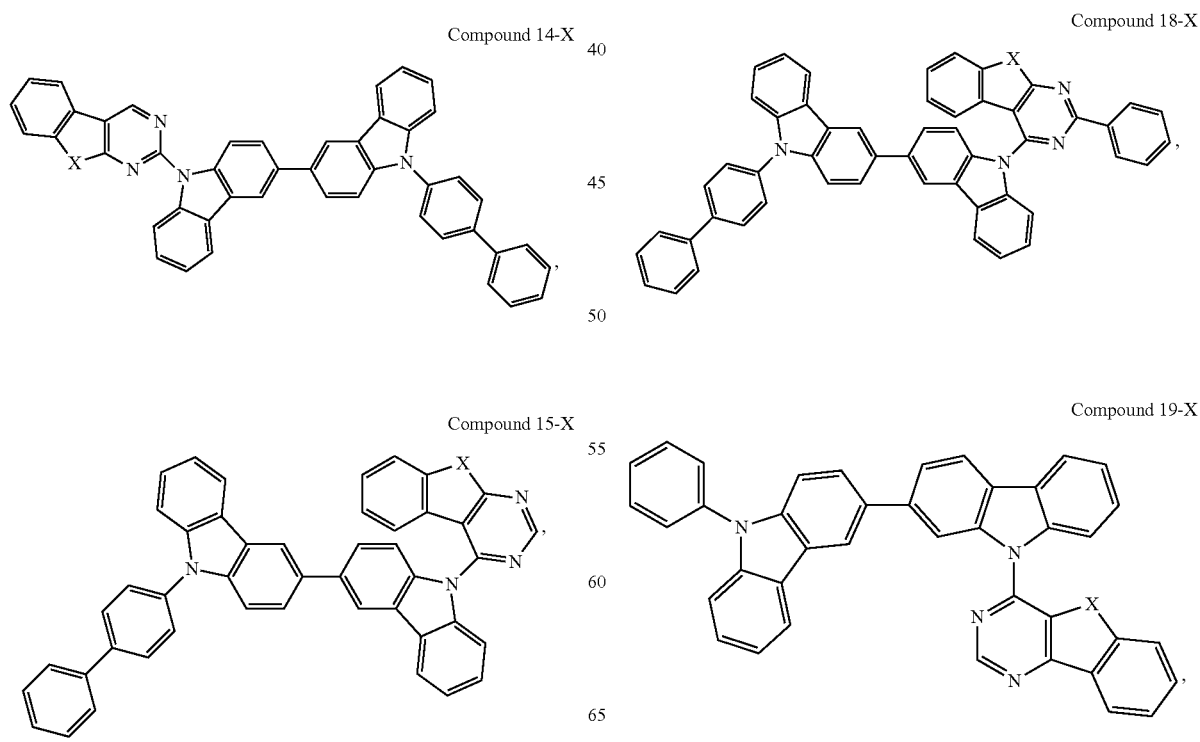

Compound 20-X
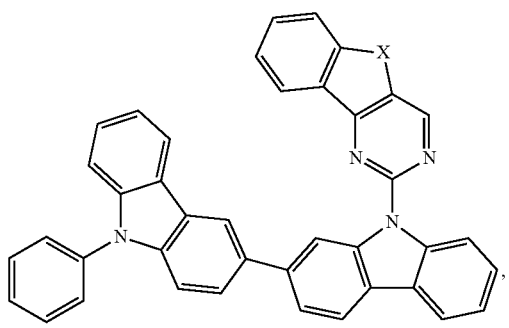
Compound 21-X
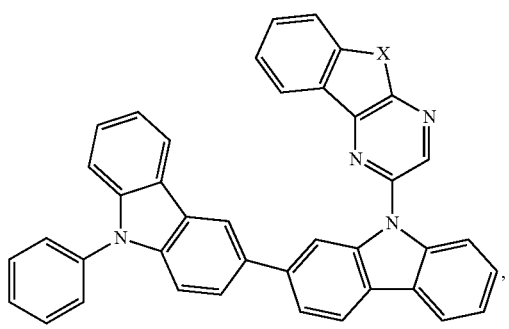
Compound 22-X
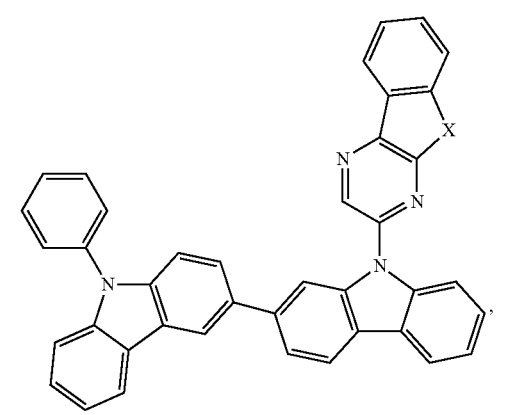
Compound 23-X
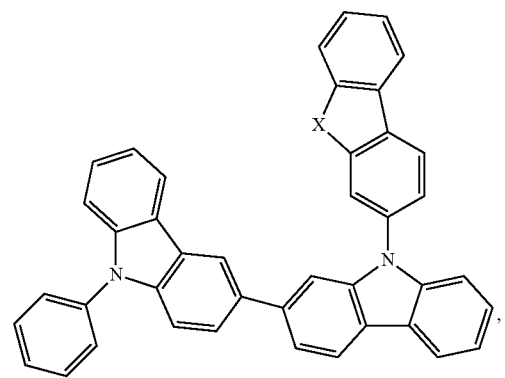
Compound 24-X
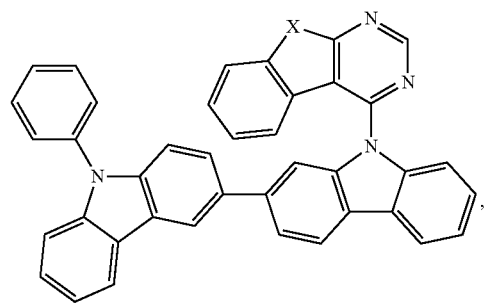
Compound 25-X
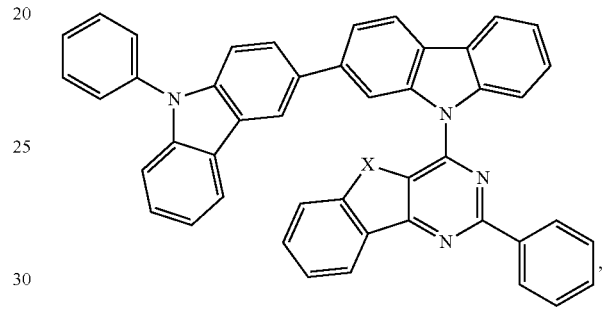
Compound 26-X
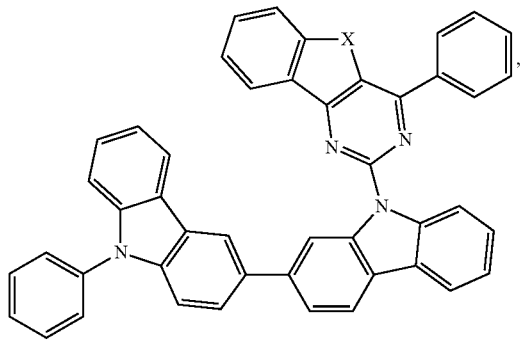
Compound 27-X
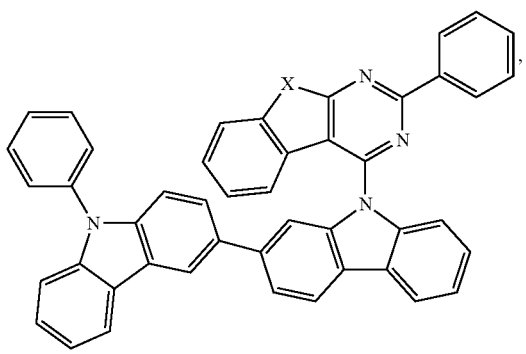

Compound 28-X
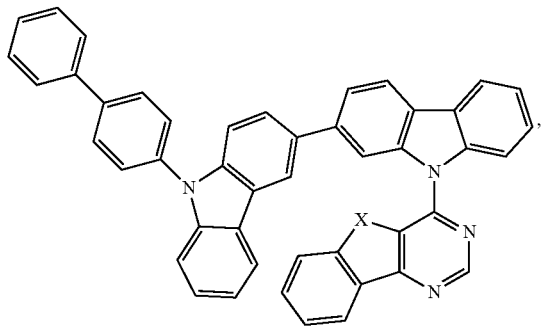
Compound 29-X
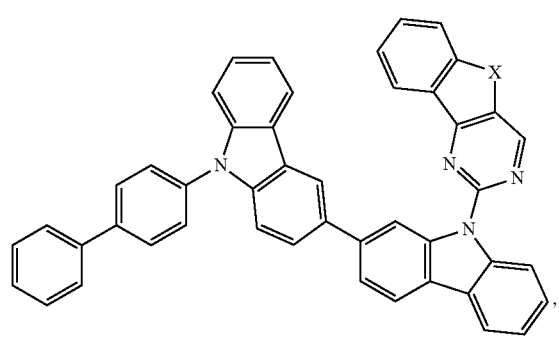
Compound 30-X
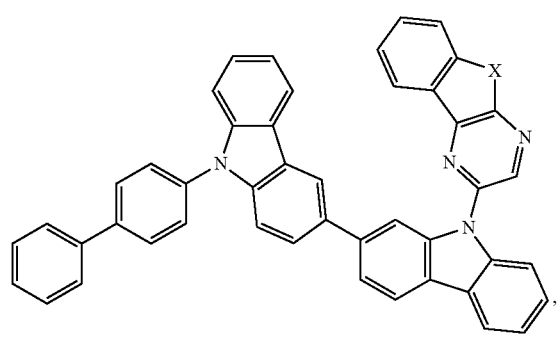
Compound 31-X
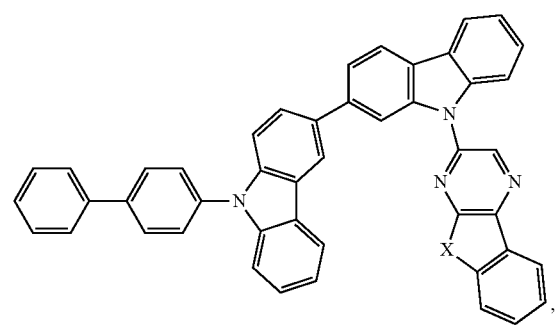
Compound 32-X
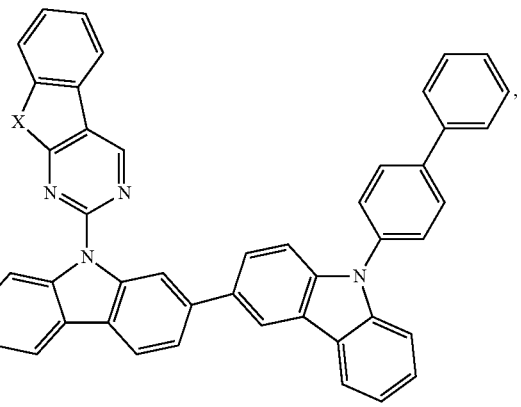
Compound 33-X
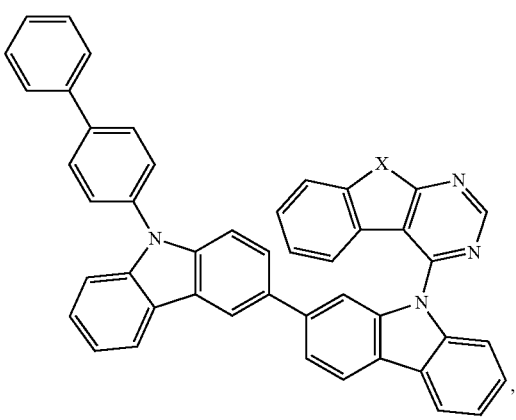
Compound 34-X
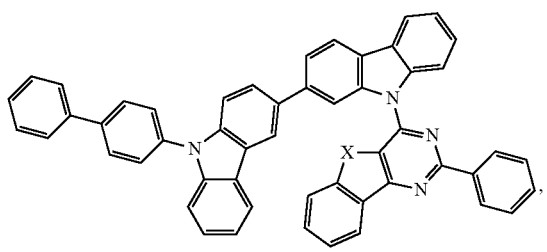
Compound 35-X
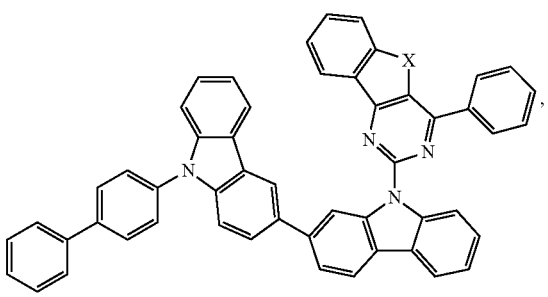

Compound 36-X
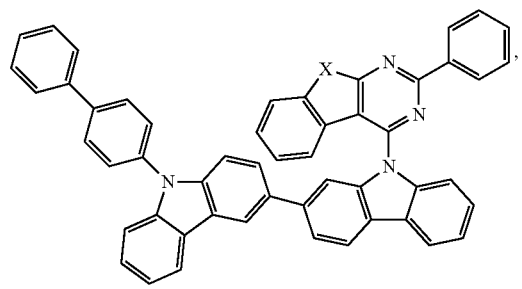
Compound 42-X
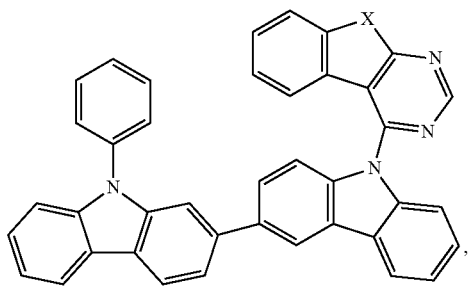
Compound 37-X
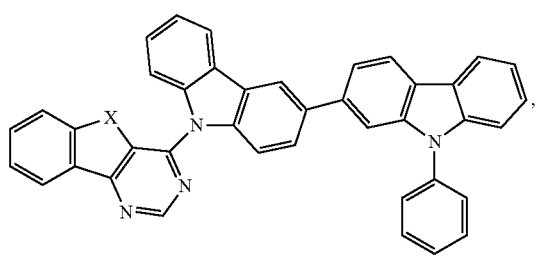
Compound 43-X
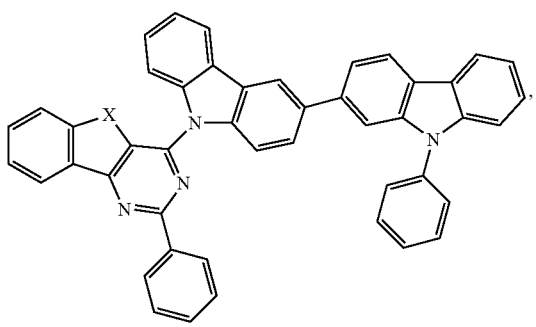
Compound 38-X
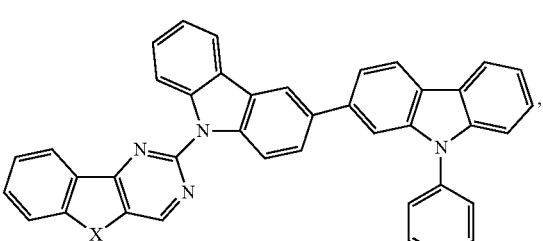
Compound 39-X
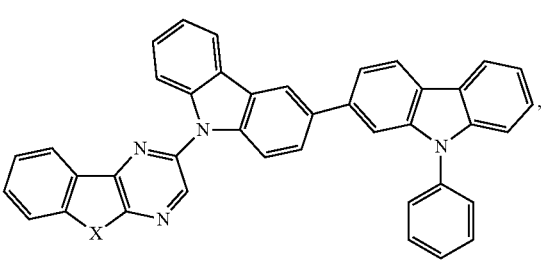
Compound 44-X
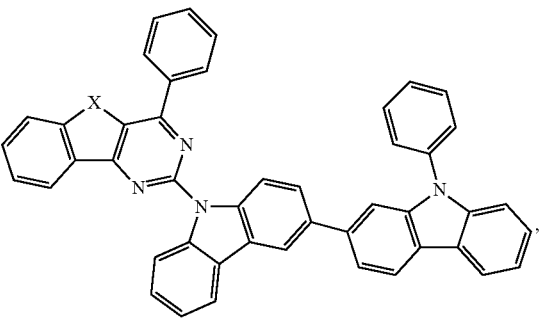
Compound 40-X
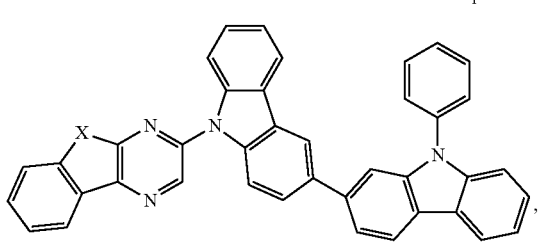
Compound 45-X
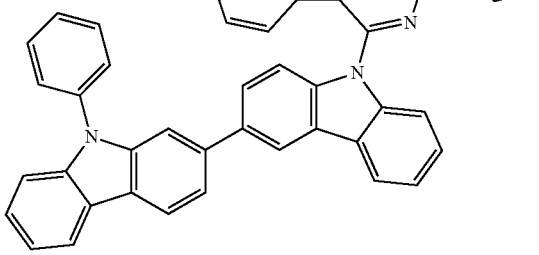
Compound 41-X
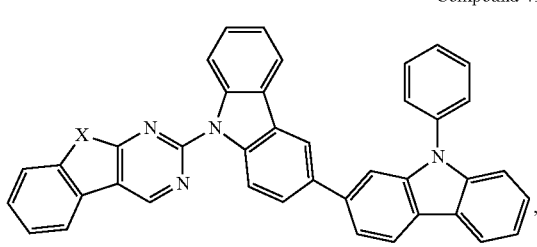

-continued
Compound 46-X
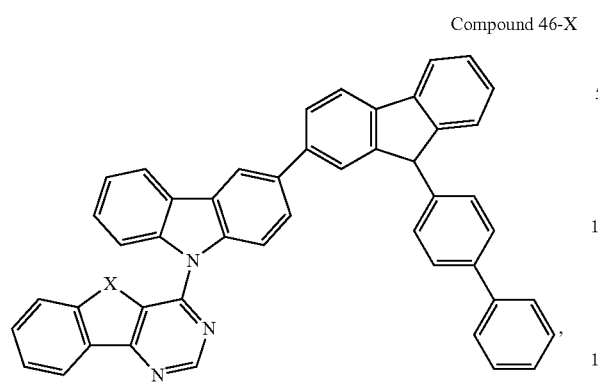
Compound 47-X
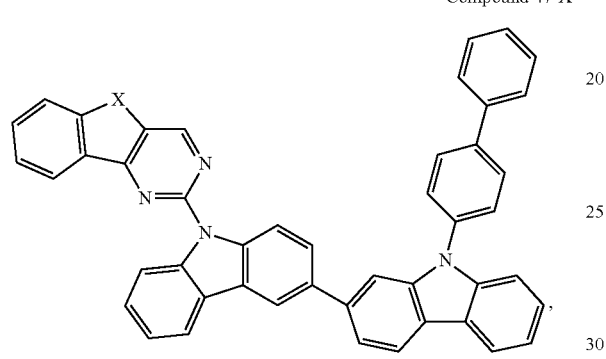
Compound 48-X
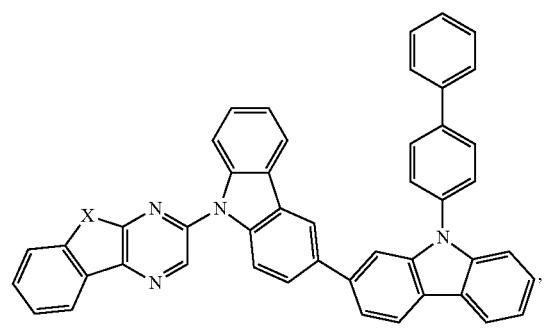
Compound 49-X
Compound 50-X
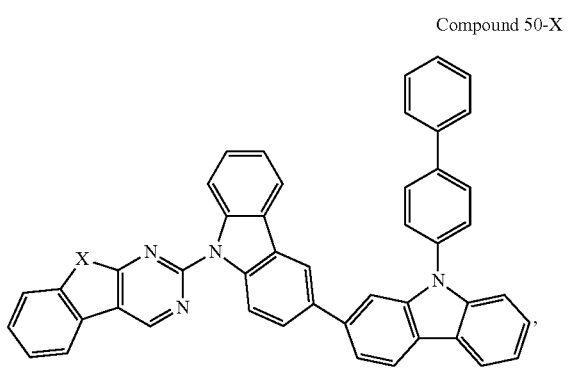
Compound 51-X
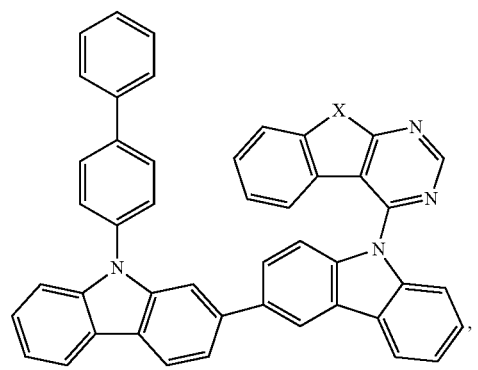
Compound 52-X
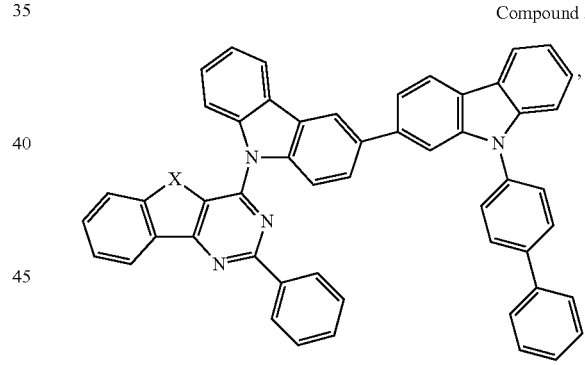
Compound 53-X
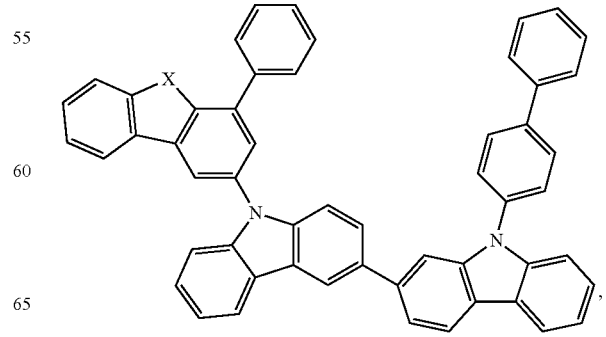

-continued
Compound 54-X
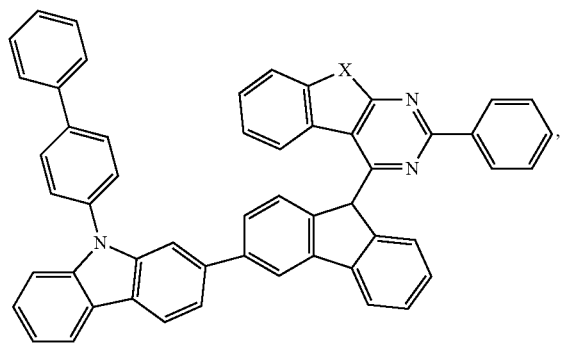
Compound 55-X
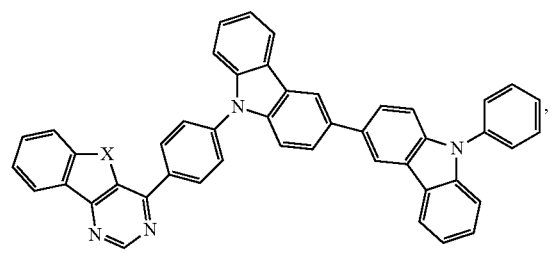
Compound 56-X
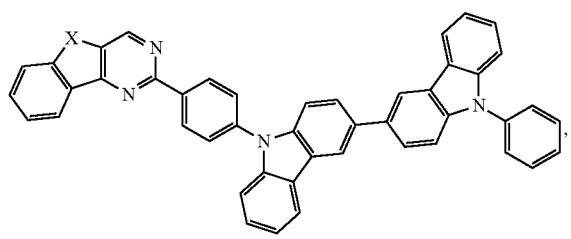
Compound 57-X
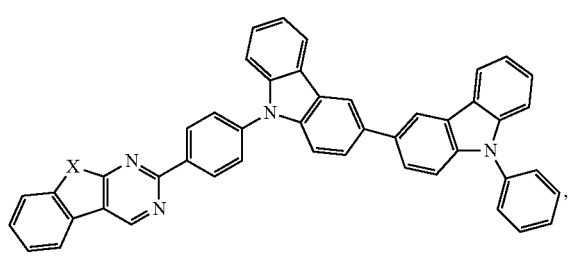
Compound 58-X
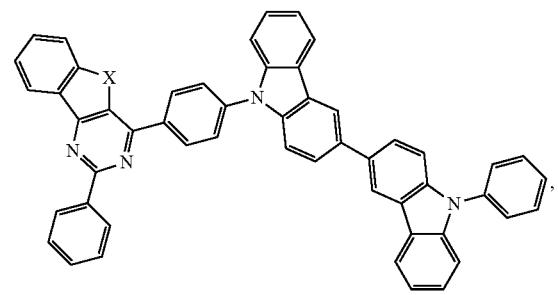
-continued
Compound 59-X
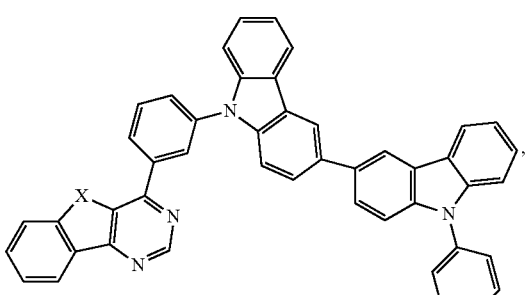
Compound 60-X
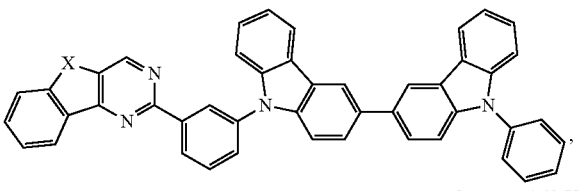
Compound 61-X
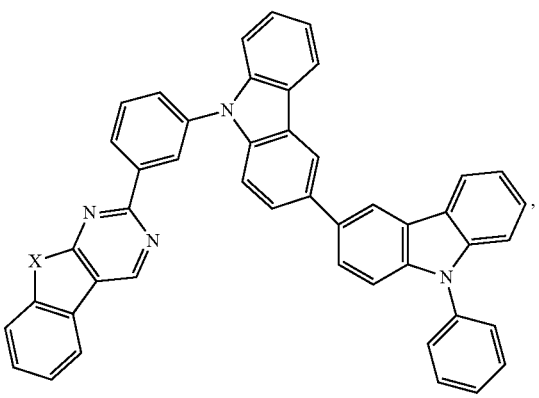
Compound 62-X
Compound 63-X
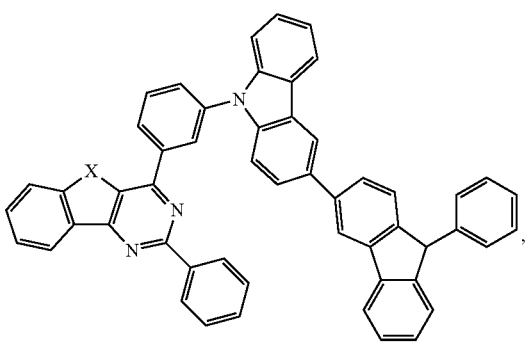

Compound 64-X
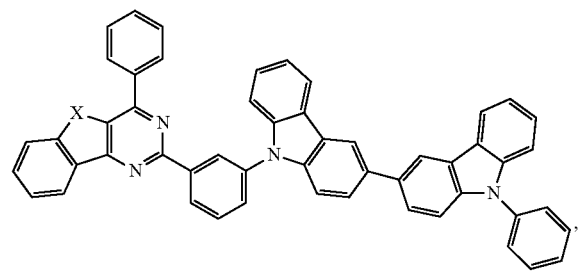
Compound 65-X
Compound 66-X
Compound 67-X
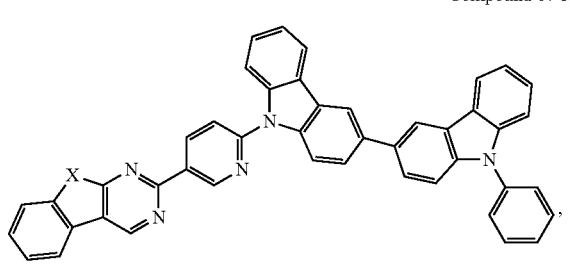
Compound 68-X
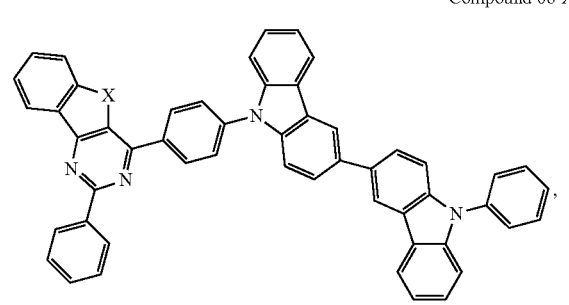
Compound 69-X
Compound 70-X
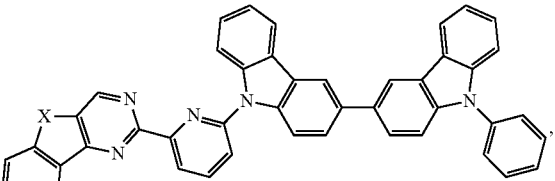
Compound 71-X
Compound 72-X
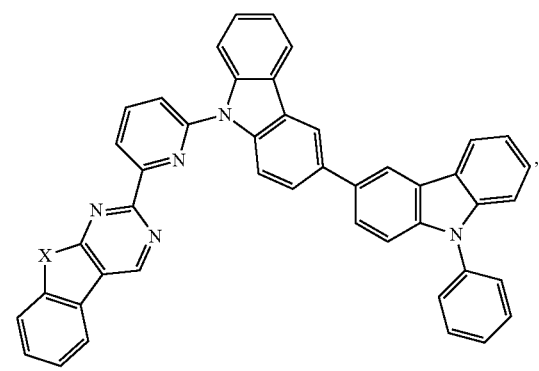

Compound 73-X
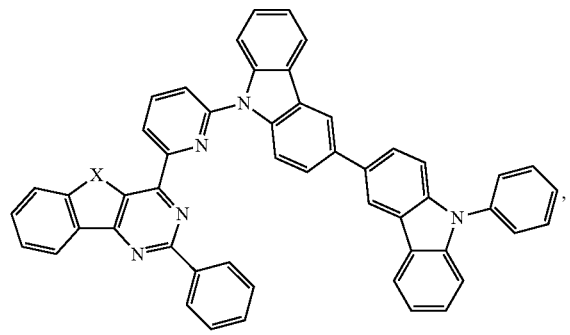
Compound 74-X
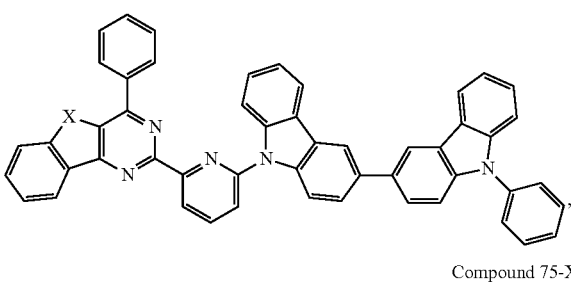
Compound 75-X
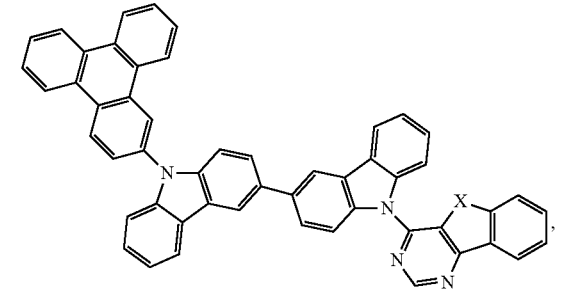
Compound 76-X
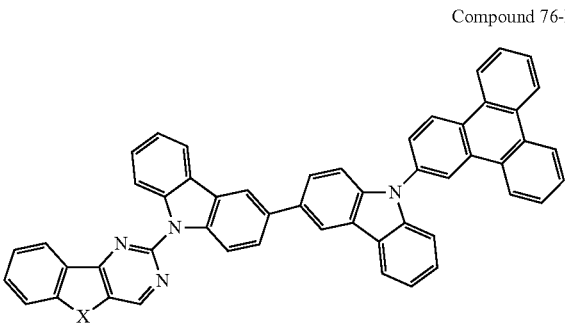
Compound 77-X
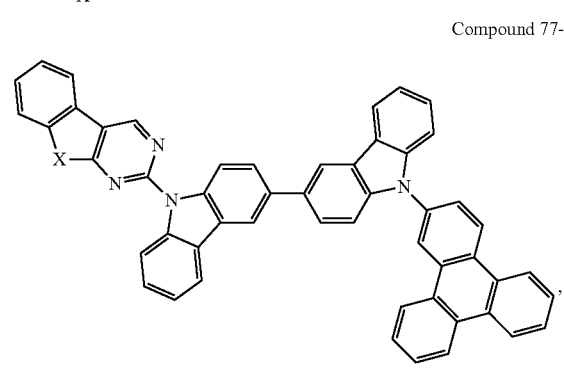
Compound 78-X
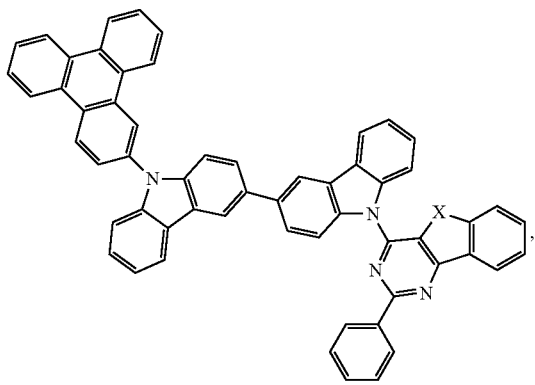
Compound 79-X
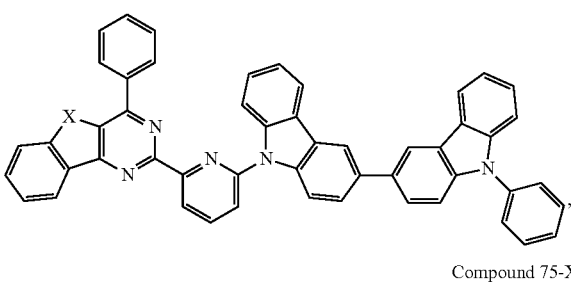
Compound 80-X
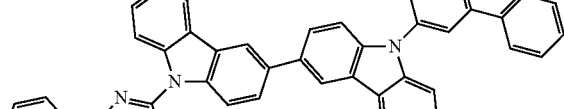
Compound 81-X
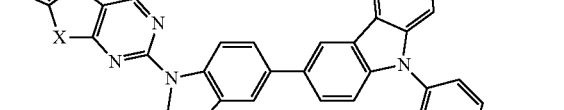

Compound 82-X
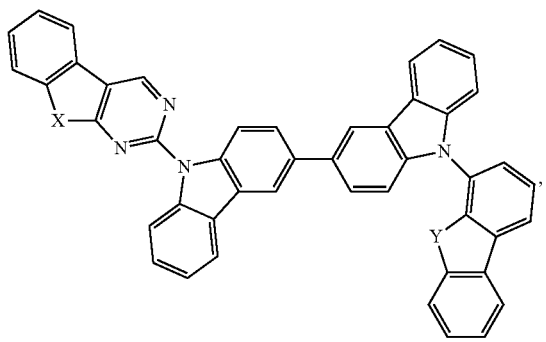
Compound 83-X
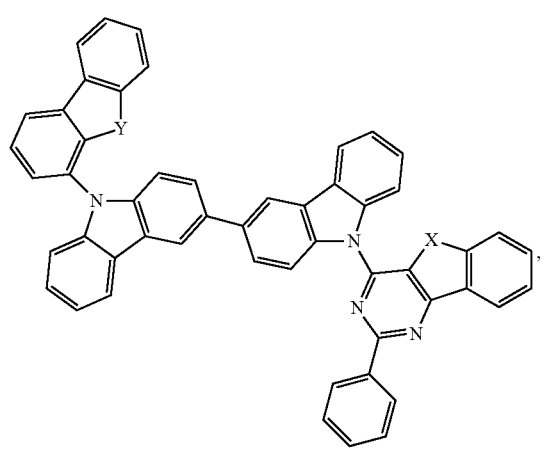
Compound 84-X
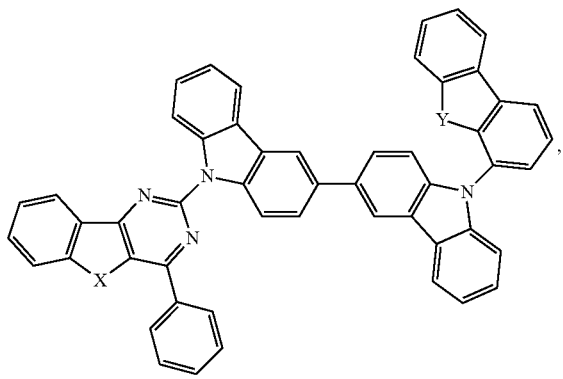
Compound 85-X
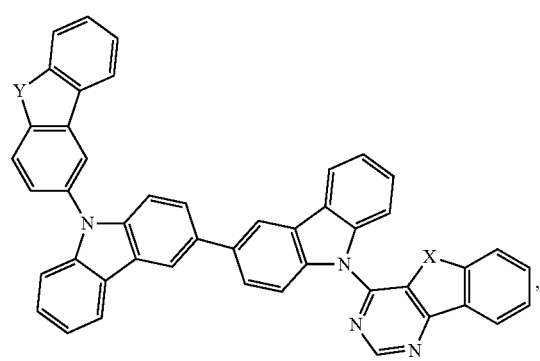
Compound 86-X
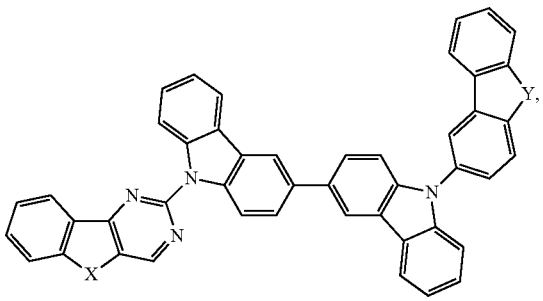
Compound 87-X
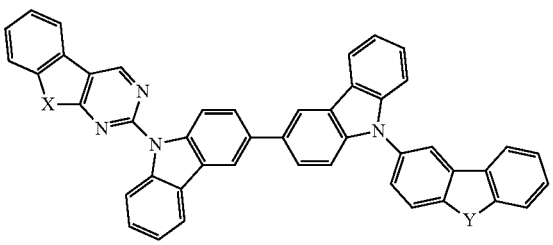
Compound 88-X
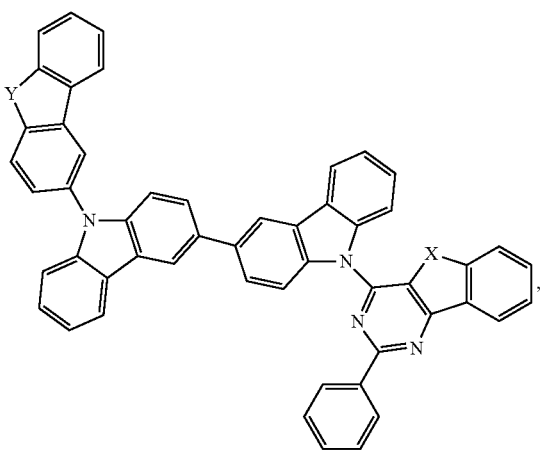
Compound 89-X
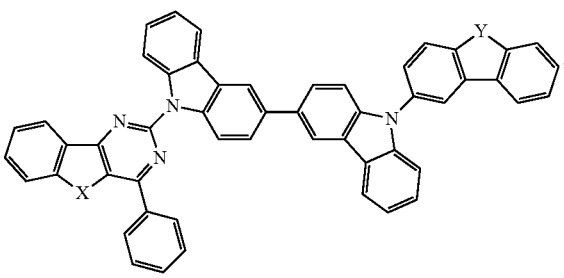

Compound 90-X
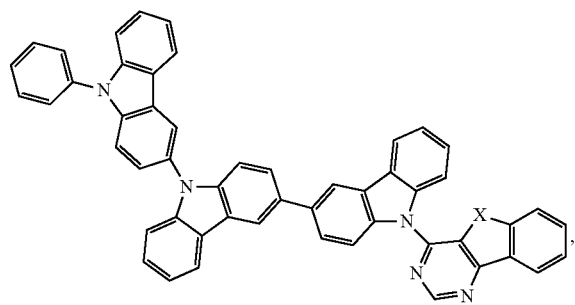
Compound 91-X
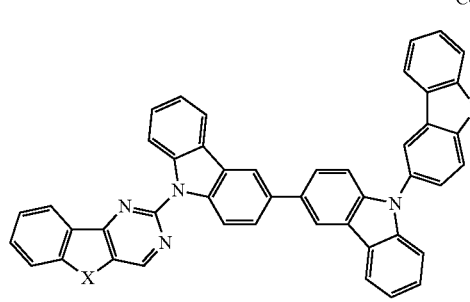
Compound 92-X
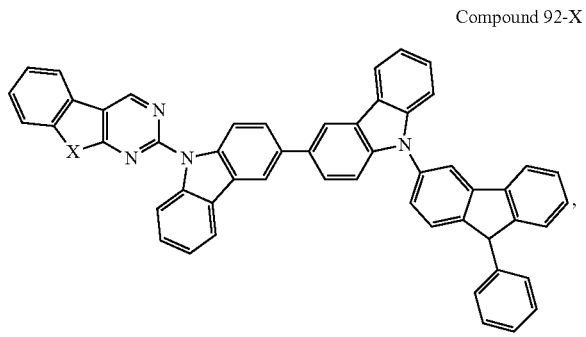
Compound 93-X
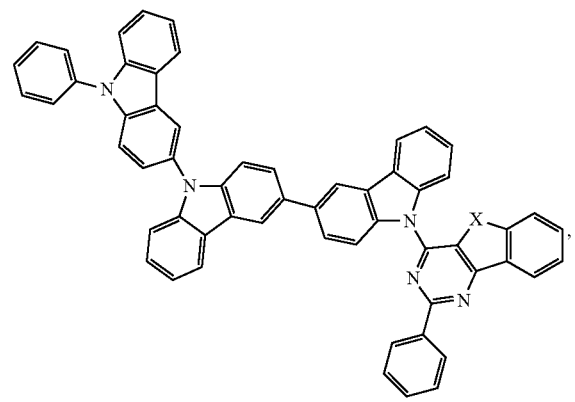
Compound 94-X
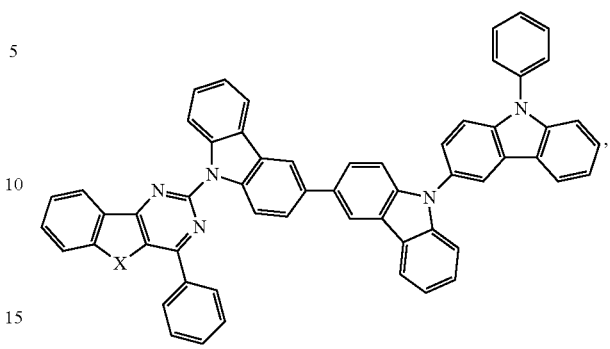
Compound 95-X
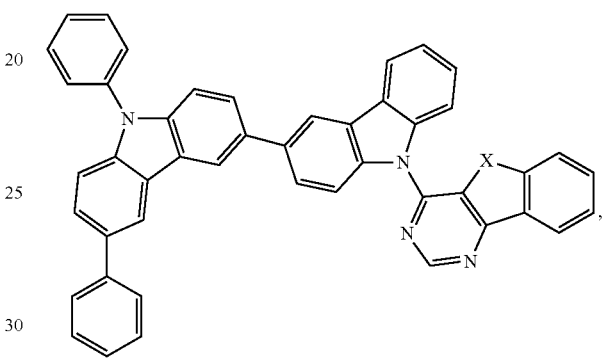
Compound 96-X
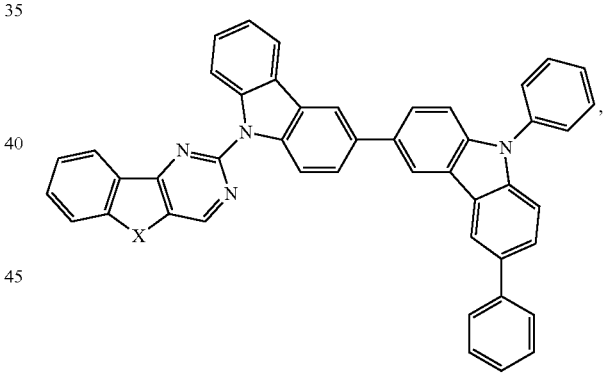
Compound 97-X
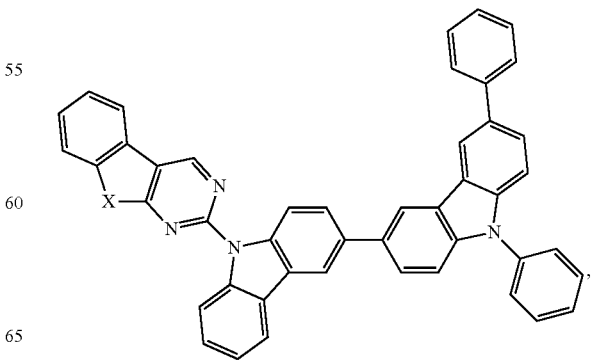

-continued

Compound 98-X

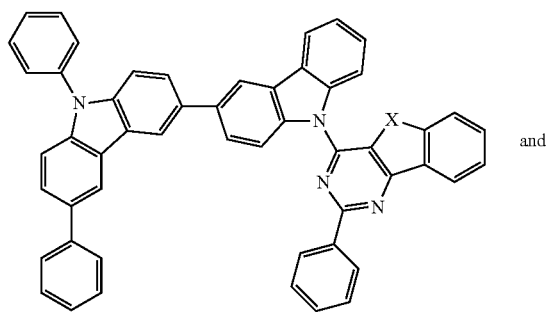

and

Compound 99-X

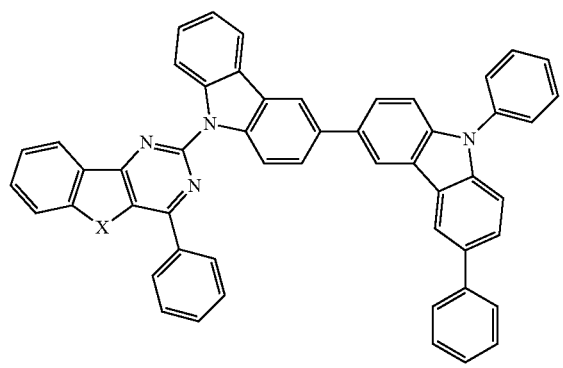

wherein Y in Compounds 80-X through 89-X is selected from the group consisting of O, S, and Se.

11. A first device comprising an organic light emitting device, the organic light emitting device comprising: an anode; a cathode; an organic layer, disposed between the anode and the cathode, wherein the organic layer is an emissive layer and the organic layer comprises a compound having a structure according to Formula I Formula I

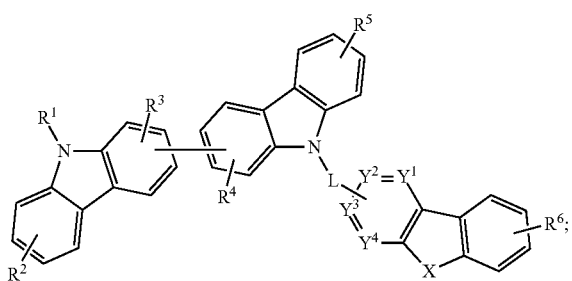

wherein $R^2$, $R^5$, and $R^6$ represent mono, di, tri, tetra substitutions or no substitution;
wherein $R^3$, and $R^4$ represent mono, di, tri substitutions or no substitution;
wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;
wherein X is selected from the group consisting of O, S, and Se;
wherein each of $Y^1$, $Y^2$, $Y^3$, and $Y^4$ is carbon or nitrogen;
wherein at least two of $Y^1$, $Y^2$, $Y^3$, and $Y^4$ are nitrogen;
wherein at least one of $Y^1$, $Y^2$, $Y^3$, and $Y^4$ is carbon and bonded to L; and
wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

12. The first device of claim 11, wherein the compound is selected from the group consisting of:

Compound 1-X

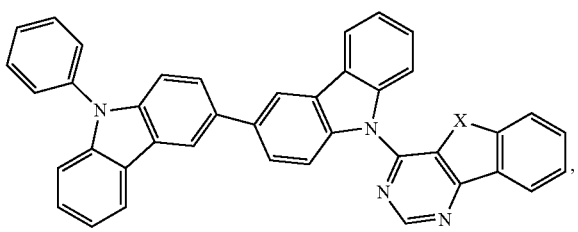

Compound 2-X

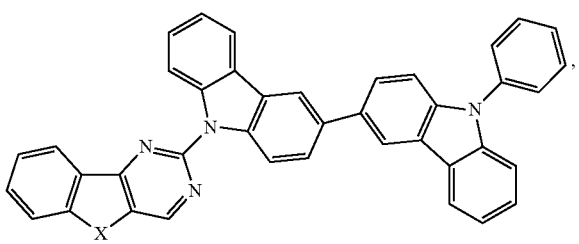

Compound 3-X

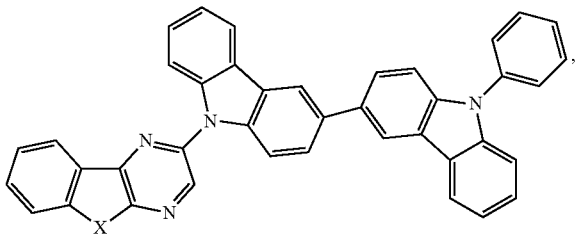

Compound 4-X

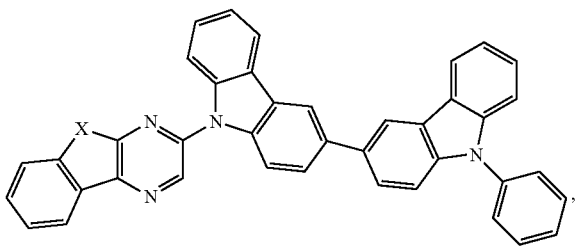

Compound 5-X
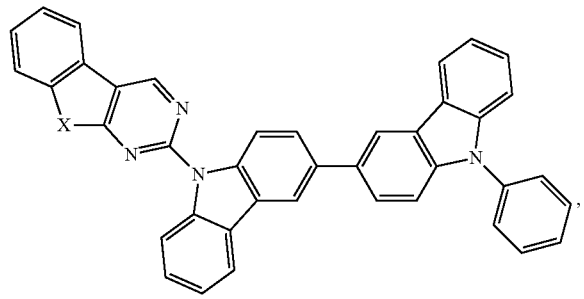
Compound 6-X
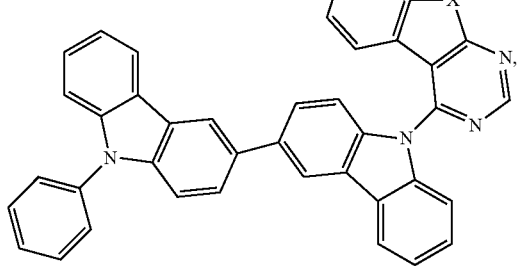
Compound 7-X
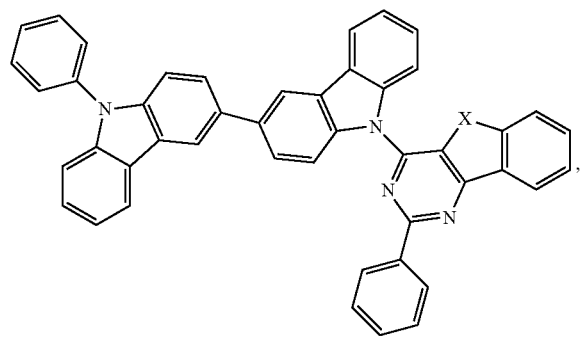
Compound 8-X
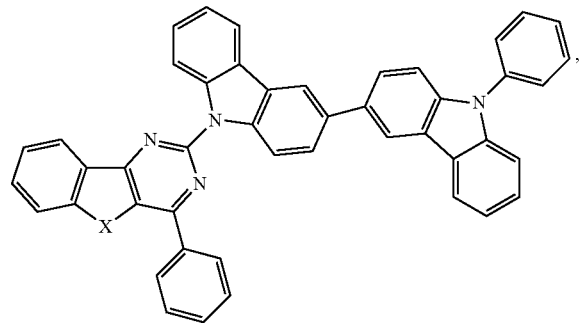
Compound 9-X
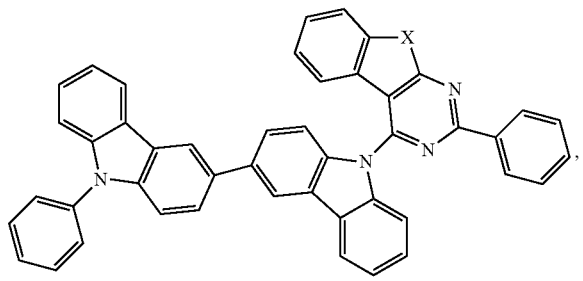
Compound 10-X
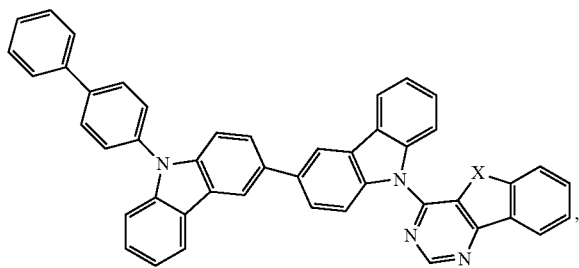
Compound 11-X
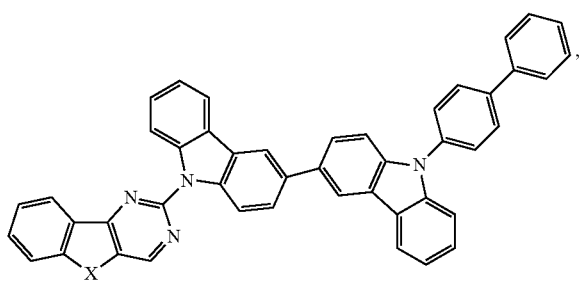
Compound 12-X
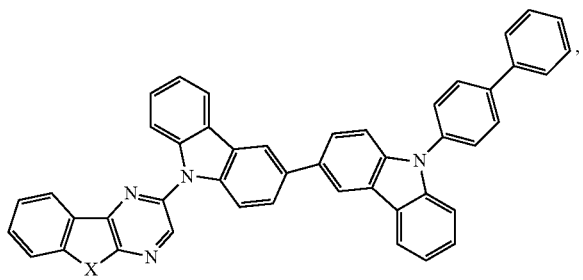
Compound 13-X
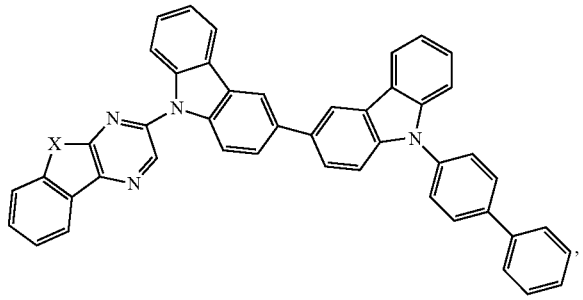

Compound 14-X
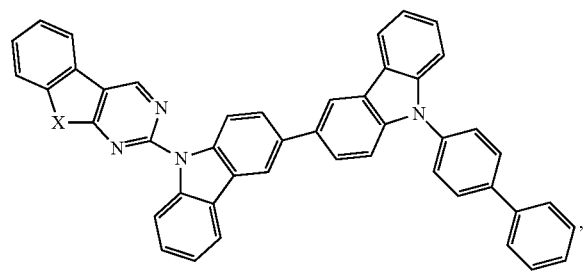
Compound 15-X
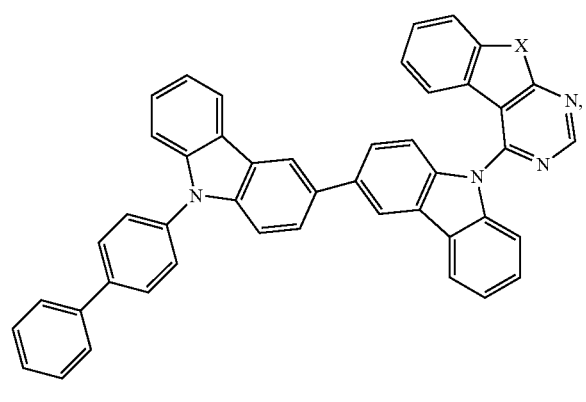
Compound 16-X
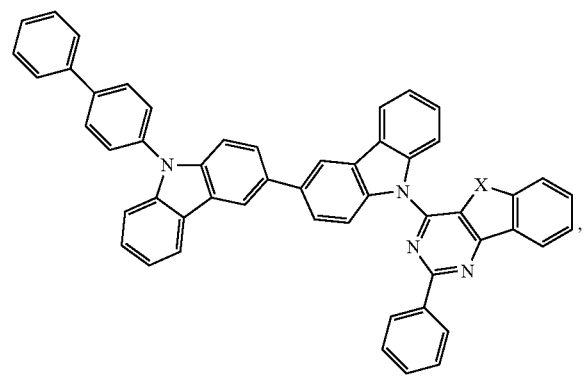
Compound 17-X
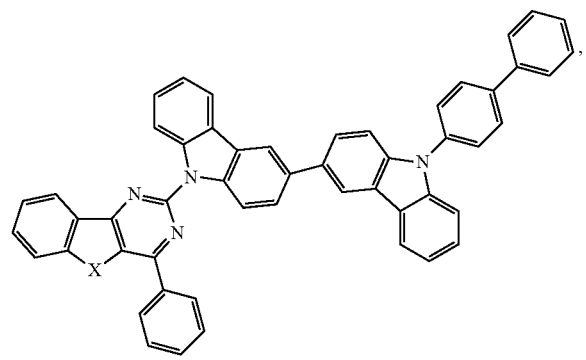
Compound 18-X
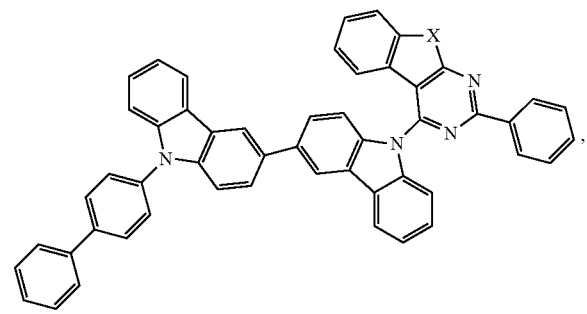
Compound 19-X
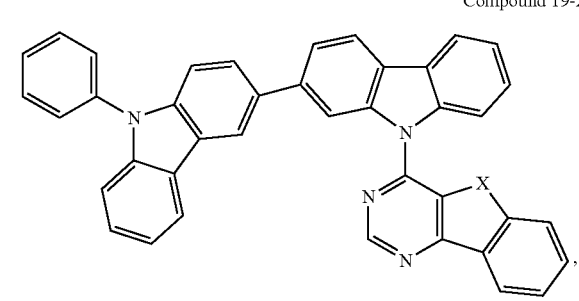
Compound 20-X
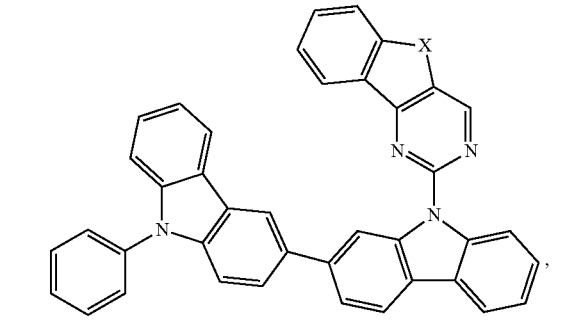
Compound 21-X
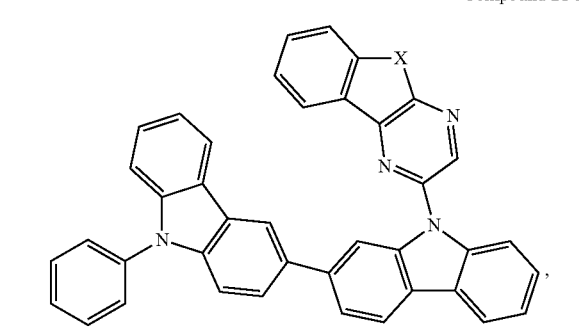

Compound 22-X
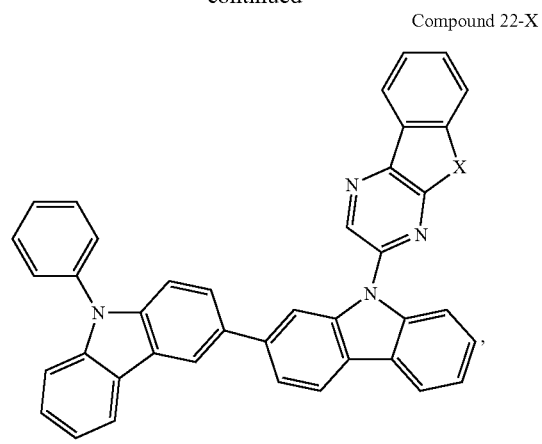
Compound 23-X
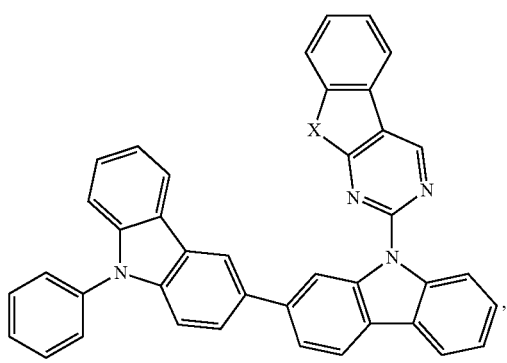
Compound 24-X
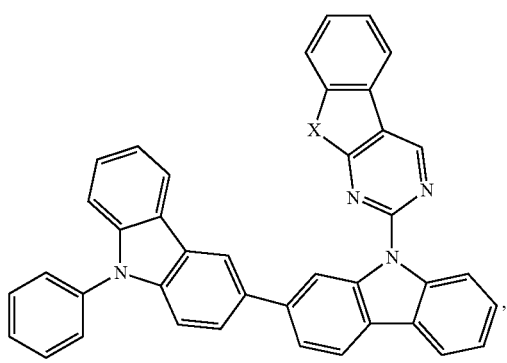
Compound 25-X
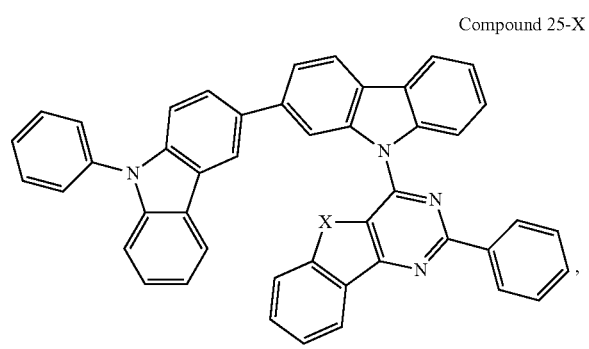
Compound 26-X
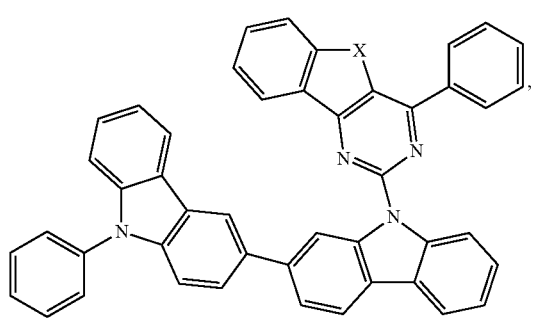
Compound 27-X
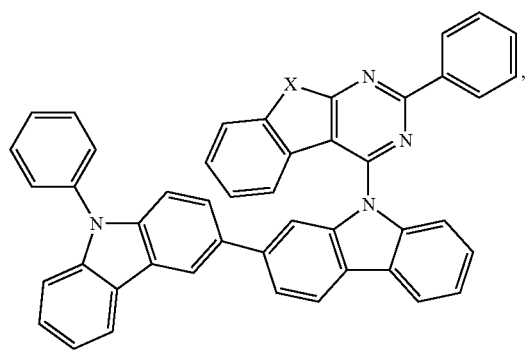
Compound 28-X
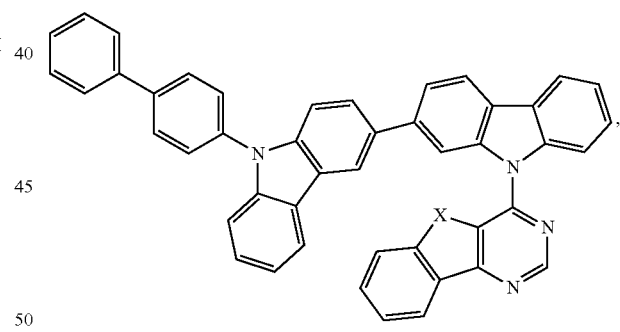
Compound 29-X
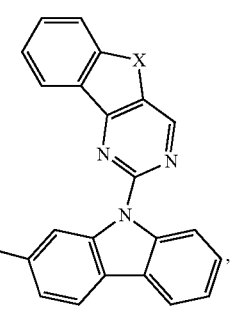

Compound 30-X
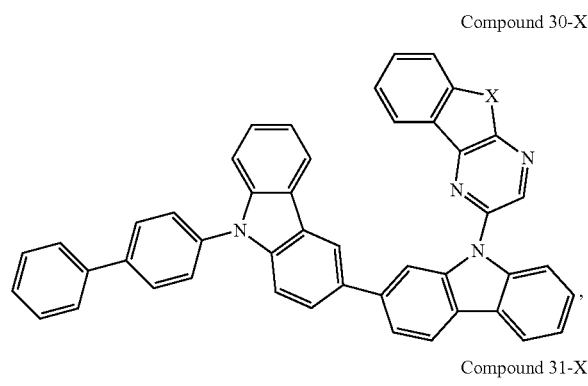
Compound 31-X
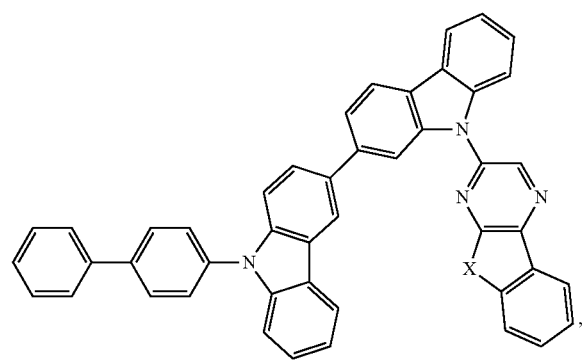
Compound 32-X
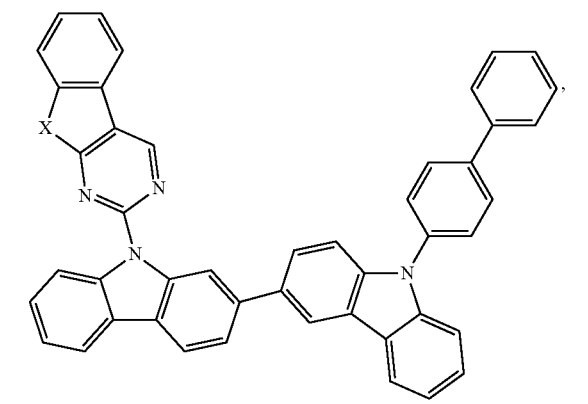
Compound 33-X
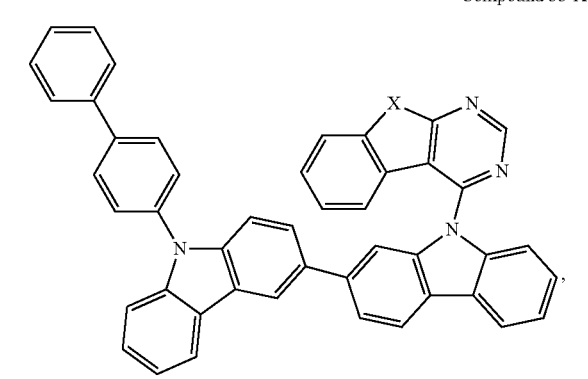
Compound 34-X
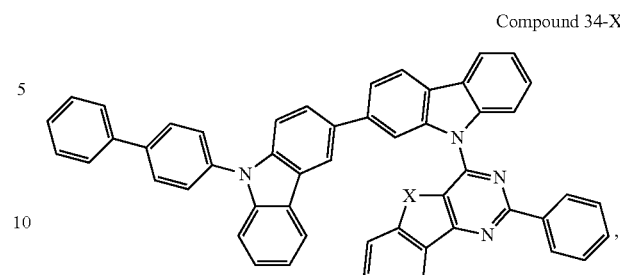
Compound 35-X
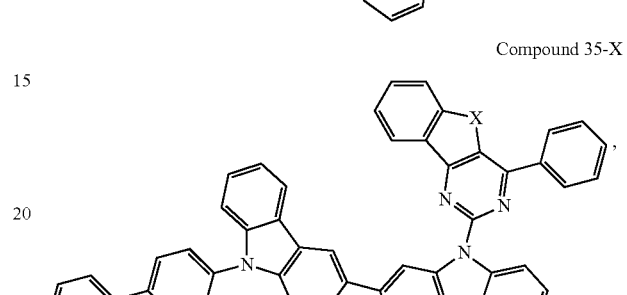
Compound 36-X
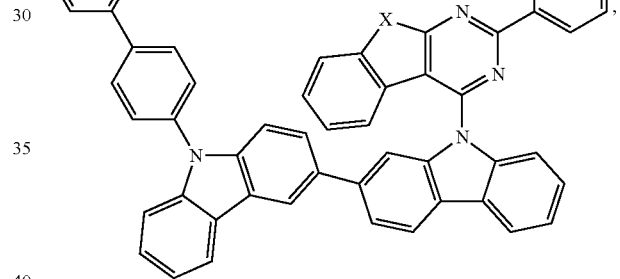
Compound 37-X
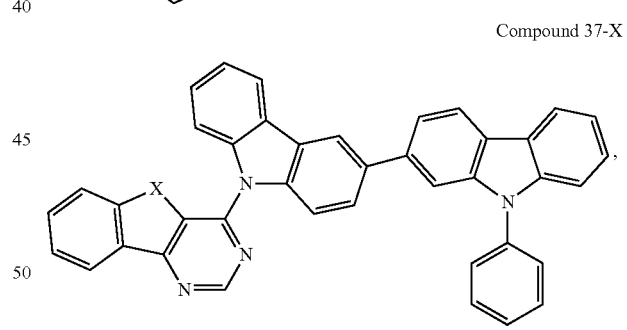
Compound 38-X
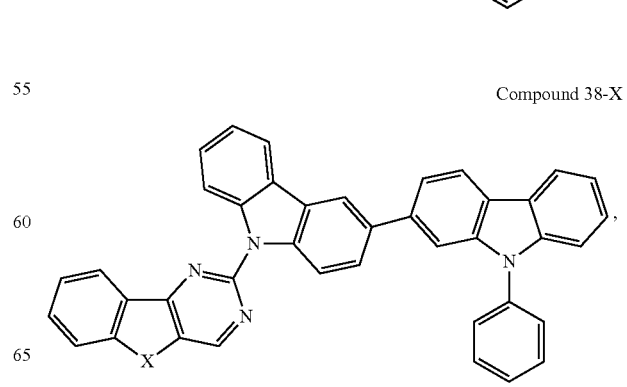

Compound 39-X
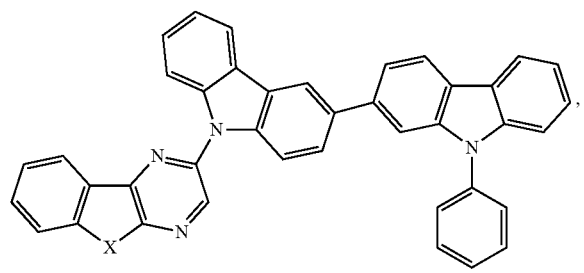
Compound 40-X
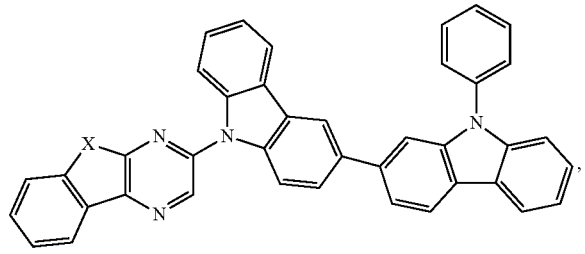
Compound 41-X
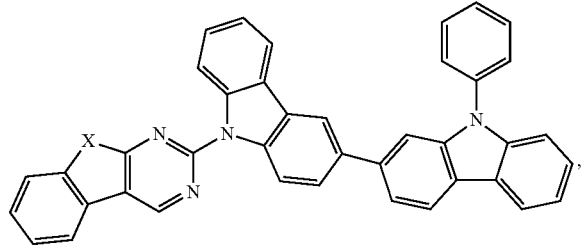
Compound 42-X
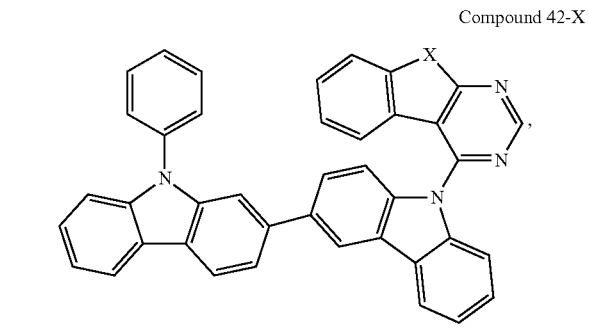
Compound 43-X
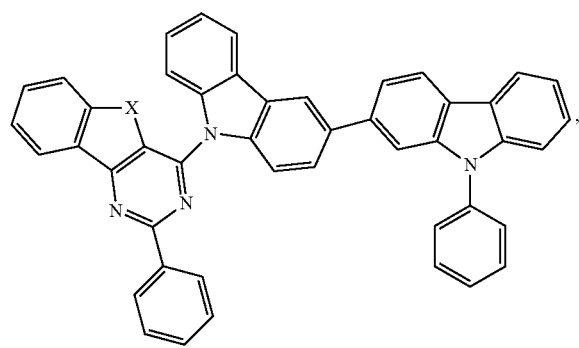
Compound 44-X
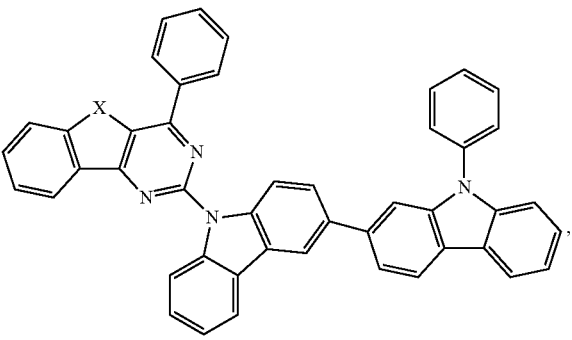
Compound 45-X
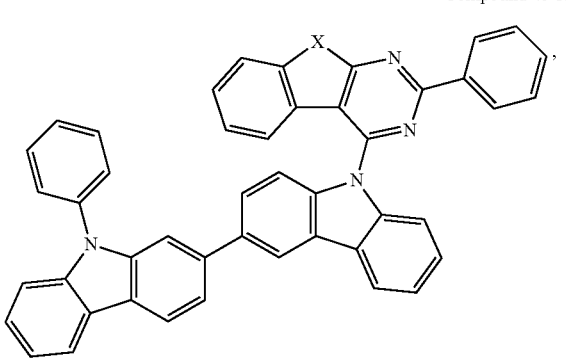
Compound 46-X
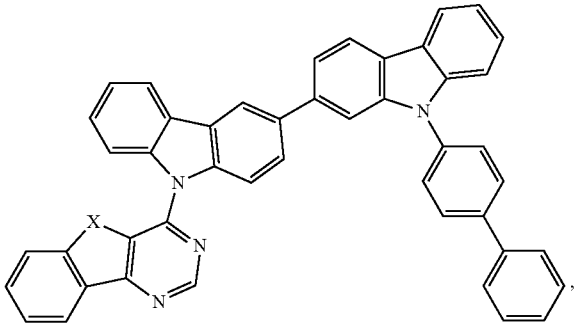
Compound 47-X
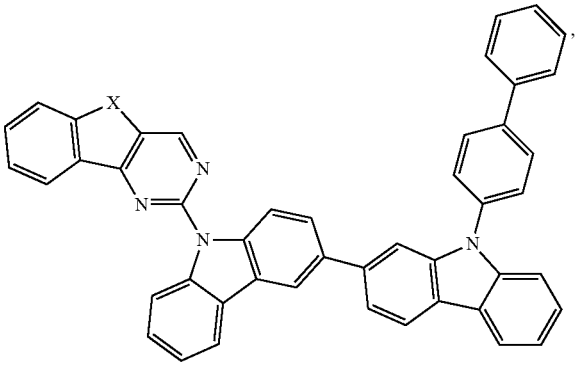

-continued
Compound 48-X
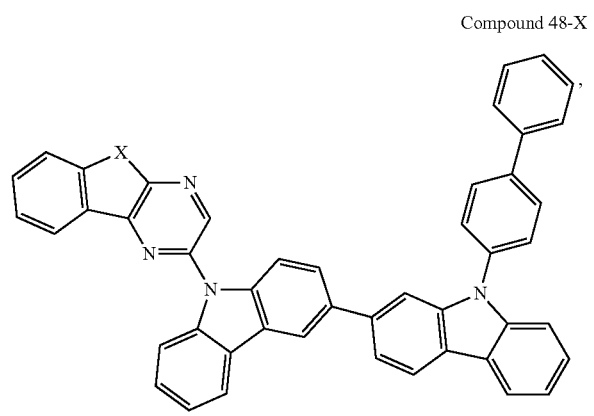
Compound 49-X
Compound 50-X
Compound 51-X
-continued
Compound 52-X
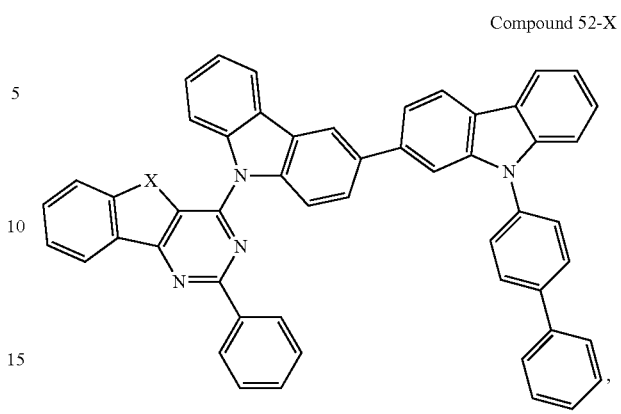
Compound 53-X
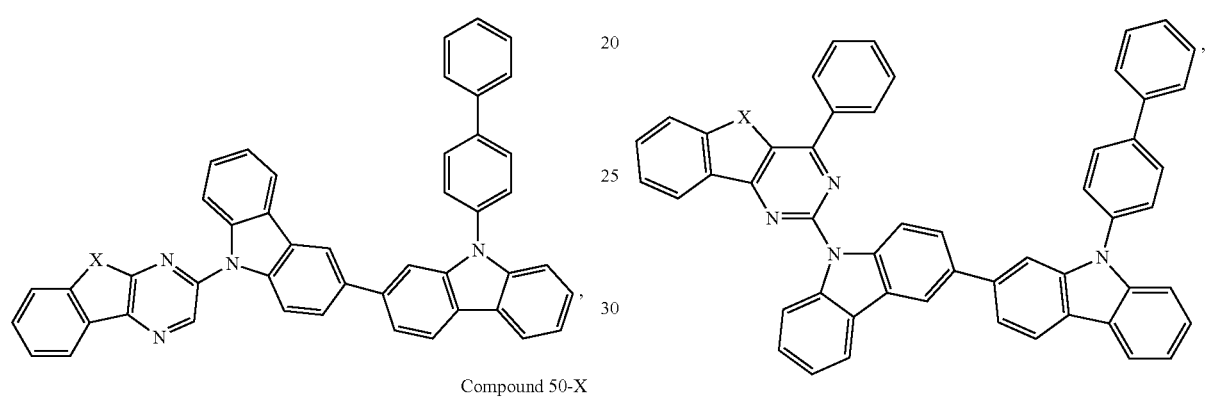
Compound 54-X
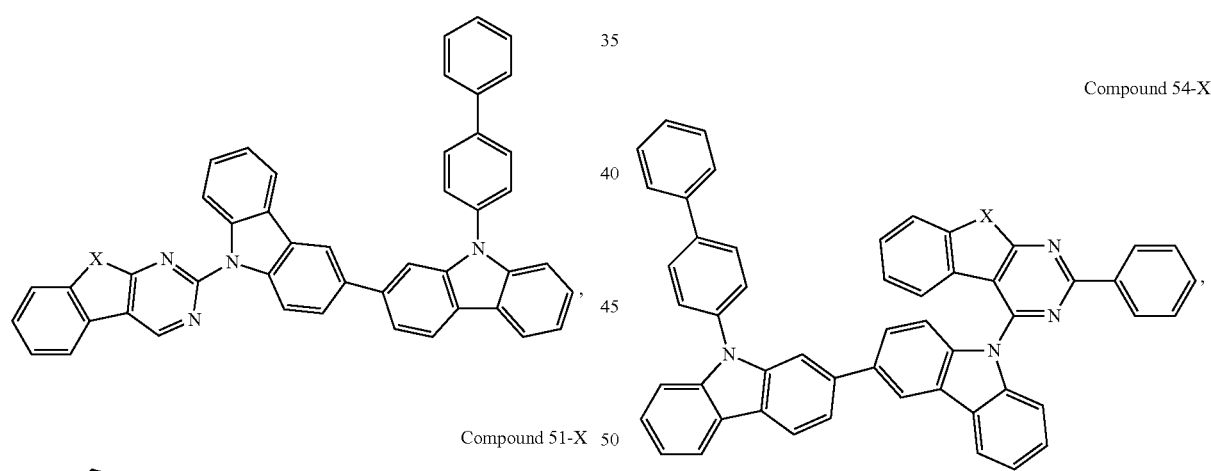
Compound 55-X
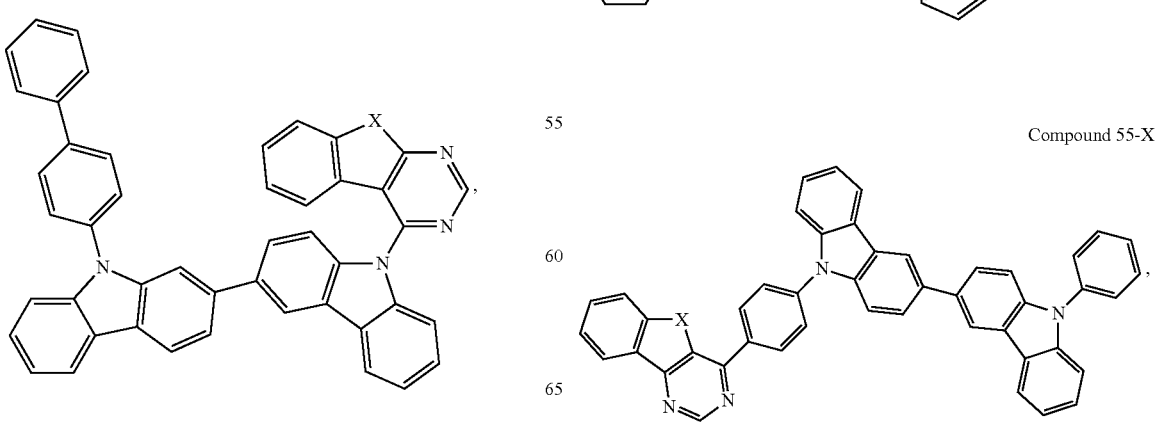

Compound 56-X
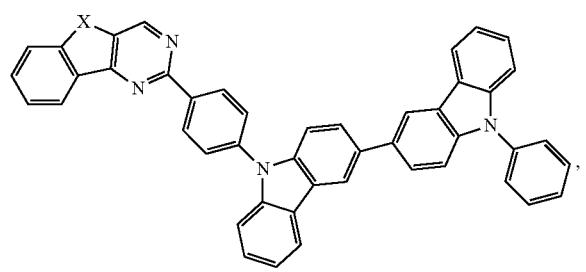
Compound 57-X
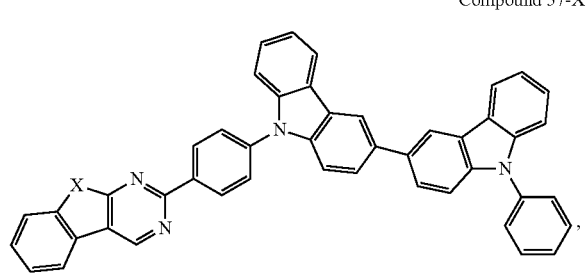
Compound 58-X
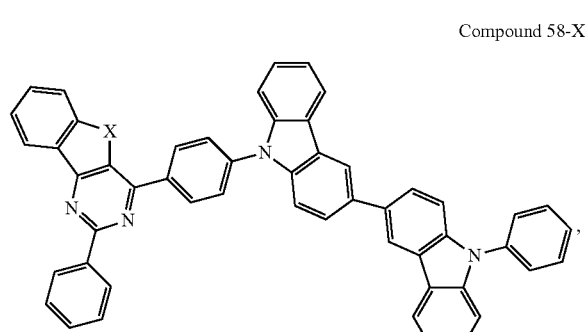
Compound 59-X
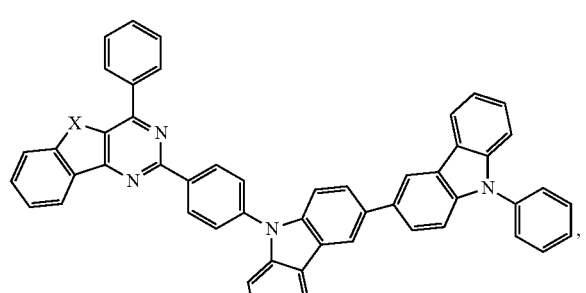
Compound 60-X
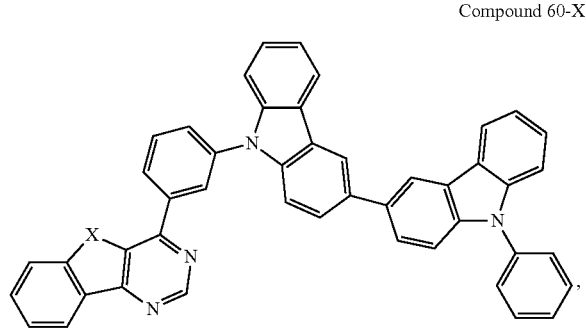
Compound 61-X
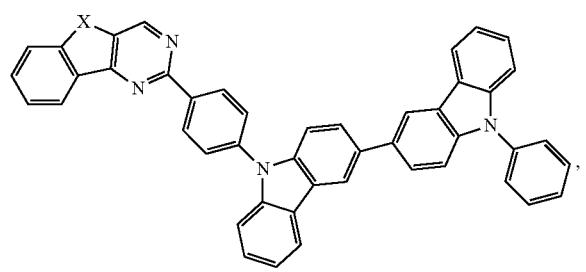
Compound 62-X
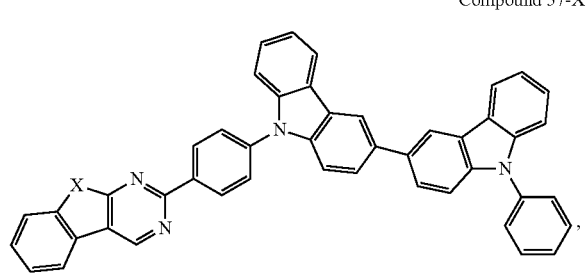
Compound 63-X
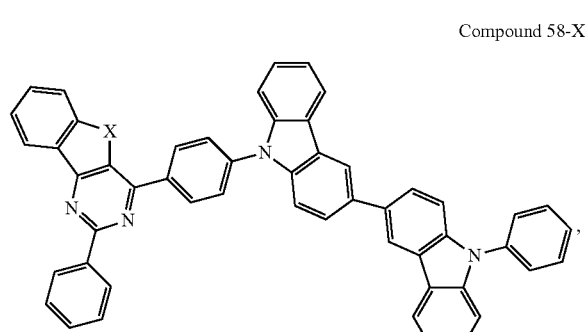
Compound 64-X
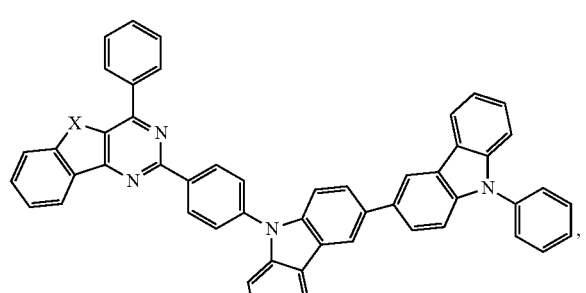
Compound 65-X
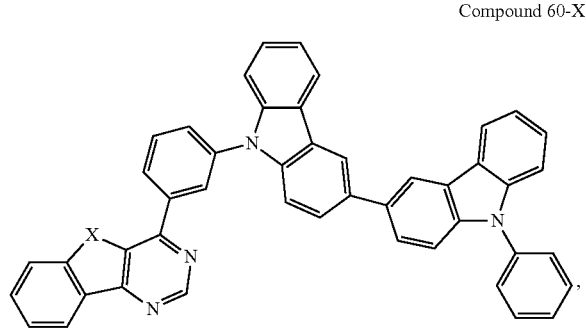

Compound 66-X
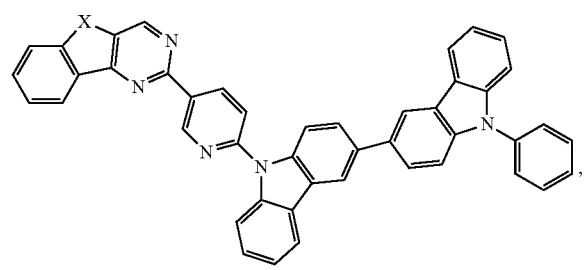
Compound 67-X
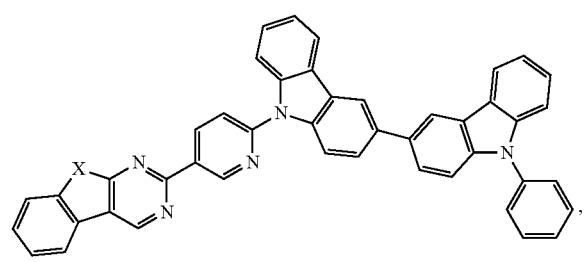
Compound 68-X
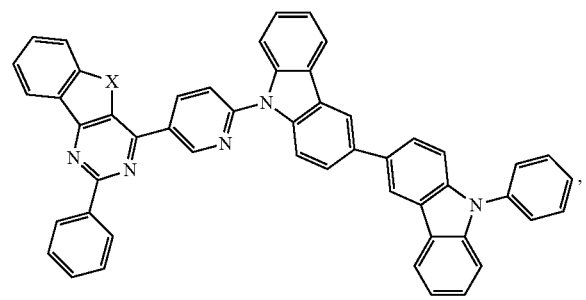
Compound 69-X
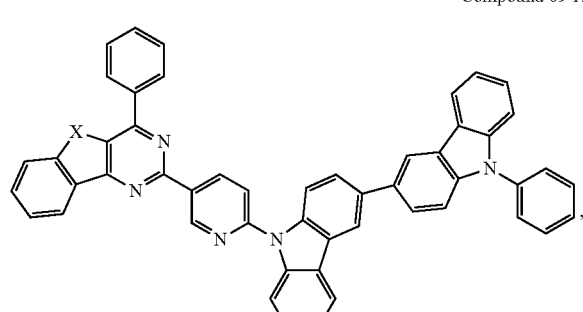
Compound 70-X
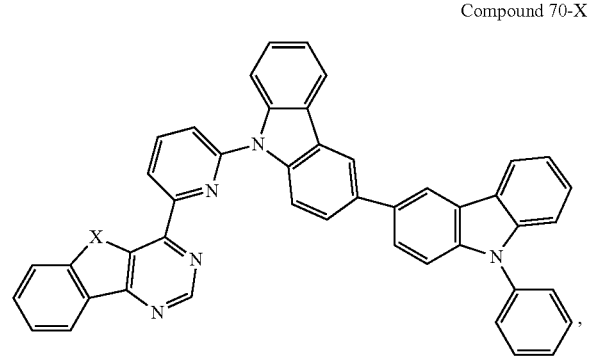
Compound 71-X
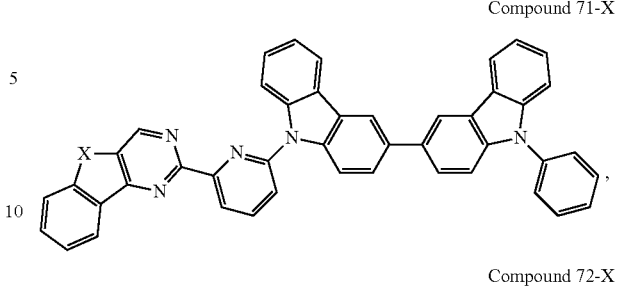
Compound 72-X
Compound 73-X
Compound 74-X
Compound 75-X
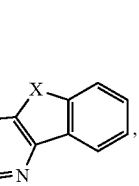

-continued
Compound 76-X
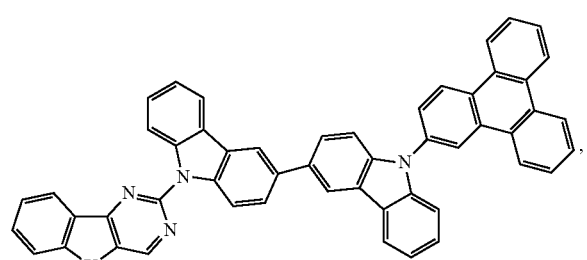
Compound 77-X
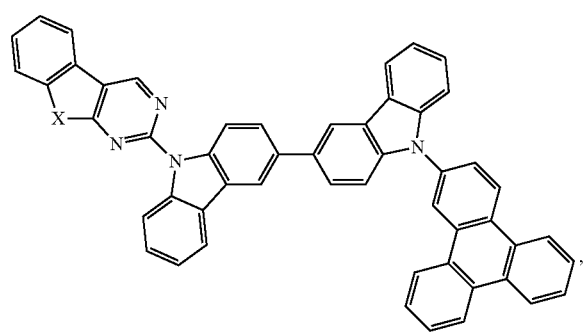
Compound 78-X
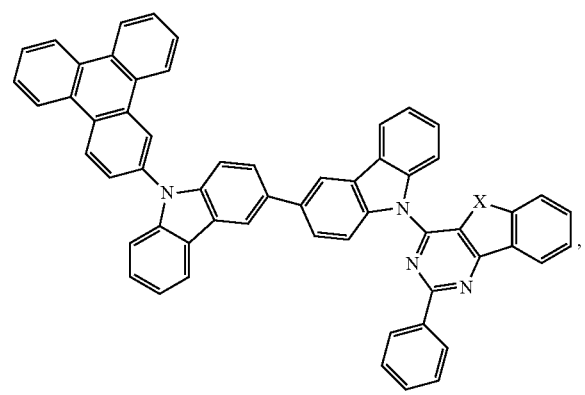
Compound 79-X
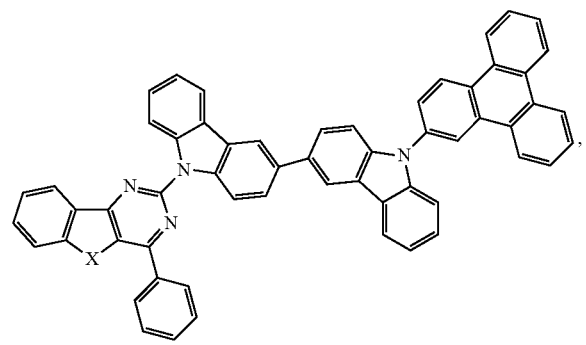
-continued
Compound 80-X
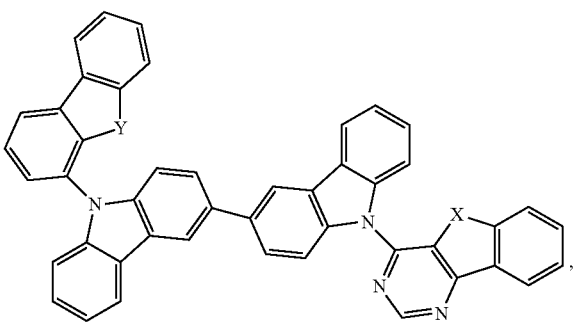
Compound 81-X
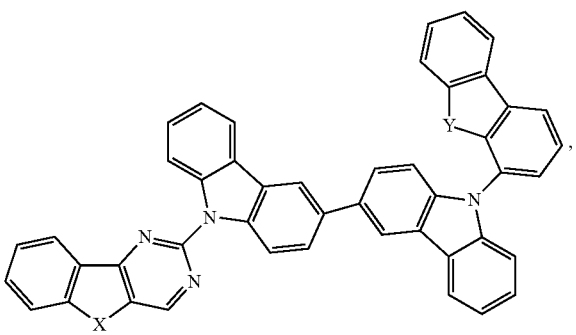
Compound 82-X
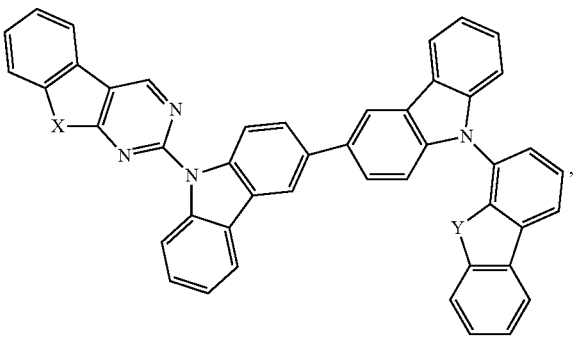
Compound 83-X
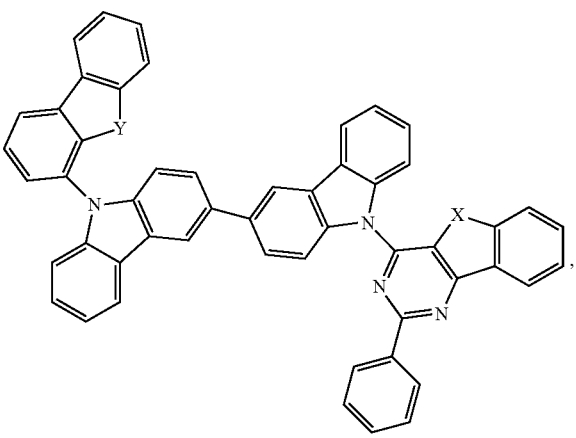

Compound 84-X
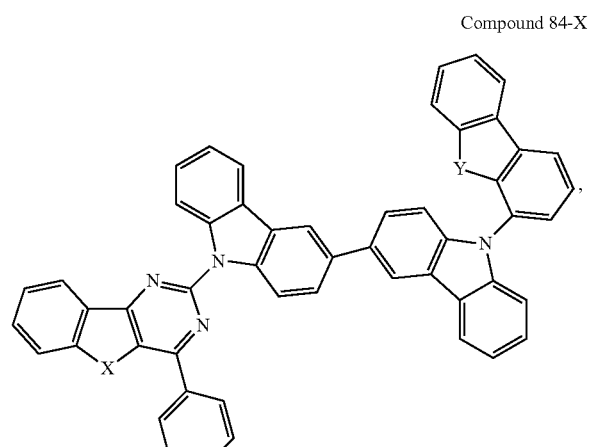
Compound 88-X
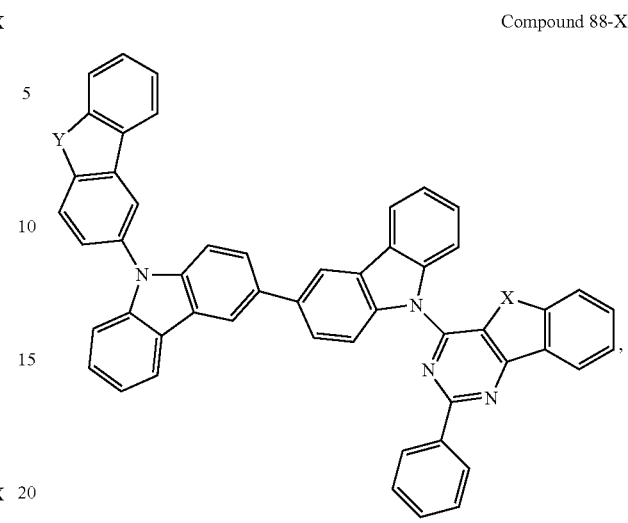
Compound 85-X
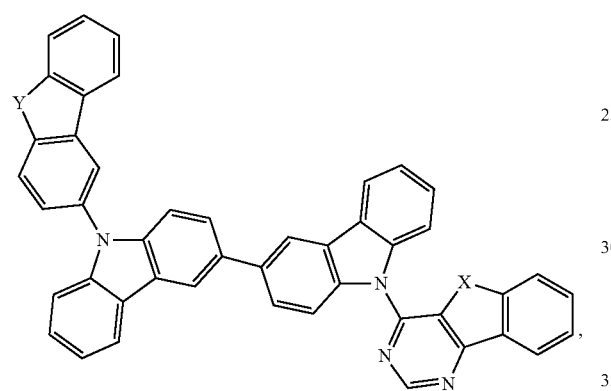
Compound 89-X
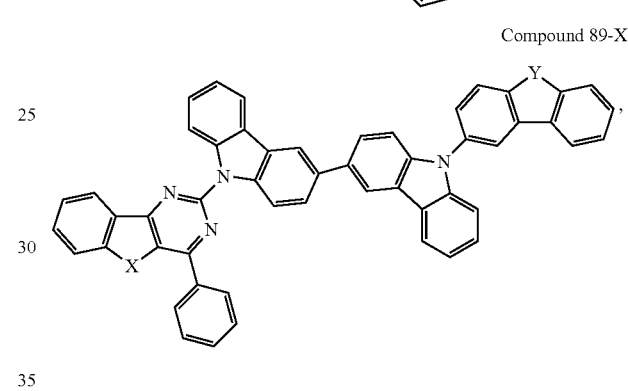
Compound 86-X
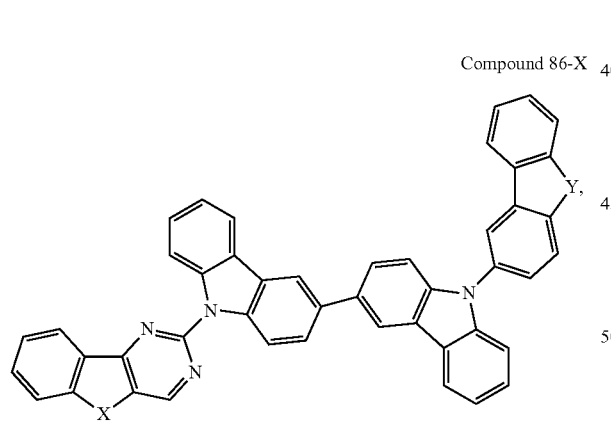
Compound 90-X
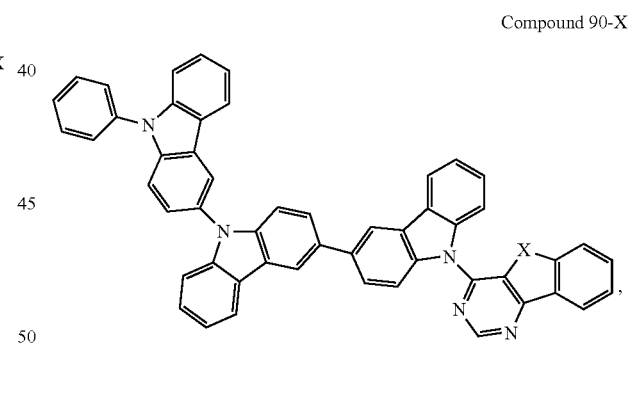
Compound 87-X
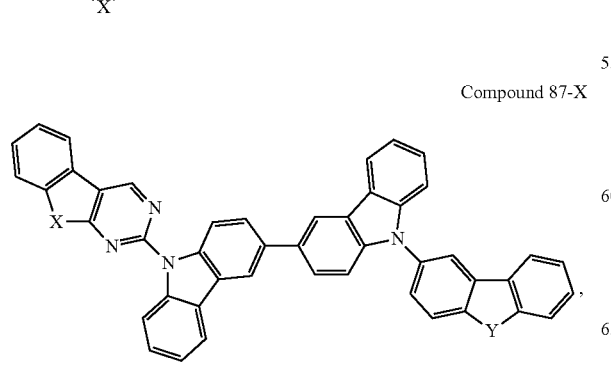
Compound 91-X
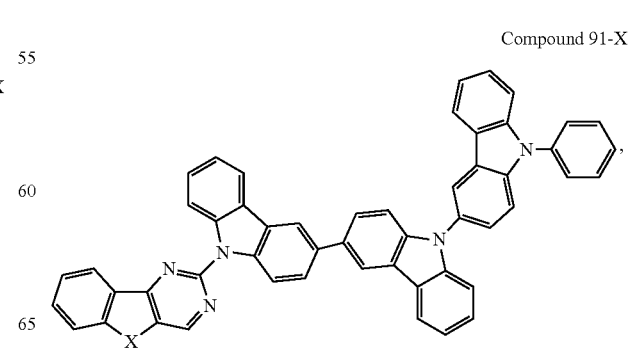

Compound 92-X
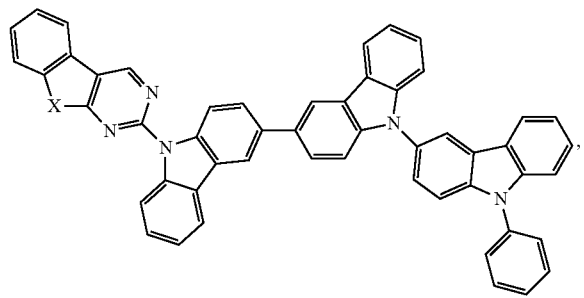
Compound 93-X
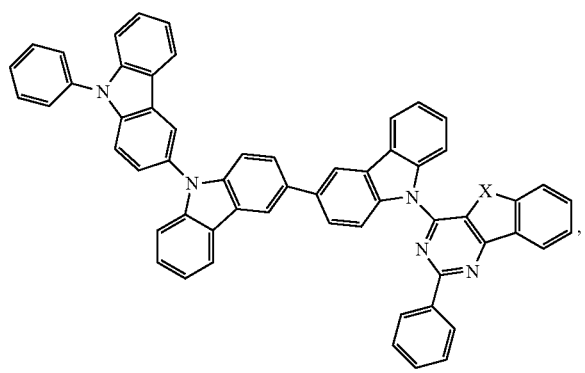
Compound 94-X
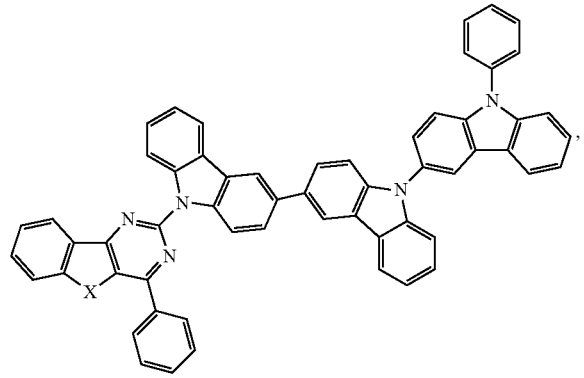
Compound 95-X
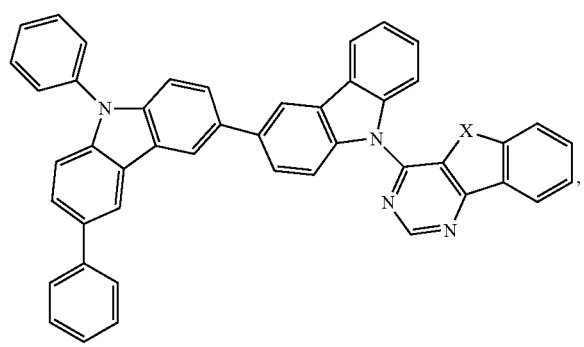
Compound 96-X
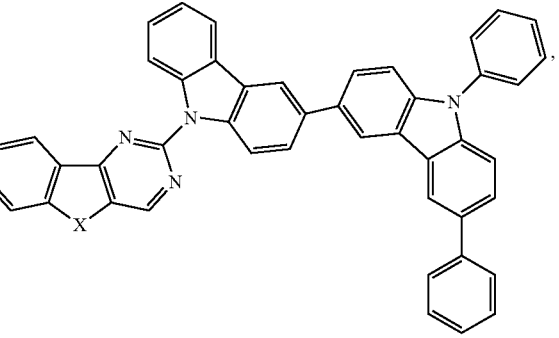
Compound 97-X
Compound 98-X
and
Compound 99-X
wherein Y in Compounds 80-X through 89-X is selected from the group consisting of O, S, and Se.
13. The first device of claim 11, wherein the organic layer is an emissive layer and the compound having Formula I is a host.

14. The first device of claim 13, wherein the organic layer further comprises an emissive dopant.
15. The first device of claim 14, wherein the emissive dopant is a transition metal complex having at least one ligand selected from the group consisting of:
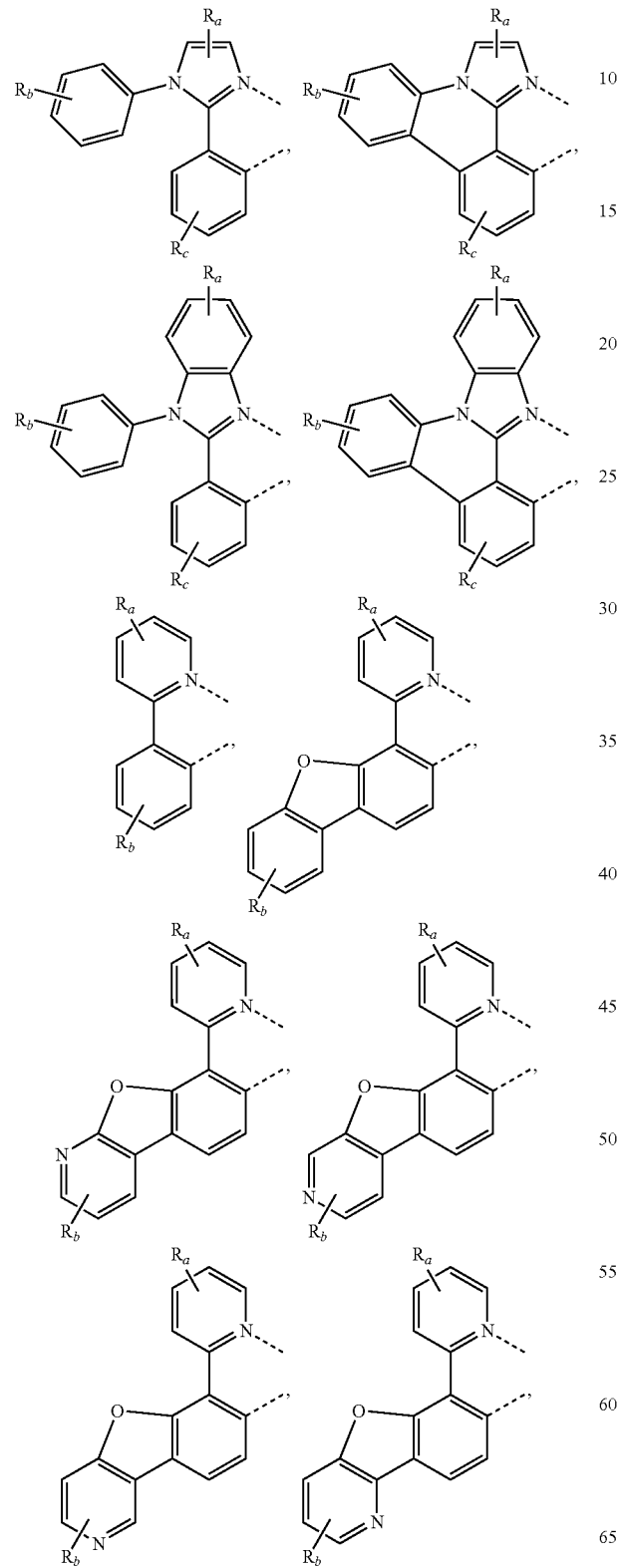
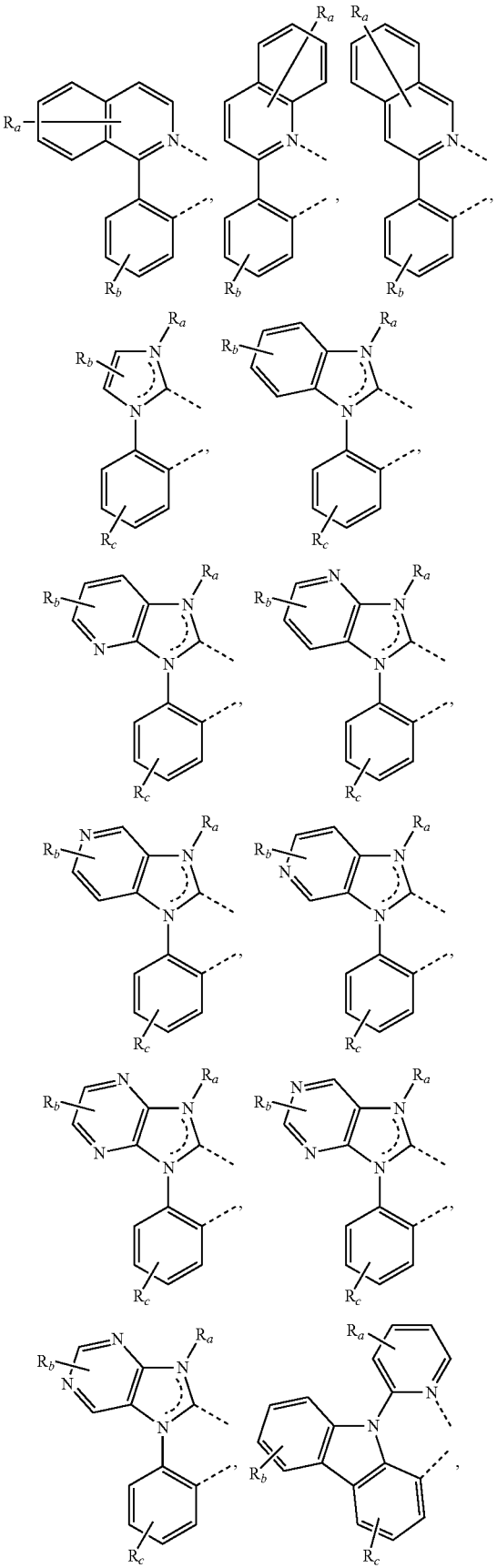

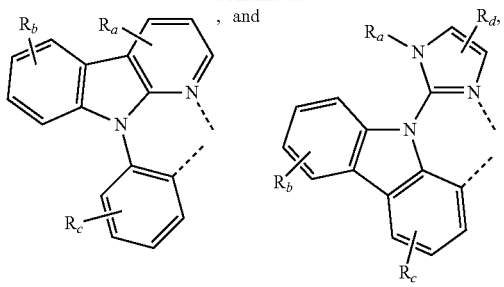

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

16. The first device of claim 11, wherein the device further comprises a blocking layer and the compound having Formula I is a blocking material in the blocking layer.

17. The first device of claim 11, wherein the device further comprises an electron transporting layer and the compound having Formula I is an electron transporting material in the electron transporting layer.

18. The first device of claim 11, wherein the first device is a consumer product.

19. The first device of claim 11, wherein the first device is an organic light-emitting device.

20. The first device of claim 11, wherein the first device comprises a lighting panel.

21. A formulation comprising a compound having a structure according to Formula I

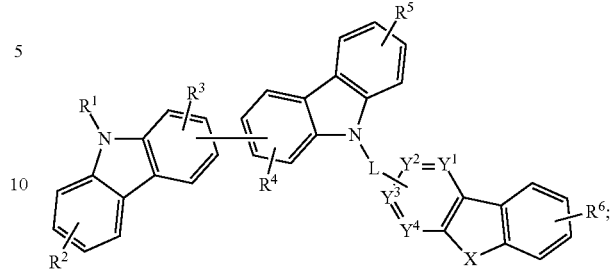

Formula I wherein $R^2$, $R^5$, and $R^6$ represent mono, di, tri, tetra substitutions or no substitution;

wherein $R^3$, and $R^4$ represent mono, di, tri substitutions or no substitution;

wherein L is a single bond or comprises an aryl or heteroaryl group having from 3-24 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;

wherein X is selected from the group consisting of O, S, and Se;

wherein each of $Y^1$, $Y^2$, $Y^3$, and $Y^4$ is carbon or nitrogen;

wherein at least two of $Y^1$, $Y^2$, $Y^3$, and $Y^4$ are nitrogen;

wherein at least one of $Y^1$, $Y^2$, $Y^3$, and $Y^4$ is carbon and bonded to L; and wherein $R^1$, $R^2$, $R^3$, $R^4$, $R^5$ and $R^6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

* * * * *

UNITED STATES PATENT AND TRADEMARK OFFICE
CERTIFICATE OF CORRECTION

PATENT NO. : 9,553,274 B2
APPLICATION NO. : 13/942921
DATED : January 24, 2017
INVENTOR(S) : Chuanjun Xia and Scott Joseph It is certified that error appears in the above-identified patent and that said Letters Patent is hereby corrected as shown below:

In the Claims

In Claim 10, Column 134, Lines 53-66, please delete

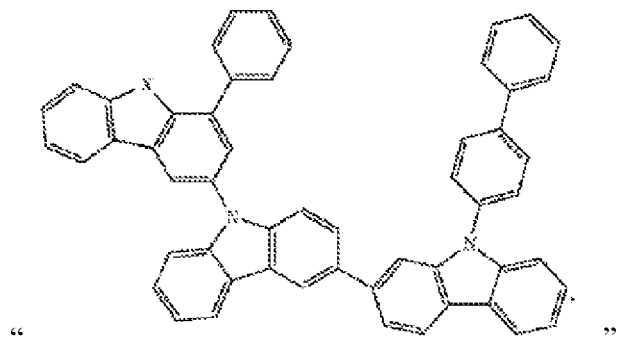

"

and insert --

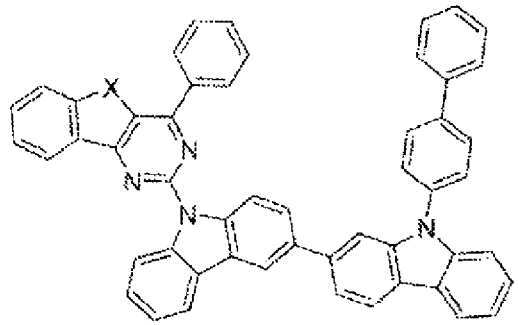

Compound 53-X

--

In Claim 10, Column 136, Lines 53-66, please delete

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,553,274 B2

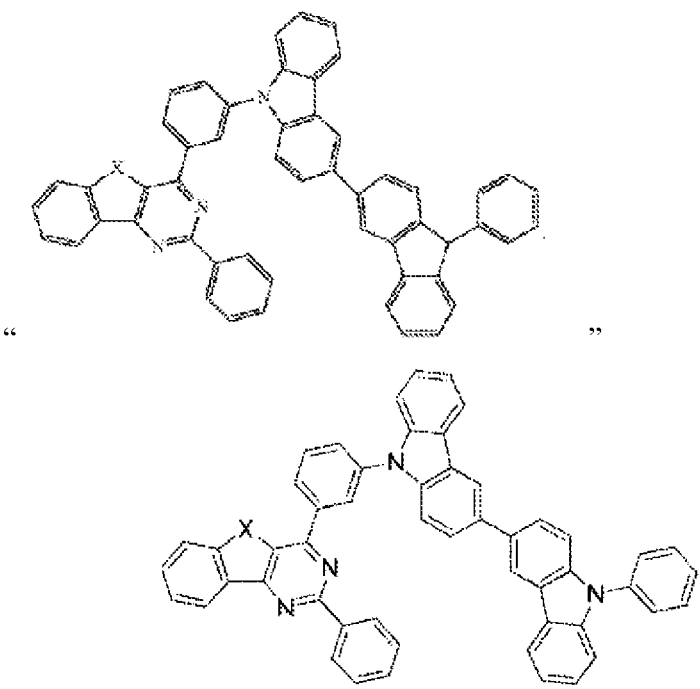

and insert -- " ,, --

In Claim 10, Column 137, Lines 53-66, please delete

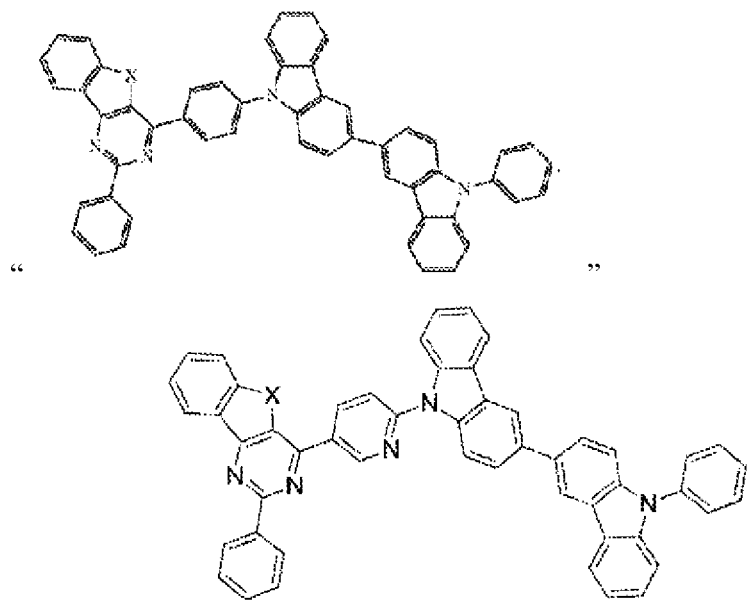

and insert -- " ,, --

In Claim 10, Column 143, Lines 33-48, please delete

CERTIFICATE OF CORRECTION (continued)
U.S. Pat. No. 9,553,274 B2

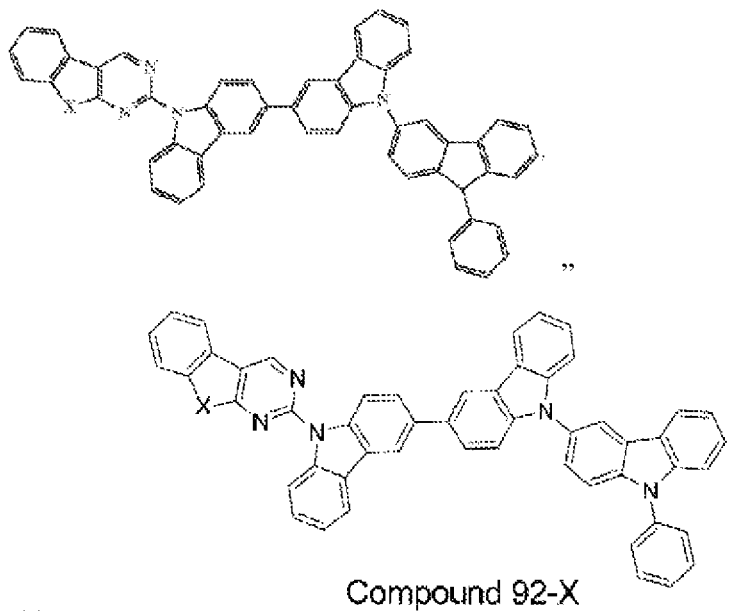

" "

and insert -- " --